(12) United States Patent
Lim et al.

(10) Patent No.: US 8,962,318 B2
(45) Date of Patent: Feb. 24, 2015

(54) METHOD OF DERIVING MESENCHYMAL STEM CELLS FROM ES CELLS USING FGF2

(75) Inventors: Sai Kiang Lim, Singapore (SG); Elias Lye, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1814 days.

(21) Appl. No.: 12/065,551

(22) PCT Filed: Aug. 15, 2006

(86) PCT No.: PCT/SG2006/000232
§ 371 (c)(1),
(2), (4) Date: Mar. 3, 2008

(87) PCT Pub. No.: WO2007/027156
PCT Pub. Date: Mar. 8, 2007

(65) Prior Publication Data
US 2008/0219957 A1 Sep. 11, 2008

Related U.S. Application Data

(60) Provisional application No. 60/713,992, filed on Sep. 2, 2005.

(51) Int. Cl.
*C12N 5/00* (2006.01)
*G01N 33/50* (2006.01)
*C12N 5/0775* (2010.01)
*C12Q 1/68* (2006.01)

(52) U.S. Cl.
CPC .......... *G01N 33/5044* (2013.01); *C12N 5/0662* (2013.01); *C12Q 1/6809* (2013.01); *C12N 2501/115* (2013.01); *C12N 2501/135* (2013.01); *C12N 2506/02* (2013.01)
USPC ............................. 435/375; 435/366; 435/325

(58) Field of Classification Search
CPC ........... C12N 5/0606; C12N 2830/008; C12N 2830/85; C12N 2506/02; C12N 5/0018; C12N 5/0623; C12N 15/85; C12N 2500/90; C12N 5/0031; C12N 5/0678; C12N 2500/02; A61K 35/12; A61K 35/28; A61K 8/982
See application file for complete search history.

(56) References Cited

U.S. PATENT DOCUMENTS

| | | | |
|---|---|---|---|
| 6,355,239 B1 | 3/2002 | Bruder et al. | |
| 7,005,252 B1* | 2/2006 | Thomson | 435/1.1 |
| 7,439,064 B2* | 10/2008 | Thomson et al. | 435/377 |
| 7,592,176 B2 | 9/2009 | Pike et al. | |
| 2002/0164308 A1 | 11/2002 | Reubinoff et al. | |
| 2002/0164791 A1* | 11/2002 | Van Der Kooy et al. | 435/366 |
| 2003/0036194 A1 | 2/2003 | Xu et al. | |
| 2004/0052771 A1 | 3/2004 | Lim | |
| 2005/0148034 A1 | 7/2005 | Hariri et al. | |
| 2005/0208029 A1 | 9/2005 | Umezawa et al. | |

FOREIGN PATENT DOCUMENTS

WO WO-01/88104 11/2001

OTHER PUBLICATIONS

Schuldiner, M. et al., Effects of eight growth factors on the differentiation of cells derived from human embryonic stem cells, Proceed. of Nat'l Acad. of Science, vol. 97(21): 11307-11312, Oct. 10, 2000.
Klimanskaya, I. et al., Human embryonic stem cells derived without feeder cells, The Lancet, vol. 365(9471): 1636-1641, May 7, 2005.
Barberi, T. et al., Derivation of multipotent mesenchymal precursors from human embryonic stem cells, PLOS Medicine, vol. 2: 554-560, Jun. 28, 2005.
Pittenger, M.F. et al., Multlineage potential of adult human mesenchymal stem cells, Amer. Assoc. for the Advancement of Science, vol. 284(5411): 143-147, Apr. 2, 1999.
Chen, S. et al., Effect on left ventricular function of intracoronary transplantation of autologous bone marrow mesenchymal stem cell in patients with acute myocardial infarction, American Journal of Cardiology, vol. 94(1): 92-95, Jul. 1, 2004.
Kinnaird, T. et al., Local delivery of marrow-derived stromal cells augments collateral perfusion through paracrine mechanisms, Circulation vol. 109(12): 1543-1549, Mar. 30, 2004.
Xaymardan, M. et al., Platelet-derived growth factor—AB promotes the generation of adult bone marrow-derived cardiac myocytes, Circulation Research vol. 94(5): E39-E45, Mar. 19, 2004.
Keller, G., Embryonic stem cell differentiation: emergence of a new era in biology and medicine, Genes & Development, vol. 19(10): 1129-1155, May 2005.
Barry, F. et al., Chondrogenic differentiation of mesenchymal stem cells from bone marrow: differentiation-dependent gene expression of matrix components, Experimental Cell Research, vol. 268(2): 189-200, Aug. 15, 2001.
Balconi et al., "Development of Endothelial Cells Lines from Embryonic Stem Cells," Arteriosclerosis, Thrombosis and Vascular Biology, vol. 20, pp. 1443-1451 (2000).
International Search Report mailed on Nov. 13, 200, for international Application No. PCT/SG2006/000233 filed Aug. 15, 2006, 4 pages.
Pesce et al., "Oct-4: Gatekeeper in the Beginning of mammalian Development," Stem Cells, vol. 19, pp. 271-278 (2001).
Reubinoff et al., "Embryonic stem cell lines from human blastocysts: Somatic differentiation in vitro," Nature Biotechnology, Nature Pub, vol. 18, pp. 399-404 (Apr. 2000).

(Continued)

*Primary Examiner* — Blaine Lankford
(74) *Attorney, Agent, or Firm* — Grimes & Yvon LLP

(57) ABSTRACT

We disclose a method comprising: (a) providing an embryonic stem (ES) cell; and (b) establishing a progenitor cell line from the embryonic stem cell; in which the progenitor cell line is selected based on its ability to self-renew. Preferably, the method selects against somatic cells based on their inability to self-renew. Preferably, the progenitor cell line is derived or established in the absence of co-culture, preferably in the absence of feeder cells, which preferably selects against embryonic stem cells. Optionally, the method comprises (d) deriving a differentiated cell from the progenitor cell line.

44 Claims, 37 Drawing Sheets

(56) References Cited

OTHER PUBLICATIONS

Stenderup et al., "Aging is associated with decreased maximal life span and accelerated senescence of bone marrow stromal cells," Bones, vol. 33, pp. 919-926 (2003).

Wobus et al., "Embryonic stem cells: Prospects for developmental biology and cell therapy," Physiological reviews, vol. 85, pp. 635-678 (Apr. 2005).

Yin et al., "Embryonic cell lines with endothelial potential: An in vitro system for studying endothelial differentiation," Arteriosclerosis thrombosis and vascular biology, vol. 24, pp. 691-696 (Apr. 2004).

* cited by examiner ii

FIGURE 5B (CONTINUED)

```
Tube: H3

Population                    #Events   %Parent   %Total
■ All Events                  10,000              100.0
└─▨ Scatter Gate               4,145    41.4       41.4
  └─☐ SSC Gate                 4,145   100.0       41.4
    └─■ FSC Gate               4,144   100.0       41.4
      ├─▨ Q1                     653    15.7        6.5
      │ └─▨ PE ONLY              314    48.2        3.1
      ├─▨ Q2                     932    22.6        9.3
      │ └─▨ D6                   438    46.9        4.4
      ├─■ Q3                   1,332    39.7       13.3
      │ └─■ UNSTAINED            568    40.1        5.7
      └─▨ Q4                   1,327    32.0       13.3
        └─▨ FITC ONLY            495    37.3        5.0
```

METHOD OF DERIVING MESENCHYMAL STEM CELLS FROM ES CELLS USING FGF2

Reference is made to U.S. provisional application Ser. No. U.S. 60/713,992 filed Sep. 2, 2005.

The foregoing application, and each document cited or referenced in each of the present and foregoing applications, including during the prosecution of each of the foregoing application ("application and article cited documents"), and any manufacturer's instructions or catalogues for any products cited or mentioned in each of the foregoing application and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD

The present invention relates to the fields of development, cell biology, molecular biology and genetics. More particularly, the invention relates to a method of deriving mesenchymal stem cells from embryonic stem cells.

BACKGROUND

Stem cells, unlike differentiated cells have the capacity to divide and either self-renew or differentiate into phenotypically and functionally different daughter cells (Keller, Genes Dev. 2005; 19:1129-1155; Wobus and Boheler, *Physiol Rev.* 2005; 85:635-678; Wiles, *Methods in Enzymology.* 1993; 225:900-918; Choi et al, *Methods Mol Med.* 2005; 105:359-368).

The pluripotency of mouse embryonic stem cells (ESCs) and their ability to differentiate into cells from all three germ layers makes embryonic stem cells an ideal source of cells for regenerative therapy for many diseases and tissue injuries (Keller, Genes Dev. 2005; 19:1129-1155; Wobus and Boheler, Physiol Rev. 2005; 85:635-678). However, this very property of embryonic stem cells also poses a unique challenge, i.e. generating the appropriate cell types for the treatment of a specific diseased or injured tissue in sufficient quantity and homogeneity to ensure therapeutic efficacy, and inhibiting the generation of other cell types that may have a deleterious effect on the tissue repair and regeneration. At present, protocols that either enhance differentiation of embryonic stem cells towards specific lineages and/or enrich for specific tissue cell types are too inefficient and generally yield heterogeneous cell populations that might be tumorigenic (Keller, *Genes Dev.* 2005; 19:1129-1155; Wobus and Boheler, *Physiol Rev.* 2005; 85:635-678).

Mesenchymal stein cells (MSCs) are multipotent stem cells that have documented evidence of therapeutic efficacy in treating musculoskeletal injuries, improving cardiiac function in cardiovascular disease and ameliorating the severity of GVHD (Le Blanc and Pittenger, 2005). Being lineage restricted, they have limited but robust potential to differentiate into mesenchymal cell types, e.g adipocytes, chondrocytes and osteocytes, and have negligible risk of teratoma formation. Host immune rejection of transplanted MSCs is routinely circumvented through autologous or allogeneic transplantation. MSCs can be isolated from several adult tissues including bone marrow (BM), adipose tissues (ad), cord blood and expanded ex vivo. However, availability of tissues for their isolation remains limiting and requires risky invasive procedures, and ex vivo expansion of MSCs while significant, is nonetheless finite.

An alternative source of MSCs is the unlimited supply of infinitely expandable and pluripotent human embryonic stem cells (hESCs) that will also eliminate the need for potentially risky invasive techniques. Host immune rejection of hESC-derived MSCs (hESC-MSC) could potentially be circumvented by either autologous hESCs generated by therapeutic cloning or immune compatible allogeneic hESCs when banks of hESC lines become sufficiently large.

The isolation of MSC or MSC-like cells from hESC has been previously described. Barberi, et al. (2005) PLoS Med 2, e161 describes a protocol which involves co-culturing hESCs with mouse OP9 cells in the presence of serum for 40 days before sorting for CD73+ cells that constitute about 5% of the total cell population. Xu, C. et al. (2004) Stem Cells 22, 972-80 describes a protocol which involves infecting hESC-derived embryoid bodies with a retrovirus expressing hTERT (Xu et al). However, the critical components of these protocols i.e. viral infection of exogenous DNA, exposure to mouse cells and use of serum introduce unacceptable risks of tumorigenicity and xenozootic infection, and preclude the use of these MSCs for clinical applications.

This invention seeks to solve this and other problems with methods in the art.

SUMMARY

We provide, according to the invention, mesenchymal stem cells (MSC), mesenchymal stem cell lines, differentiated mesenchymal stem cells, methods of obtaining these and uses of these, as set out in the claims. Preferrred embodiments are set out in the claims and are described in the description.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *Oligonucleotide Synthesis. A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855; and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE DRAWINGS

FIG. 1A. Cellular morphology under phase contrast.

FIG. 1B. Expression of pluripotency-associated genes in hESC-MSC. Transcript levels are measured by Taqman-based quantitative RT-PCR and normalized to that of hESC. The transcript level in hESC is derived from the average of HuES9 and H1 hESC lines.

FIG. 1C. Western blot analysis for pluripotency-associated genes in HuES9 and H1 hESC lines, HuES9.E1 HuES9.E3 and H1.E2 hESC-MSC cultures and E14 mouse ESC line.

FIG. 1D. Renal subcapsular transplantation of HuES9 and HuES9.E1. Paraffin-embedded, H&E stained cross sections of kidney four months after transplantation with either HuES9.E1 (top) or HuES9 (bottom).

FIG. 1D. Alkaline phosphatase activity in human HuES9 ESC line, mouse E14 ESC line, mouse embryonic fibroblast (MEF) feeder and HuES9.E1.

FIG. 1F. Genomic DNA analysis by PCR for the presence of human Alu and mouse c-mos repeat sequences.

FIG. 1G. Chromosomal analysis of HuES9.E1 by G-banding (top panel) and Spectral Karyotyping (SKY) (middle panel). Inversion of chromosome 9 shown in bottom panel.

FIG. 2A. HuES9.E1 HuES9.E3 and H1.E2 hESC-MSCs, HuES9 hESCs, and murine embryonic fibroblast feeder cells are stained and analyzed on a Cyan LX (Dako North America, Inc., Carpinteria, Calif.) instrument using WinMDI software. Nonspecific fluorescence is determined by incubation of similar cell aliquots with isotype-matched mouse monoclonal antibodies.

FIG. 2B. HuES9.E1 and HuES9.E3 hESC-MSCs are passaged twice in serum-containing BM-MSC media before being analyzed in parallel with BM-MSCs by FACS analysis.

FIG. 3A. Adipogenesis. i) Day 14 after inducing adipogenesis, cells are stained for oil droplets by oil red; ii) PPARγ mRNA at day 7 and day14 are measured by Taqman quantitative RT-PCR. All values are normalized to that of HuES9.E1; iii) Relative PPARγ mRNA levels in HuES9 and HI hESCs, their derivative MSC cell cultures (HuES9.E1, HuES9.E3 and H1.E2) and adult tissue-derived MSCs (BM-MSC and ad-MSC) as measured by Taqman quantitative RT-PCR. All values are normalized to that of HuES9.E1.

FIG. 3B. Chondrogenesis. i) Day 21 after inducing chondrogenesis, cells are stained for proteoglycans by alcian blue (left) and immunoreactivity to collagen type II using a HRP-based visualization assay; ii) Aggrecan and PPARγmRNA at day 7 and day14 are measured by Taqman quantitative RT-PCR. All values are normalized to that of HuES9.E1; iii) Relative PPARγmRNA levels in HuES9 and HI hESCs, their derivative MSC cell cultures (HuES9.E1, HuES9.E3 and H1.E2) and adult tissue-derived MSCs (BM-MSC and ad-MSC) as measured by Taqman quantitative RTPCR. All values are normalized to that of HuES9.E1.

FIG. 3C. Osteogenesis i) Day 21 after inducing chondrogenesis, cells are stained for mineralization by von Kossa stain, ii, iii) Bone-specific alkaline phosphatase (ALP) and bone sialoprotein (BSP) mRNA at day 7 and day14 are measured by Taqman quantitative RT-PCR. All values are normalized to that of HuES9.E1

FIG. 4A. Hierarchical clustering of expressed genes in three hESC-MSC cultures consisting of HuES9.E1, HuES9.E3, and H1.E2, three BMMSC samples, three ad-MSC samples and three hESC lines consisting of HuES9, H1 and Hes3.

FIG. 4B. Pairwise comparison of gene expression between hESC-MSCs and BMMSCs (left) and between hESC-MSCs and hESCs (right).

FIG. 4C. Analysis of commonly expressed genes (<2 fold difference) in hESC-MSCs and BM-MSCs. The genes are classified into biological processes using the Panther classification system. Each biological process is determined if it is significantly over- or under-represented ($p<0.01$) by comparing the observed frequency of genes to the expected frequency of genes in the NCBI: *H. sapiens* gene database of 23481 genes for each biological process. Significantly over- or under-represented processes are grouped and graphically presented.

FIGS. 4D-4E. Analysis of differentially expressed genes (>2 fold difference) in hESC-MSCs and BM-MSCs. Biological processes that are significantly over- or underrepresented ($p<0.01$) by genes highly expressed in hESC-MSCs or BM-MSCs are grouped and graphically presented.

FIG. 5A. FACS analysis HuES9.E1 HuES9.E3 and H1.E2 hESC-MSCs, HuES9 hESCs, and murine embryonic fibroblast feeder cells are stained and analyzed for the presence of CD24 on a Cyan LX (Dako North America, Inc., Carpinteria, Calif.) instrument using WinMDI software. Nonspecific fluorescence is determined by incubation of similar cell aliquots with isotype-matched mouse monoclonal antibodies.

FIG. 5B. Sorting for CD105+, CD24– cells from HuES9 cells that have been trypsinized and propagated without feeder in media supplemented with PDGF and FGF2 for one week. CD105+, CD24– cells represented in Q4 are selected for culture.

FIG. 5C. Pairwise comparison of gene expression between Q4.1 and each of the other Q4 cultures, namely Q4.2 to Q4.5.

FIG. 5D. Pairwise comparison of gene expression between all Q4 cultures and hESC-MSCs consisting of HuES9.E1, HuES9.E3, and H1.E2, and between all Q4 cultures and BM-MSCs, FIG. 5E. SKY analysis of Q4.3.

DETAILED DESCRIPTION

Obtaining Mesenchymal Stem Cells (MSC)

Figure 1A:
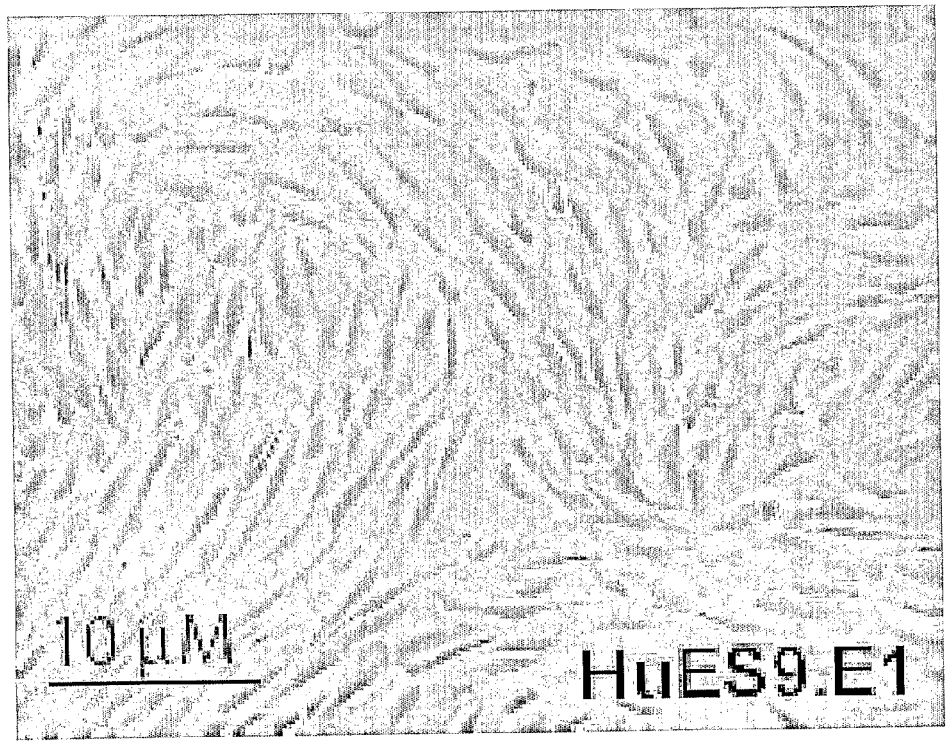
FIGS. 1A-1G. Characterisation of hESC-MSC cultures.

The prior art methods of obtaining mesenchymal stem cells (MSC) or MSC-like cells from hESCs involve either transfection of a human telomerase reverse transcriptase (hTERT) gene into differentiating hESCs (Xu et al., 2004) or coculture with mouse OP9 cell line (Barberi et al., 2005). The use of exogenous genetic material and mouse cells in these derivation protocols introduces unacceptable risks of tumorigenicity or infection of xenozootic infectious agents.

In contrast, our method provides for a clinically relevant and reproducible protocol for isolating similar or identical (preferably homogenous) MSC populations from differentiating hESCs. In general, our method comprises dispersing a embryonic stem (ES) cell colony into cells. The cells are then plated out and propagated. The cells are propagated in the absence of co-culture in a serum free medium comprising fibroblast growth factor 2 (FGF2), in order to obtain mesenchymal stem cells (MSCs).

Thus, our protocol does not require serum, use of mouse cells or genetic manipulations and requires less manipulations and time, and is therefore highly scalable. The Examples describe the isolation of MSCs from two different hESC lines, HuES9 and H-1 and also a third one, Hes-3[23], and demonstrates the robustness of the protocol. Human ES cell derived MSCs (hESC-MSCs) obtained by the methods and compositions described here are remarkably similar to bone-marrow derived MSCs (BM-MSCs).

In preferred embodiments, the embryonic stem cell culture comprises a human embryonic stem cell (hESC) culture.

In a one embodiment, a method of generating mesenchymal stem cells (MSC) comprises trypsinizing and propagating hESCs without feeder support in media supplemented with FGF2 and optionally PDGF AB before sorting for CD105+CD24− cells.

In a preferred embodiment, the method comprises sorting for CD105+, CD24− cells from trypsinized hESCs one week after feeder-free propagation in a media supplemented with FGF2 and optionally PDGF AB will generate to generate a hESC-MSC cell culture in which at least some, preferably substantially all, more preferably all cells are similar or identical (preferably homogenous) to each other.

The methods described here for generating clinically relevant hESCMSC cultures that are physically, biologically and functionally similar to BM-MSCs could potentially alleviate the limiting supply of BM for isolation of BM-MSCs that have demonstrated therapeutic efficacy in many clinical and preclinical animal studies[10,25]. This will also remove the need for risky invasive BM aspiration procedure, reduce the waiting time and cost of preparing BM-MSCs on a per-patient basis, and reduce batch to batch variations. Furthermore, the robust derivation of MSCs from a defined cell type such as hESC provides a useful model to study and better understand the derivation and biology of MSC that has remain an enigma despite its present widespread clinical and preclinical applications[9].

Further uses of the mesenchymal stem cells generated by the process include replacement of adult tissue-derived MSCs in clinical or therapeutic applications; replacement of adult tissue-derived MSCs as feeders for propagation of other cell types such as human ESCs, expansion of cord blood or bone marrow stem cell populations; and preparation of MSC-conditioned media for treatment of cardiovascular disease.

Disaggregating Embryonic Stem Cell Colonies

Our methods of producing mesenchymal stem cells comprise dispersing or disaggregating an embryonic stem cell colony into cells.

The embryonic stem cell colony may comprise a huES9 colony (Cowan Calif., Klimanskaya I, McMahon J, Atienza J, Witmyer J, et al. (2004) *Derivation of embryonic stem-cell lines from human blastocysts*. N Engl J Med 350: 1353-1356) or a H1 ESC colony (Thomson J A, Itskovitz-Eldor J, Shapiro S S, Waknitz M A, Swiergiel J J, et al. (1998) *Embryonic Stem Cell Lines Derived from Human Blastocysts*. Science 282: 1145-1147.).

Preferably, the cells in the colony are disaggregated or dispersed to a substantial extent, i.e., at least into clumps. More preferably, the colony is disaggregated or dispersed to the extent that all the cells in the colony are single, i.e., the colony is completely disaggregated.

The disaggregation may be achieved with a dispersing agent.

The dispersing agent may be anything that is capable of detaching at least some embryonic stem cells in a colony from each other. The dispersing agent may preferably comprise a reagent which disrupts the adhesion between cells in a colony, or between cells and a substrate, or both. Preferably, the dispersing agent may comprise a protease.

In preferred embodiments, the dispersing agent comprises trypsin. The treatment with trypsin may last for example for 3 minutes or thereabouts at 37 degrees C. The cells may then be neutralised, centrifuged and resuspended in medium before plating out.

In preferred embodiments, the method comprises dispersing a confluent plate of human embryonic stem cells with trypsin and plating the cells out.

The disaggregation may comprise at least some of the following sequence of steps: aspiration, rinsing, trypsinization, incubation, dislodging, quenching, re-seeding and aliquoting. The following protocol is adapted from the Hedrick Lab, UC San Diego (http://hedricklab.ucsd.edu/Protocol/COSCell.html).

In the aspiration step, the media is aspirated or generally removed from the vessel, such as a flask. In the rinsing step, the cells are rinsed with a volume, for example 5-10 mls, of a buffered medium, which is preferably free from $Ca^{2+}$ and $Mg^{2+}$. For example, the cells may be rinsed with calcium and magnesium free PBS. In the trypsinization step, an amount of dispersing agent in buffer is added to the vessel, and the vessel rolled to coat the growing surface with the dispersing agent solution. For example, 1 ml of trypsin in Hank's BSS may be added to a flask.

In the incubation step, the cells are left for some time at a maintained temperature. For example, the cells may be left at 37° C. for a few minutes (e.g., 2 to 5 minutes). In the dislodging step, the cells may be dislodged by mechanical action, for example by scraping or by whacking the side of the vessel with a hand. The cells should come off in sheets and slide down the surface.

In the quenching step, a volume of medium is added to the flask. The medium preferably contains a neutralising agent to stop the action of the dispersing agent. For example, if the dispersing agent is a protease such as trypsin, the medium may contain a protein, such as a serum protein, which will mop up the activity of the protease. In a particular example, 3 ml of serum containing cell culture medium is added to the flask to make up a total of 4 mls. The cells may be pipetted to dislodge or disperse the cells.

In the re-seeding step, the cells are re-seeded into fresh culture vessels and fresh medium added. A number of re-seedings may be made at different split ratios. For example, the cells may be reseeded at $1/15$ dilution and $1/5$ dilution. In a particular example, the cells may be re-seeded by adding 1 drop of cells into a 25 cm$^2$ flask and 3 drops into another to re-seed the culture, and 7-8 mls media is then added to each to provide for $1/15$ dilution and $1/5$ dilution from for example a 75 cm$^2$ flask. In the aliquoting step, the cells may be aliquoted into new dishes or whatever split ratio is desired, and media added.

Maintenance as Cell Culture

The disaggregated cells are plated and maintained as a cell culture.

The cells may be plated onto a culture vessel or substrate such as a gelatinized plate. Crucially, the cells are grown and propagated without the presence of co-culture, e.g., in the absence of feeder cells.

The cells in the cell culture are grown in a serum-free medium which is supplemented by one or more growth factors such as fibroblast growth factor 2 (FGF2) and optionally platelet-derived growth factor AB (PDGF AB), at for example 5 ng/ml. The cells in the cell culture are preferably split or subcultured 1:4 when confluent, by treatment with trypsin, washing and replating.

Absence of Co-Culture

In highly preferred embodiments, our methods involve culturing cells in the absence of co-culture. The term "co-culture" refers to a mixture of two or more different kinds of cells that are grown together, for example, stromal feeder cells.

Thus, in typical ES cell culture, the inner surface of the culture dish is usually coated with a feeder layer of mouse embryonic skin cells that have been treated so they will not divide. The feeder layer provides an adherent surface to enable the ES cells to attach and grow. In addition, the feeder cells release nutrients into the culture medium which are required for ES cell growth. In the methods and compositions described here, the ES and MSC cells are cultured in the absence of such co-culture.

Preferably, the cells are cultured as a monolayer or in the absence of feeder cells. According to preferred embodiments of the methods described here, the embryonic stem cells are cultured in the absence of feeder cells to establish mesenchymal stem cells (MSC).

In preferred embodiments, the dissociated or disaggregated embryonic stem cells are plated directly onto a culture substrate. The culture substrate may comprise a tissue culture vessel, such as a Petri dish. The vessel may be pre-treated. In preferred embodiments, the cells are plated onto, and grow on, a gelatinised tissue culture plate.

An example protocol for the gelatin coating of dishes follows. A solution of 0.1% gelatin in distilled water is made and autoclaved. This may be stored at room temp. The bottom of a tissue culture dish is covered with the gelatin solution and incubated for 5-15 min. Remove gelatin and plates are ready to use. Medium should be added before adding cells to prevent hypotonic lysis.

Serum Free Media

The dissociated or disaggregated embryonic stem cells are cultured in a medium which is preferably a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability allows for improved reproducibility and more consistent performance, and decreases possibility of contamination by adventitious agents.

In a preferred embodiment, the serum-free media comprises Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media is preferably supplemented with 10% serum replacement media from Invitrogen-Gibco (Grand Island, N.Y.).

Growth Factor

The serum-free medium in which the dissociated or disaggregated embryonic stem cells are cultured preferably comprises one or more growth factors. A number of growth factors are known in the art, including PDGF, EGF, TGF-a, FGF, NGF, Erythropoietin, TGF-b, IGF-I and IGF-II.

In a preferred embodiment, the growth factor comprises fibroblast growth factor 2 (FGF2). The medium may also contain other growth factors such as platelet-derived growth factor AB (PDGF AB). Both of these growth factors are known in the art. In a highly preferred embodiment, the method comprises culturing cells in a medium comprising both FGF2 and PDGF AB.

FGF2 is a wide-spectrum mitogenic, angiogenic, and neurotrophic factor that is expressed at low levels in many tissues and cell types and reaches high concentrations in brain and pituitary. FGF2 has been implicated in a multitude of physiologic and pathologic processes, including limb development, angiogenesis, wound healing, and tumor growth. FGF2 may be obtained commercially, for example from Invitrogen-Gibco (Grand Island, N.Y.).

Platelet Derived Growth Factor (PDGF) is a potent mitogen for a wide range of cell types including fibroblasts, smooth muscle and connective tissue. PDGF, which is composed of a dimer of two chains termed the A chain and B chain, can be present as AA or BB homodimers or as an AB heterodimer. Human PDGF-AB is a 25.5 kDa homodimer protein consisting of 13.3 kDa A chain and 12.2 B chain. PDGF AB may be obtained commercially, for example from Peprotech (Rocky Hill, N.J.).

The growth factor(s), preferably FGF2 and optionally PDGF AB, are preferably present in the medium at concentrations of about 100 pg/ml, preferably about 500 pg/ml, preferably about 1 ng/ml, preferably about 2 ng/ml, preferably about 3 ng/ml, preferably about 4 ng/ml, most preferably about 5 ng/ml. In preferred embodiments, the medium contains FGF2 at about 5 ng/ml. The medium may also contain PDGF AB, preferably at about 5 ng/ml.

Splitting Cells

Cells in culture will generally continue growing until confluence, when contact inhibition causes cessation of cell division and growth. Such cells may then be dissociated from the substrate or flask, and "split", subcultured or passaged, by dilution into tissue culture medium and replating.

The methods and compositions described here may therefore comprise passaging, or splitting during culture. Preferably, the cells in the cell culture are split at a ratio of 1:2 or more, preferably 1:3, more preferably 1:4, 1:5 or more. The term "passage" designates the process consisting in taking an aliquot of a confluent culture of a cell line, in inoculating into fresh medium, and in culturing the line until confluence or saturation is obtained.

Selection, Screening or Sorting Step

In highly preferred embodiments, the method further comprises a selection or sorting step, to further isolate or select for mesenchymal stem cells.

The selection or sorting step may comprise selecting mesenchymal stem cells (MSC) from the cell culture by means of one or more surface antigen markers. The use of a selection or sorting step further enhances the stringency of sorting and selection specificity for MSCs and furthermore potentially reduces possible contamination from embryonic stem cells such as hESCs and other hESC-derivatives from the starting material. This would then further reduce the risk of teratoma formation and further increase the clinical relevance of the protocol we describe.

A number of methods are known for selection or sorting based on antigen expression, and any of these may be used in the selection or sorting step described here. In particularly preferred embodiments, the selection or sorting is achieved by means of fluorescence activated cell sorting (FACS). Thus, as known in the art, FACS involves exposing cells to a reporter, such as a labelled antibody, which binds to and labels antigens expressed by the cell. Methods of production of antibodies and labelling thereof to form reporters are known in the art, and described for example in Harlow and Lane. The cells are then passed through a FACS machine, which sorts the cells from each other based on the labelling.

We have realised that while a number of candidate surface antigens known to be associated with MSCs e.g. CD105, CD73, ANPEP, ITGA4 (CD49d), PDGFRA, some of the MSC associated surface antigens e.g. CD29 and CD49e are also highly expressed in ES cells such as hESCs and their expression are verified by FACS analysis. The association of a surface antigen with MSCs may not be sufficient to qualify the antigen as a selectable marker for isolating MSCs from ES cells such as hESC. Accordingly, the selection or sorting step preferably employs antigens which are differentially expressed between MSCs and ES cells.

The selection or sorting step of our method may positively select for mesenchymal stem cells based on the expression of antigens. Such antigens may be identified by, for example, comparing the gene expression profiles of hESCs and hESC-MSCs as described in the Examples. In particular embodiments, the selection or sorting may specifically make use of any of the antigens shown in Table E1A and E1B below.

In preferred embodiments, the selection or sorting step of our method may positively select for mesenchymal stem cells based on the expression of antigens which are identified as expressed on MSCs, but not expressed on ES cells such as hESCs.

Figure 3A:
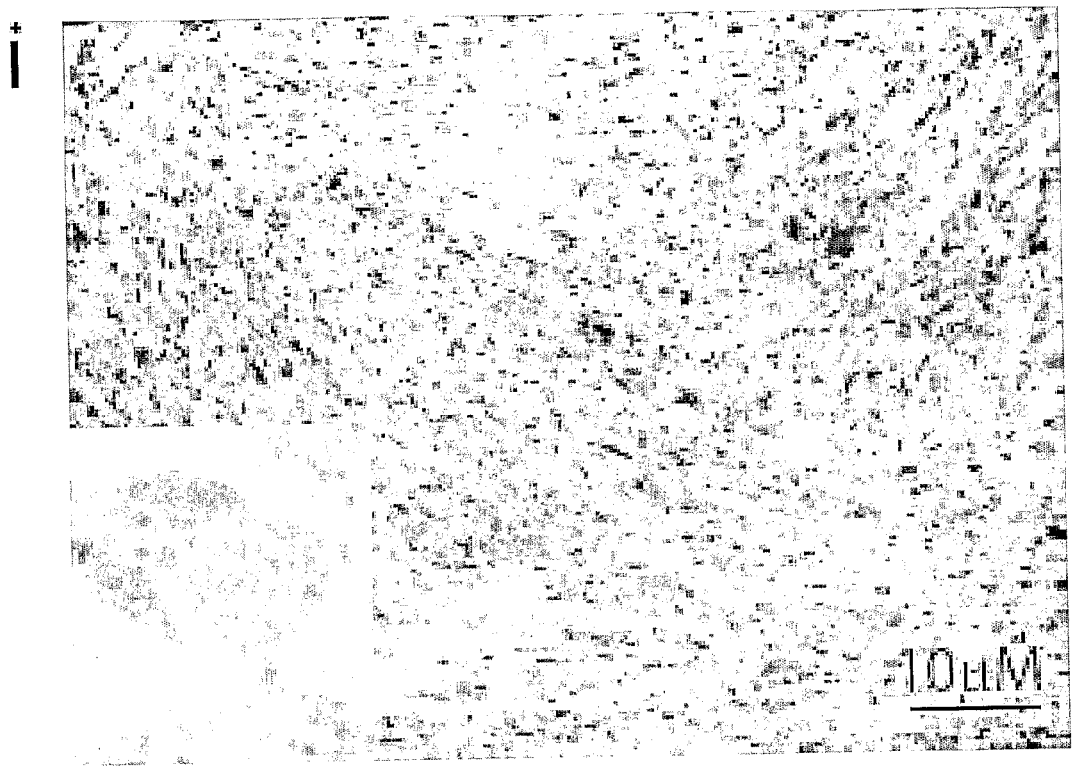
FIGS. 3A-3C. Differentiation of HuES9.E1. HuES9.E1 cells are induced to undergo adipogenesis, chondrogenesis and osteogenesis using standard protocols.
Figure 3A:
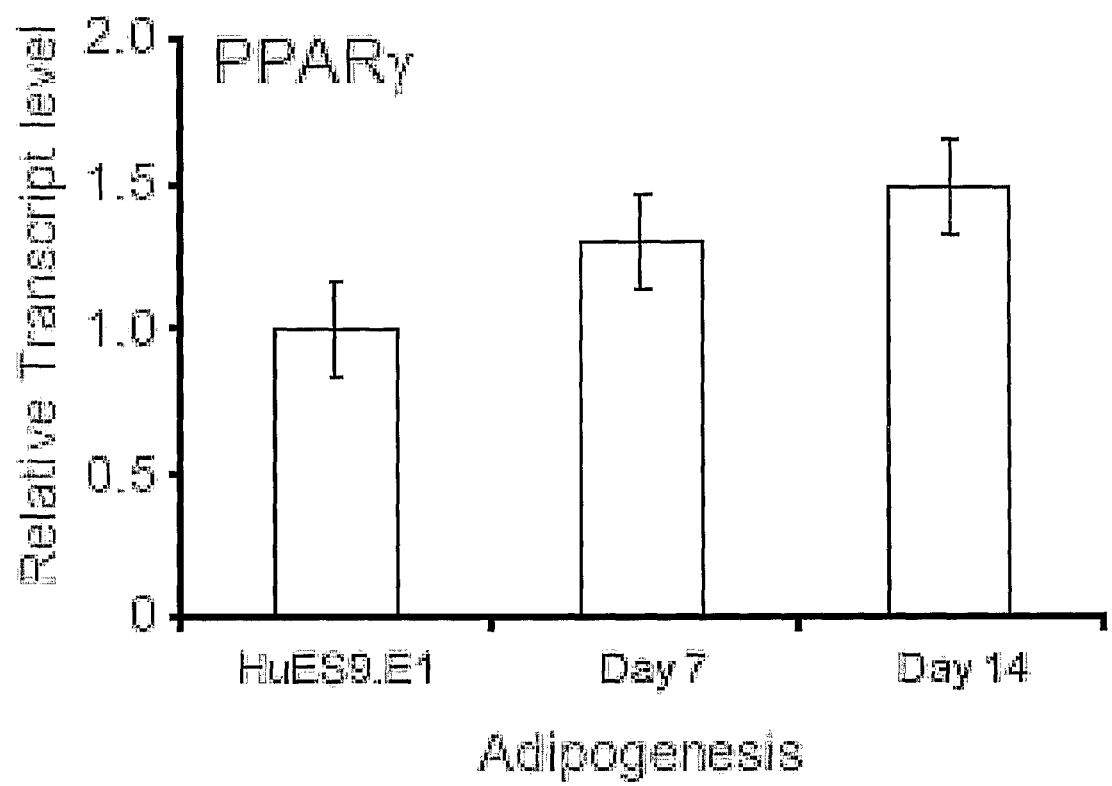
Figure 3A:
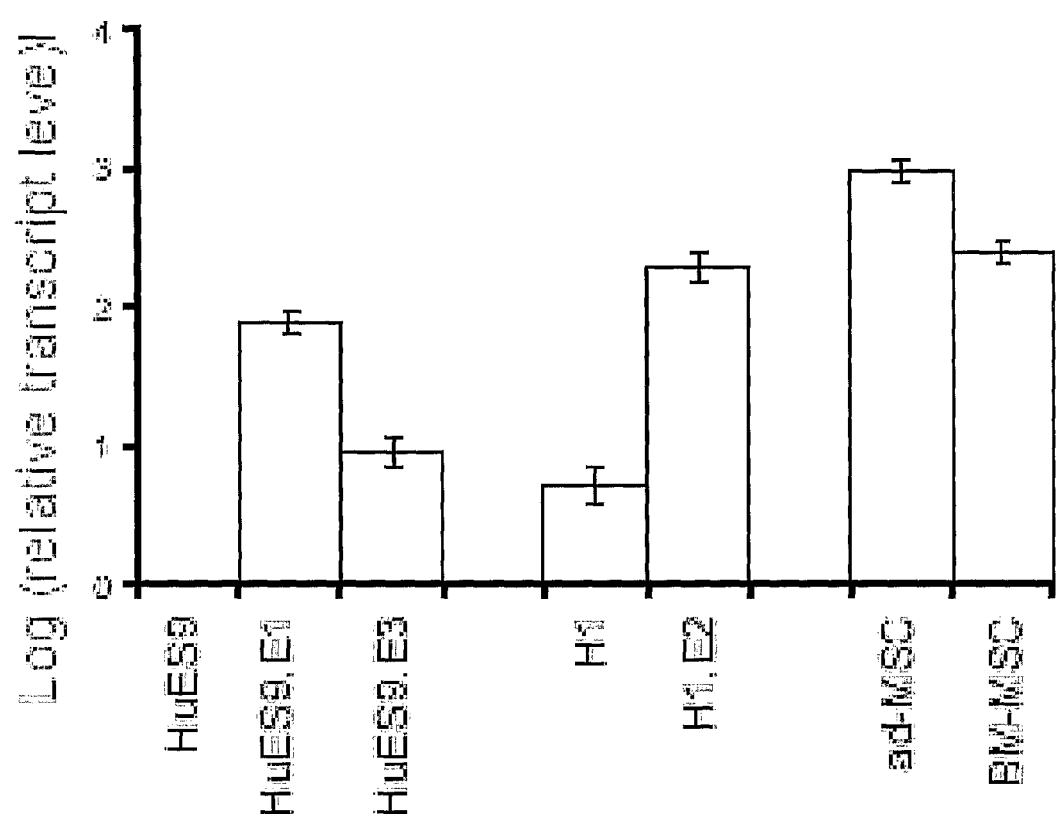
Figure 3B:
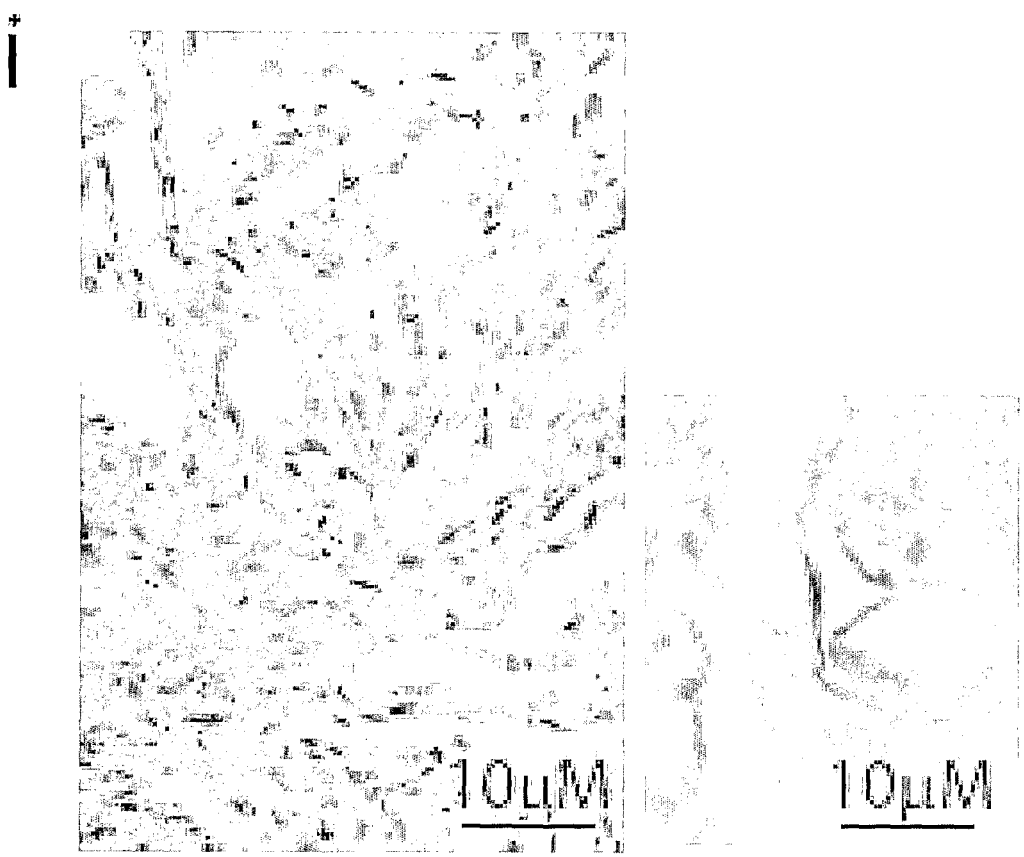
Figure 3B:
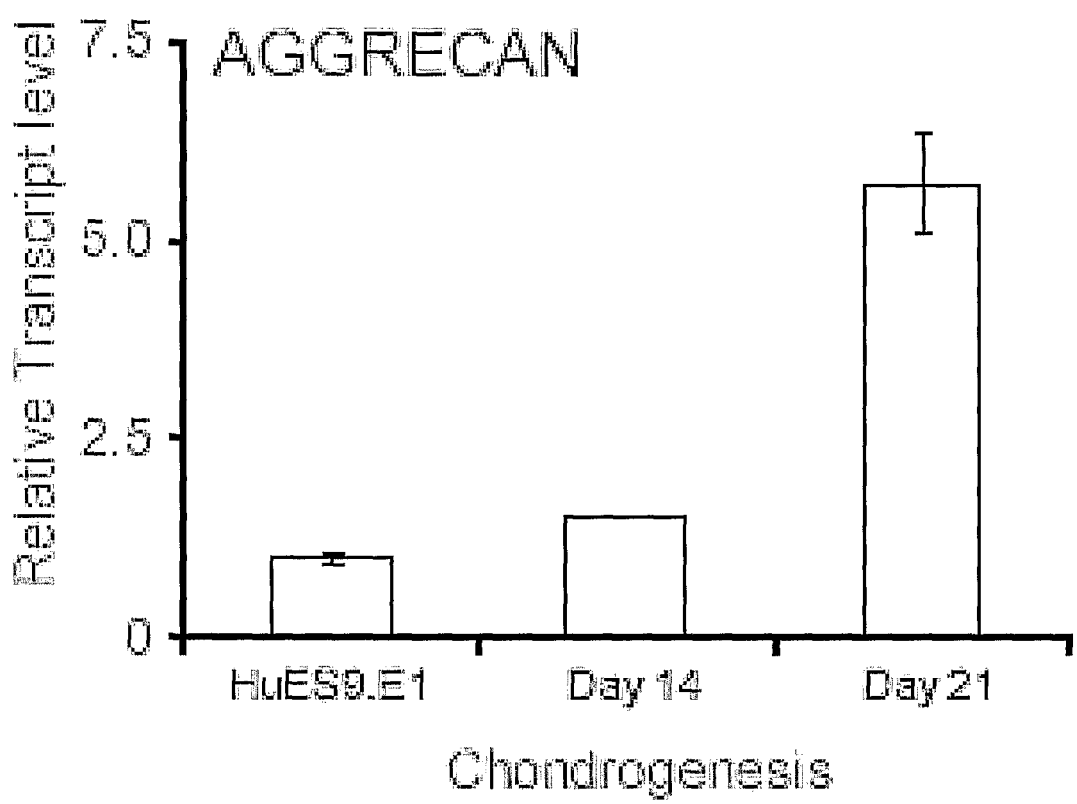
Figure 3B:
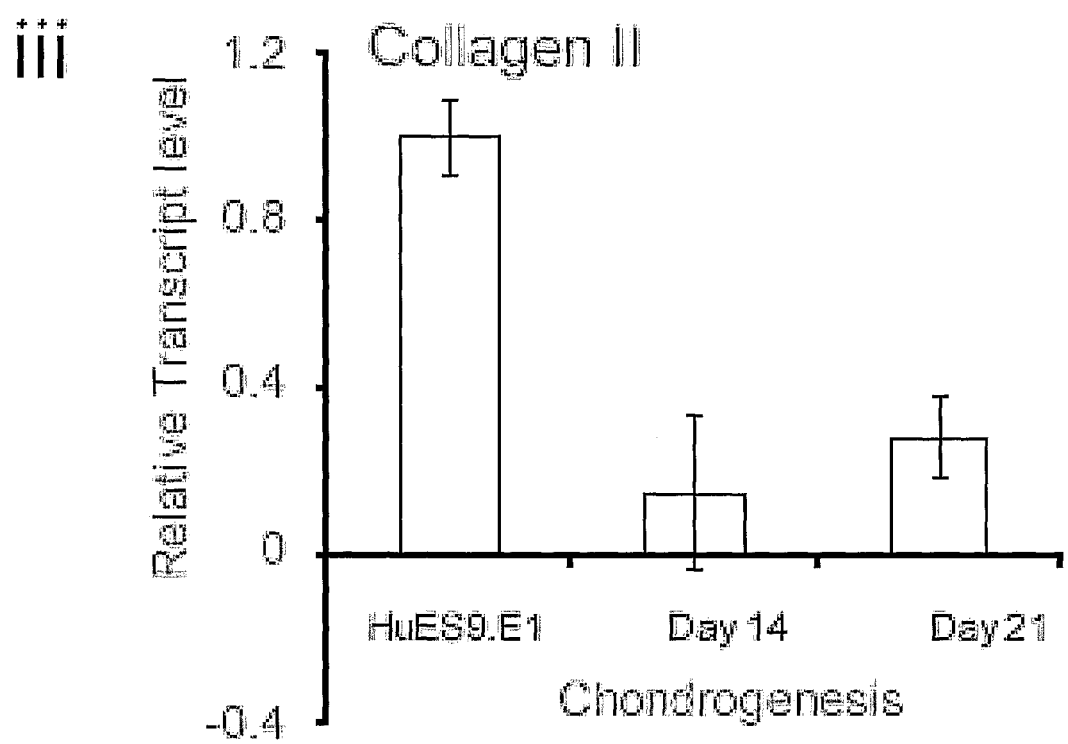
Figure 3C:
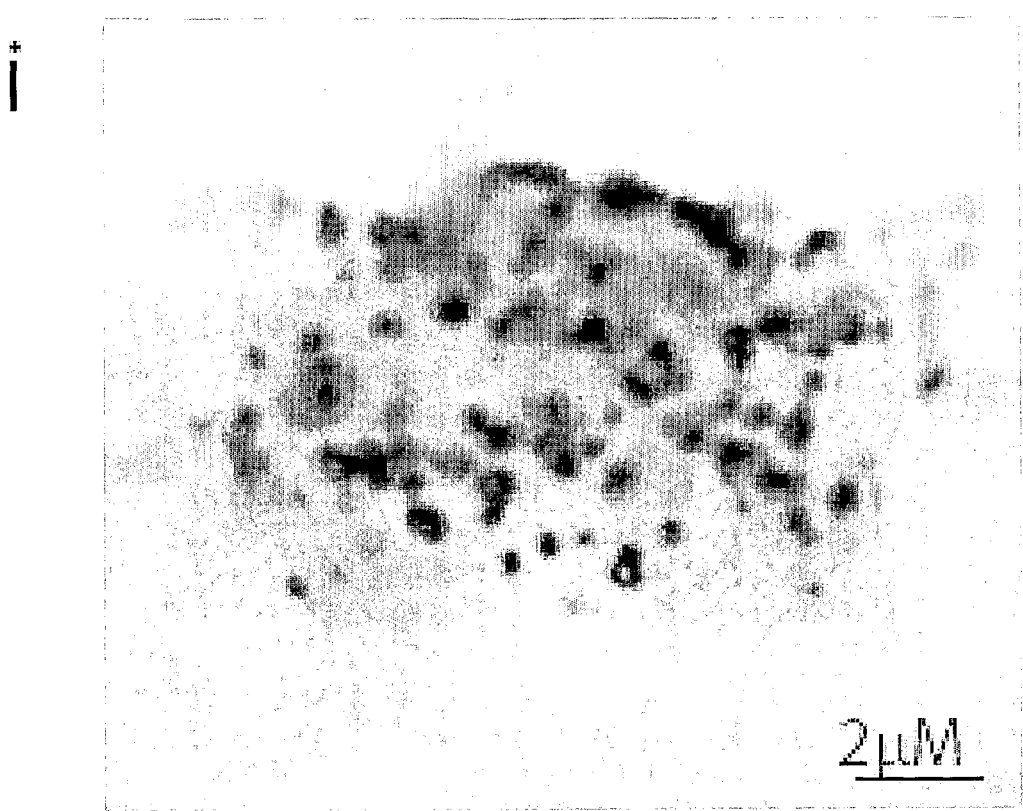
Figure 3C:
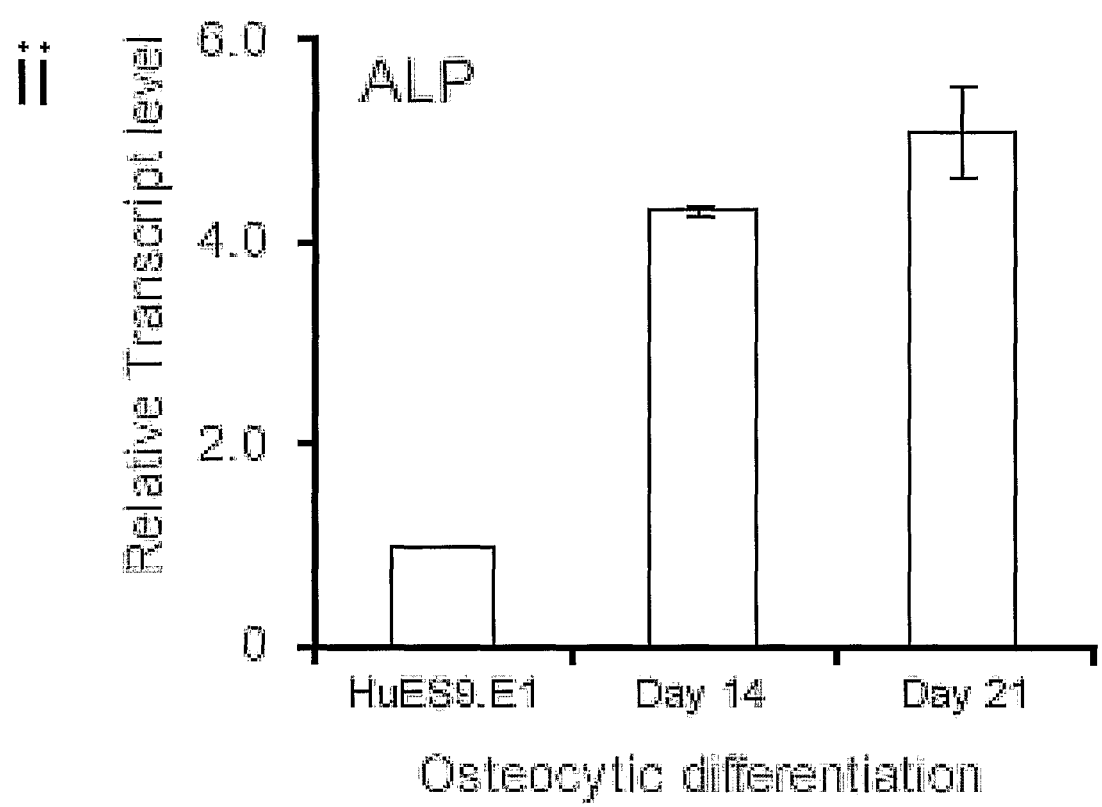
Figure 3C:
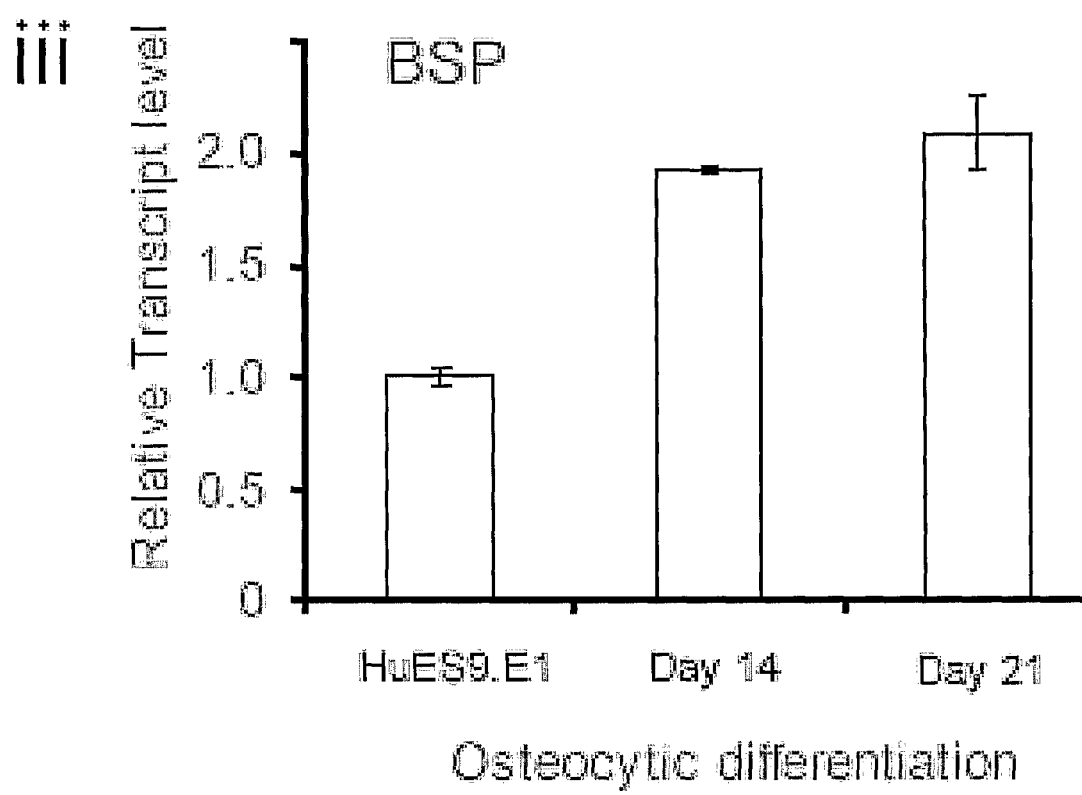
Figure 4A:
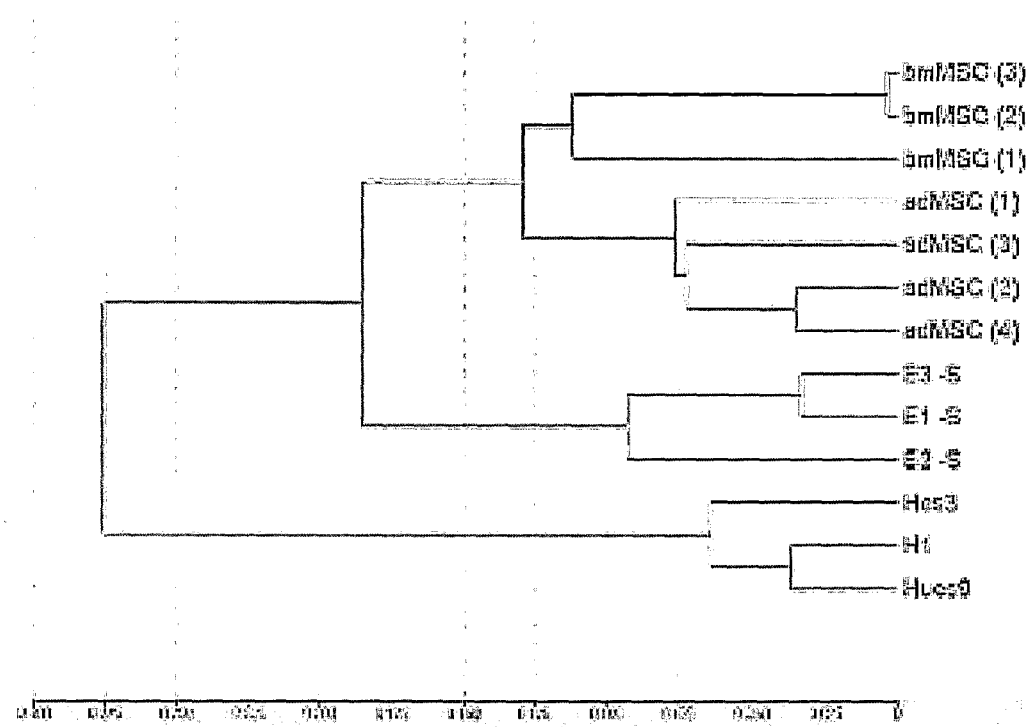
FIGS. 4A-4E. Gene expression analysis.

Thus, as shown in the Examples, we demonstrate that CD73 is highly expressed on MSCs[3], while being not highly expressed on hESCs (FIG. 4A). Furthermore, as the Examples demonstrate that both CD73 and CD105 are highly expressed surface antigens in MSCs and are among the top 20 highly expressed surface antigens in hESC-MSCs relative to hESC (FIG. 3, table), the use of either CD73 or CD105 (or both) as selectable marker for putative MSCs will be equally effective in sorting for putative MSCs generated by differentiating hESCs.

Alternatively, or in addition, the selection or sorting step may negatively select against antigens based on surface antigens that are highly expressed as surface antigen on embryonic stem cells (ES cells) such as hESCs, and not mesenchymal stem cells e.g., hESC-MSC. Selection or sorting may be based on known or previously identified hESC-specific surface antigens such as MIBP, ITGB1BP3 and PODXL[22], and CD24.

The Examples show that FACS analysis confirms the expression of CD24 on hESC but not hESC-MSCs. Therefore, CD24 may be used as a negative selection or sorting marker either on its own, or in conjunction with CD105 as a positive selectable marker for isolating putative MSCs from differentiating hESC cultures.

Importantly, the mesenchymal stem cells are able to maintain self-renewal without the requirement for transformation. Thus, for example, known transformation treatments such as fusion with immortalised cells such as tumour cells or tumour cell lines, viral infection of a cell line with transforming viruses such as SV40, EBV, HBV or HTLV-1, transfection with specially adapted vectors, such as the SV40 vector comprising a sequence of the large T antigen (R. D. Berry et al., Br. J. Cancer, 57, 287-289, 1988), telomerase (Bodnar-A-G. et.al., Science (1998) 279: p. 349-52) or a vector comprising DNA sequences of the human papillomavirus (U.S. Pat. No. 5,376,542), introduction of a dominant oncogene, or by mutation are therefore not required in the methods described here for making mesenchymal stem cells.

In preferred embodiments, the mesenchymal stem cells and cell lines (or the differentiated cells derived from them) do not display one or more characteristics of embryonic stem cells. Preferred such characteristics include expression of the OCT4 gene and alkaline phosphatase activity. Preferably, the mesenchymal stem cell exhibits reduced expression of one or more characteristic markers of pluripotency. Such pluripotency markers are described in further detail below, but include Nanog, BMP4, FGF5, Oct4, Sox-2 and Utf1.

Mesenchymal stem cells made by the methods described here are preferably non-tumorigenic. Preferably, the mesenchymal stem cells when implanted into an immune compromised or immunodeficient host animal do not result in tumours, compared to implantation of parental embryonic stem cells which results in tumour formation. Preferably, the immune compromised or immunodeficient host animal is a SCID mouse or a Rag1 −/− mouse. Preferably, the mesenchymal stem cells do not form tumours after prolonged periods of implantation, preferably greater than 2 weeks, more preferably greater than 2 months, most preferably greater than 9 months. Detailed protocols for tumourigenicity testing are set out in the Examples.

Mesenchymal stem cells made by the methods described here are also preferably display one or more of the following characteristics. They have a substantially stable karyotype as assessed by chromosome number, preferably when maintained in cell culture for at least 10 generations. They also preferably display a substantially stable gene expression pattern from generation to generation. By this we mean that the expression levels one or more, preferably substantially all, of a chosen set of genes does not vary significantly between a mesenchymal stem cells in one generation and mesenchymal stem cells in the next generation.

Preferably, the set of genes comprises one or more, a subset, or all of, the following: cerberus (GenBank Accession nos: NM_009887, AF031896, AF035579), FABP (GenBank Accession nos: NM_007980, M65034, AY523818, AY523819), Foxa2 (GenBank Accession nos: NM_010446, X74937, L10409), Gata-1 (GenBank Accession nos: NM_008089, X15763, BC052653), Gata-4 (GenBank Accession nos: NM_008092, AF179424, U85046, M98339, AB075549), Hesx1 (GenBank Accession nos: NM_010420, X80040, U40720, AK082831), HNF4a (GenBank Accession nos: NM_008261, D29015, BC039220), c-kit (GenBank Accession nos: NM_021099, Y00864, AY536430, BC075716, AK047010, BC026713, BC052457, AK046795), PDGFRα (NM_011058, M57683, M84607, BC053036), Oct4 (GenBank Accession nos: NM_013633, X52437, M34381, BC068268), Runx1 (GenBank Accession nos: NM_009821, D26532, BC069929, AK051758), Sox17 (GenBank Accession nos: NM_011441, D49474, L29085, AK004781), Sox2 (GenBank Accession nos: NM_011443, U31967, AB108673), Brachyury (NM_009309, X51683), TDGF1 (GenBank Accession nos: NM_011562, M87321) and Tie-2 (GenBank Accession nos: NM_013690, X67553, X71426, D13738, BC050824).

The methods described here enable the production of mesenchymal stem cells as well as differentiated cells, which comprise clonal descendants of mesenchymal stem cells. The term "clonal descendant" of a cell refers to descendants of the cells which have not undergone substantially any transforming treatment or genetic alteration. Such clonal descendants have not undergone substantial genomic changes are substantially genetically identical to the parent cell, or an ancestor, preferably, the embryonic stem cell (save with reduced potency). The term "mesenchymal stem cells" should also preferably be taken to include cell lines derived from mesenchymal stem cells, i.e., mesenchymal stem cell lines, and vice versa.

Derivation of Progenitor Cells

In preferred embodiments, the methods described here may employ further steps to select or screen for mesenchymal stem cells.

Such further steps may take place prior to the steps described above, in between such steps, or after these steps. The further steps may be in fact be conducted independently, and may specifically comprise deriving one or more progenitor cells or cell lines from the ES cells.

We therefore disclose an alternative method of deriving mesenchymal stem cells. The method comprises: (a) providing an embryonic stem (ES) cell; and (b) establishing a progenitor cell line from the embryonic stem cell; in which the progenitor cell line is selected based on its ability to self-renew.

However, preferably, the methods are conducted together. Thus, for example, our methods may comprise deriving progenitor cells or progenitor cell lines from the embryonic stem cell prior to, during, or after the dispersal step or the propagation step. Thus, the method may for example comprise obtaining a mesenchymal stem cell (MSC) by providing a cell obtained by dispersing a embryonic stem (ES) cell colony, or a descendent thereof, deriving one or more progenitor cells or progenitor cell lines from the embryonic stem cell and propagating the cell in the absence of co-culture in a serum free medium comprising FGF2.

Preferably, the progenitor cell line is selected based on its ability to self-renew, or the method may select against somatic cells based on their inability to self-renew, or both.

In a preferred embodiment, the progenitor cell line is derived or established in the absence of co-culture, preferably in the absence of feeder cells. Preferably, the absence of co-culture selects against embryonic stem cells.

In preferred embodiments, the progenitor cell line is established without transformation. The progenitor cell line may be established by exposing embryonic stem cells or their descendants to conditions which promote self-renewal of putative progenitor cells. Preferably, the self-renewal-promoting conditions discourage the propagation of embryonic stem cells.

The self-renewal-promoting conditions may comprise growth in rich media. More preferably, the self-renewal-promoting conditions comprise growing cells in the absence of LIF. Preferably, the self-renewal-promoting conditions comprise serial passages. Preferably, the self-renewal promoting conditions comprise at least 12 serial passages.

In preferred embodiments, the progenitor cell line has reduced potential compared to the embryonic stem cell. Preferably, the progenitor cell line is lineage restricted, preferably non-pluripotent. Preferably, the progenitor cell line is non-tumorigenic.

Preferably, the step of deriving the progenitor cell line comprises a step of exposing the embryonic stem cell to conditions that enhance differentiation to a specific lineage. Preferably, the differentiation enhancing-conditions comprises generating an embryoid body from the embryonic stem cell. Preferably, the cells are removed from differentiation enhancing-conditions after pluripotency is lost.

Preferably, the removing of the cells from lineage restriction-promoting conditions comprises disaggregating an embryoid body. Preferably, the method comprises disaggregating embryoid bodies which have been grown from between about 3 to 6 days.

In preferred embodiments, the progenitor cell line displays reduced expression of or does not substantially express either or both of OCT4 and alkaline phosphatase activity.

Preferably, the progenitor cell line displays reduced expression of a pluripotency marker compared to an embryonic stein cell from which it is derived, the pluripotency marker preferably selected from the group consisting of: Nanog, BMP4, FGF5, Oct4, Sox-2 and Utf1.

In preferred embodiments, the progenitor cell lines display one or more of the following characteristics: (a) are maintainable in cell culture for greater than 40 generations; (b) have a substantially stable karyotype or chromosome number when maintained in cell culture for at least 10 generations; (c) have a substantially stable gene expression pattern from generation to generation.

Preferably, the progenitor cell line does not substantially induce formation of teratoma when transplanted to a recipient animal, preferably an immune compromised recipient animal, preferably after 3 weeks, more preferably after 2 to 9 months.

Preferably, the embryonic stem cell or progenitor cell line is a mammalian, preferably mouse or human, embryonic stem cell or progenitor cell line.

Preferably, the progenitor cell line comprises an endothelial progenitor cell line, preferably a E-RoSH cell line. Alternatively, or in addition, the progenitor cell line may comprise a mesenchymal progenitor cell line, preferably a huES9.E1 cell line.

In some embodiments, the method further comprises the step of (d) deriving a differentiated cell from the progenitor cell line.

Preferably, the progenitor cell line is propagated for at least 5 generations prior to differentiation.

We provide a method of generating a differentiated cell from an embryonic stem (ES) cell, the method comprising: (a) deriving a progenitor cell line from the embryonic stem cell; (b) propagating the progenitor cell line; and (c) deriving a differentiated cell from the progenitor cell line.

There is provided a method comprising: (a) providing an embryonic stem (ES) cell; (b) deriving a progenitor cell from the embryonic stem cell; and (c) establishing a progenitor cell line from the progenitor cell, in which progenitor cells are selected based on their ability to self-renew.

The method may specifically be used for generating a differentiated cell from an embryonic stem (ES) cell. Preferably, the differentiated cell is an endothelial cell or a mesenchymal cell. More preferably, the differentiated cell is an adipocyte or an osteocyte.

We provide a progenitor cell line produced by a method according to any preceding aspect of the invention.

The methods and compositions described here may also further comprise further steps which employ other factors or characteristics of such MSCs for selection or screening or both.

Biasing Differentiation

In preferred embodiments, the method for generating embryonic stem cell-derived progenitor cell lines of specific lineages preferably further comprises a first step of biasing differentiation of embryonic stem cells towards a specific desired lineage or lineage of interest. Our methods may also comprise a second step of encouraging self-renewal of putative progenitor cells and discouraging the propagation of embryonic stem cells.

The first step may comprise promoting the growth or propagation of a specific lineage of interest. Different progenitor cell lines of specific lineages of interest may be made by exposing the cells to conditions that promote the differentiation of those lineages of interest. For example, the embryonic stem cells may be exposed to growth factors or small molecules such as ligands that promote or enable differentiation.

Thus, the methods described here for establishing embryonic stem cell-derived cell lines of specific lineages preferably include a step of enhancing differentiation of embryonic stem cells towards that specific lineage. Preferably, the differentiation-enhancing step is carried out for a predetermined period of time. Thus, preferably, the embryonic stem cells or their descendants are transiently exposed to differentiation-enhancing environment.

The choice of the method of enhancing or biasing differentiation will depend on the specific cell lineage of interest for which it is desired to produce progenitor cells. The person skilled in the art will be aware of the various methods which may be used for different cells.

Endodermal Progenitor Cells

Where it is desired to bias differentiation of embryonic stem cells towards endodermal types of tissues, for example, embryoid bodies may be formed and disaggregated (see later). The disaggregated embryoid bodies may be exposed to growth factors or drugs or combinations thereof that induce endodermal differentiation. Examples of such growth factors and drugs include activin A, FGF4, dexamethasone and retinoic acid.

Hematopoietic and Endothelial Progenitor Cells

On the other hand, where it is desired to bias differentiation of embryonic stem cells towards hematopoietic or endothelial lineages, the disaggregated embryoid bodies may be exposed to growth factors or drugs or combinations thereof that induce hematopoietic or endothelial differentiation. Examples of such growth factors and drugs include GM-CSF, G-CSF, SCF, PDGF, IL-3, erythropoietin, thrombopoeittin, TNFα and rapamycin.

Cardiac Mesoderm and Skeletal Myoblast Progenitor Cells

On the other hand, where it is desired to bias differentiation of embryonic stem cells towards cardiac mesoderm or skeletal myoblast lineages, the disaggregated embryoid bodies may be exposed to growth factors or drugs or combinations thereof that induce cardiac mesoderm or skeletal myoblast differentiation. Examples of such growth factors and drugs include dexamethasone, inhibitors of PPARγ and testosterone or its analogs.

The second step may comprise plating the differentiating cells in a rich media. In such embodiments, continued propagation will selectively enrich for progenitor cells which can then be cloned.

Formation of Embryoid Bodies

In some embodiments, the differentiation-enhancing step comprises formation of embryoid bodies from embryonic stem cells. Embryoid bodies, and methods for making them, are known in the art. The term "embryoid body" refers to spheroid colonies seen in culture produced by the growth of embryonic stem cells in suspension. Embryoid bodies are of mixed cell types, and the distribution and timing of the appearance of specific cell types corresponds to that observed within the embryo. Preferably, the embryoid bodies are generated by plating out embryonic stem cells onto semi-solid media, preferably methylcellulose media as described in Lim et al, Blood. 1997; 90:1291-1299. Preferably, the embryoid bodies are between 3 to 6 days old.

In such embodiments, the embryoid body is disaggregated, i.e., separating the component cells from each other, e.g., by collagenase or trypsin treatment, in order to remove the cells from lineage restriction-promoting conditions.

The method in preferred embodiments comprises a step of choosing a putative progenitor cell for the desired specific lineage. The choosing may be conducted based on morphology of the cell, or by expression or markers, etc. Gene expression profiling or antigen profiling may also be used to choose specific progenitor cells which are of a desired lineage. The chosen putative progenitor cell for the desired specific lineage may then be cultured, or further choosing steps conducted thereon.

In preferred embodiments, the differentiation-enhancing step is followed by exposing differentiating cells to conditions which encourage self-renewal of putative progenitor cells and discourage the propagation of embryonic stem cells. Such conditions may preferably comprise culture in the absence of co-culture or feeder cells (see above).

Rich Media

Alternatively, or in addition, such conditions comprise plating in rich media. The term "rich media" as used in this document is intended to refer to media which is nutrient rich. Preferably, such media comprises essential nutrients required for growth of the relevant cell. Preferably, the rich media contain serum. More preferably, it comprises substantially all the nutrients required for such growth. Most preferably, the rich medium supports, promotes and encourages growth of the relevant cells. in highly preferred embodiments, the relevant cell is a progenitor cell or a putative progenitor cell of interest. An example of a rich medium is DMEM with 4500 mg/l D-glucose, supplemented with 20% fetal calf serum, non essential amino acids, L-glutamine and β-mercaptoethanol.

In preferred embodiments, such rich media does not comprise additional growth regulators or hormones that allow, promote or encourage growth of embryonic stem cells, such as Leukemia Inhibitory Factor (LIF).

According to such embodiments, continued propagation will selectively enrich for progenitor cells which can then be cloned.

Long-Term Maintenance in Culture

Preferably, the methods described here involve culturing the embryonic stem cells or their descendants for more than one generation. Preferably, the cells are cultured for more than 5, more than 10, more than 15, more than 20, more than 25, more than 50, more than 40, more than 45, more than 50, more than 100, more than 200, more than 500 or more than 800 generations. In particular, the cell lines may be maintained for 1, 2, 3, 4, 5, 6, 7, 8, 9, 10, 11, 12, 13, 14, 15, 20, 25, 30, 35, 40, 45, 50, 75, 100, 200, 500 or more generations.

Cells in culture will generally continue growing until confluence, when contact inhibition causes cessation of cell division and growth. Such cells may then be dissociated from the substrate or flask, and "split" or passaged, by dilution into tissue culture medium and replating. The progenitor cells may therefore be passaged, or split during culture; preferably they are split at a ratio of 1:2 or more, preferably 1:3, more preferably 1:4, 1:5 or more. The term "passage" designates the process consisting in taking an aliquot of a confluent culture of a cell line, in inoculating into fresh medium, and in culturing the line until confluence or saturation is obtained.

The progenitor cells derived according to the methods described here may however be maintained for a large number of generations, based on their capacity to self-renew. On the other hand, it has been established that "normal" (i.e., untransformed somatic) cells derived directly from an organism are not immortal. In other words, such somatic cells have a limited life span in culture (they are mortal). They will not continue growing indefinitely, but will ultimately lose the ability to proliferate or divide after a certain number of generations. On reaching a "crisis phase" such cells die after about 50 generations. Thus, such somatic cells may only be passaged a limited number of times.

Importantly, the progenitor cells are able to maintain self-renewal without the requirement for transformation. Thus, for example, known transformation treatments such as fusion with immortalised cells such as tumour cells or tumour cell lines, viral infection of a cell line with tranforming viruses such as SV40, EBV, HBV or HTLV-1, transfection with specially adapted vectors, such as the SV40 vector comprising a sequence of the large T antigen (R. D. Berry et al., Br. J. Cancer, 57, 287-289, 1988), telomerase (Bodnar-A-G. et.al., Science (1998) 279: p. 349-52) or a vector comprising DNA sequences of the human papillomavirus (U.S. Pat. No. 5,376, 542), introduction of a dominant oncogene, or by mutation are therefore not required in the methods described here for making progenitor cell lines.

According to preferred embodiments of the methods described here, progenitor cells may be propagated without transformation for more than 50 generations. In preferred embodiments, the progenitor cells may be propagated indefinitely and without transformation as progenitor cell lines. The progenitor cells and progenitor cell lines are preferably lineage restricted compared to their parental embryonic stem cells. In particular, they are not capable of giving rise to all three germ layers. In highly preferred embodiments, the progenitor cell lines are preferably non-pluripotent.

Characteristics of Progenitor Cells

In preferred embodiments, the progenitor cells and cell lines (or the differentiated cells derived from them) do not display one or more characteristics of embryonic stem cells. Preferred such characteristics include expression of the OCT4 gene and alkaline phosphatase activity. Preferably, the progenitor cell line exhibits reduced expression of one or more characteristic markers of pluripotency. Such pluripotency markers are described in further detail below, but include Nanog, BMP4, FGF5, Oct4, Sox-2 and Utf1.

Progenitor cells made by the methods described here are preferably non-tumorigenic. Preferably, the progenitor cells when implanted into an immune compromised or immunodeficient host animal do not result in tumours, compared to implantation of parental embryonic stem cells which results in tumour formation. Preferably, the immune compromised or immunodeficient host animal is a SCID mouse or a Rag1 –/– mouse. Preferably, the progenitor cells do not form tumours after prolonged periods of implantation, preferably greater than 2 weeks, more preferably greater than 2 months, most preferably greater than 9 months. Detailed protocols for tumourigenicity testing are set out in the Examples.

Progenitor cells made by the methods described here are also preferably display one or more of the following characteristics. They have a substantially stable karyotype as assessed by chromosome number, preferably when maintained in cell culture for at least 10 generations. They also preferably display a substantially stable gene expression pattern from generation to generation. By this we mean that the expression levels one or more, preferably substantially all, of a chosen set of genes does not vary significantly between a progenitor cell in one generation and a progenitor cell in the next generation.

Preferably, the set of genes comprises one or more, a subset, or all of, the following: cerberus (GenBank Accession nos: NM_009887, AF031896, AF035579), FABP (GenBank Accession nos: NM_007980, M65034, AY523818, AY523819), Foxa2 (GenBank Accession nos: NM_010446, X74937, L10409), Gata-1 (GenBank Accession nos: NM_008089, X15763, BC052653), Gata-4 (GenBank Accession nos: NM_008092, AF179424, U85046, M98339, AB075549), Hesx1 (GenBank Accession nos: NM_010420, X80040, U40720, AK082831), HNF4a (GenBank Accession nos: NM_008261, D29015, BC039220), c-kit (GenBank Accession nos: NM_021099, Y00864, AY536430, BC075716, AK047010, BC026713, BC052457, AK046795), PDGFRα (NM_011058, M57683, M84607, BC053036), Oct4 (GenBank Accession nos: NM_013633, X52437, M34381, BC068268), Runx1 (GenBank Accession nos: NM_009821, D26532, BC069929, AK051758), Sox17 (GenBank Accession nos: NM_011441, D49474, L29085, AK004781), Sox2 (GenBank Accession nos: NM_011443, U31967, AB108673), Brachyury (NM_009309, X51683), TDGF1 (GenBank Accession nos: NM_011562, M87321) and Tie-2 (GenBank Accession nos: NM_013690, X67553, X71426, D13738, BC050824).

The methods described here enable the production of progenitor cells and progenitor cell lines as well as differentiated cells, which comprise clonal descendants of progenitor cells. The term "clonal descendant" of a cell refers to descendants of the cells which have not undergone substantially any transforming treatment or genetic alteration. Such clonal descendants have not undergone substantial genomic changes are substantially genetically identical to the parent cell, or an ancestor, preferably, the embryonic stem cell (save with reduced potency). The term "progenitor cell" should also preferably be taken to include cell lines derived from progenitor cells, i.e., progenitor cell lines, and vice versa.

Regulators of Self-Renewal and Differentiation

Our methods may also be used to identify putative regulators of self-renewal or differentiation. The methods involve conducting the methods described for production of progenitor cell lines or differentiated cells in the presence and absence of a candidate molecule, and identifying if the presence of the molecule has any effect on the process. For example, a molecule which accelerates the production of progenitor cells or differentiated cells may be used as a positive regulator of differentiation (or alternatively as an inhibitor of self-renewal). Conversely, a molecule which retards the process can be considered an inhibitor of differentiation or a promoter of self-renewal.

In preferred embodiments, we also provide a cell, preferably a progenitor, of a selected lineage, obtainable according to the method. Hitherto, preparations of progenitors were too impure for certainty as to whether any chosen cell was a progenitor cell. With culture according to the invention that can give rise to substantially 100% pure preparations of progenitors, isolation of a single progenitor is achieved.

We further provide in preferred embodiments a composition comprising a plurality of cells, wherein a majority of the cells are progenitor cells of a selected lineage. Preferably, at least 60% of the cells are progenitor cells of the selected lineage. More preferably, at least 60% of the cells are progenitor cells. In addition, the invention provides an isolated progenitor cell. The term cell line preferably refers to cells that can be maintained and grown in culture and display an immortal or indefinite life span.

The methods described here may be combined with decreasing the activity of mTOR to promote differentiation, as described in U.S. 60/609,216, herein incorporated by reference.

Uses of Progenitor Cells

Our methods are capable of producing of progenitor cells and cell lines of various types.

For example, we disclose a method of making peripheral blood progenitor cells (PBPC), neuronal progenitor cells, haematopoeitic progenitor cells, myeloid progenitor cells, epithelial progenitor cells, bone marrow stromal cells, skeletal muscle progenitor cells, pancreatic islet progenitor cells, mesenchymal progenitor cells, cardiac mesodermal stem cells, lung epithelial progenitor cells, liver progenitors, and endodermal progenitor cells.

Progenitor cells made according to the methods described here can be used for a variety of commercially important research, diagnostic, and therapeutic purposes. These uses are generally well known in the art, but will be described briefly here.

For example, stem cells may be used to generate progenitor cell populations for regenerative therapy. Progenitor cells may be made by ex vivo expansion or directly administered into a patient. They may also be used for the re-population of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Embryonic stem cells and their tissue stem cell derivatives may be used as sources of progenitor cells for the treatment of degenerative diseases such as diabetes, Alzheimer's disease, Parkinson's disease, etc. Stem cells, for example may be used as sources of progenitors for NK or dendritic cells for immunotherapy for cancer, which progenitors may be made by the methods and compositions described here.

It will be evident that the methods and compositions described here enable the production of progenitor cells, which may of course be made to differentiate using methods known in the art. Thus, any uses of differentiated cells will equally attach to those progenitor cells for which they are sources.

Progenitor cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

We therefore describe a method of treatment of a disease comprising: (a) providing an embryonic stem (ES) cell; (b) establishing a progenitor cell line from the embryonic stem cell in which the progenitor cell line is selected based on its ability to self-renew; (d) optionally deriving a differentiated cell from the progenitor cell line; and (e) administering the progenitor cell line or the differentiated cell into a patient.

Characteristics of Obtained MSCs

The MSCs obtained by the methods and compositions described here preferably satisfy the morphologic, phenotypic and functional criteria commonly used to identify MSCs[9], as known in the art. For ease of reference, the mesenchymal stem cells obtained by the methods and compositions described here, particularly as derived from human embroynic stem cells, may be referred to as "hESC-MSC"s.

Thus, the MSCs obtained by the methods and compositions described here may preferably exhibit one or more morphological characteristics of mesenchymal stem cells. For example, the MSCs obtained may form an adherent monolayer with a fibroblastic phenotype.

Furthermore, the MSCs obtained may preferably display a surface antigen profile which is similar or identical to mesenchymal stem cells. Thus, the surface antigen profile of the MSCs obtained may include one or more, preferably all, of CD29+, CD44+, CD49a and e+, CD105+, CD166+ and CD34−, CD45−[9-11].

The MSCs obtained may be differentiated into any mesenchymal lineage, using methods known in the art and described below. Thus, the MSCs obtained by the methods and compositions described here may display a differentiation potential that include adipogenesis, chondrogenesis and osteogenesis[9].

The mesenchymal stem cells obtained as described, e.g., hESC-MSCs, can have a substantial proliferative capacity in vitro. In some embodiments, the mesenchymal stem cells obtained may undergo at least 10 population doublings while maintaining a normal diploid karyotype. Preferably, however, the MSCs are capable of undergoing at least 20-30 population doublings while maintaining a normal diploid karyotype. In preferred embodiments, the MSCs display a stable gene expression and surface antigen profile throughout this time.

Preferably, the MSCs obtained do not display any defects, such as chromosomal aberrations and/or alterations in gene expression. In preferred embodiments, such defects are not evident until after 10 passages, preferably after 13 passages, more preferably after 15 passages.

hESC-MSC Proteome

The Examples describe experiments to analyse the proteome of human ESC-derived MSCs (hESC-MSCs).

As shown in Examples 7 to 15, the hESC-MSCs have an expression profile which is similar to that of adult bone marrow derived MSCs (BM-MSCs). These results demonstrate that the MSCs derived by our methods have significant biological similarities to their bone marrow derived counterparts, e.g., in their ability to secrete paracrine factors. Accordingly, the hESC-MSCs may be used for any purpose for which BM-MSCs are suitable.

We further provide a medium which is conditioned by culture of hESC-MSCs. Such a conditioned medium comprises molecules secreted by the hESC-MSC, including 201 unique gene products. Such a conditioned medium, and combinations of any of the molecules comprised therein, including in particular proteins or polypeptides, may be used to supplement the activity of, or in place of, the hESC-MSCs, for the purpose of for example treating or preventing a disease.

Analysis of the proteome of the hESC-MSCs shows that the proteins expressed are involved in three biological processes: metabolism, defense response, and tissue differentiation including vascularization, hematopoiesis and skeletal development. Accordingly, the hESC-MSCs may be used to treat diseases which these functions may have a role in, or whose repair or treatment involves any one or more of these biological processes. Similarly, the proteins expressed by the hESC-MSCs, singly or in combination, preferably in the form of a conditioned medium, may be used to supplement the activity of, or in place of, the hESC-MSCs, for the purpose of for example treating or preventing such diseases.

The 201 gene products expressed by the hESC-MSCs are shown to activate important signalling pathways in cardiovascular biology, bone development and hematopoiesis such as Jak-STAT, MAPK, Toll-like receptor, TGF-beta signalling and mTOR signaling pathways. Accordingly, the hESC-MSCs, proteins expressed by them, etc, may be used to prevent or treat a disease in which any of these signalling pathways is involved, or whose aetiology involves one or more defects in any one or more of these signalling pathways.

Furthermore, any one or more proteins secreted from the MSCs described here, including in the form of conditioned media, may be used for the same purposes as the BM-MSCs described herein.

The hESC-MSCs may also be used as sources for any of the proteins secreted or expressed by them, as listed in the in Examples 10 to 14, particularly the tables therein. We therefore provide for a method of producing a polypeptide as shown in any of Examples 10 to 14, the method comprising obtaining a mesenchymal stem cell as described, culturing the mesenchymal stem cell and isolating the polypeptide from the mesenchymal stem cell, preferably from a medium in which the mesenchymal stem cell is growing.

Homogeneity

In a preferred embodiment, the mesenchymal stem cells produced by the method described here are similar or identical (preferably homogenous) in nature. That is to say, mesenchymal stem cell (MSC) clones isolated by the protocol show a high degree of similarity or identity with each other, whether phenotypically or otherwise.

Similarity or identity may be gauged by a number of ways and measured by one or more characteristics. In a preferred embodiment, the clones are similar or identical in gene expression. Preferably, the method is such that any two or more mesenchymal stem cells selected by the method exhibit substantially identical or similar gene expression profiles, that is to say, a combination of the identity of genes expressed and the level to which they are expressed. Preferably, substantially all of the mesenchymal stem cells isolated exhibit substantially identical or similar gene expression profiles.

Homogeneity of gene expression may be measured by a number of methods. Preferably, genome-wide gene profiling is conducted using, for example, array hybridisation of extracted RNA as described in the Examples. Total RNA may be extracted and converted into cDNA, which is hybridised to an array chip comprising a plurality of gene sequences from a relevant genome. Preferably, the array comprises NCBI Reference Sequence (RefSeq) genes, which are well characterised genes validated, annotated and curated on an ongoing basis by National Center for Biotechnology Information (NCBI) staff and collaborators.

Gene expression between samples is then compared using analysis software. In a preferred embodiment, the similarity or identity of gene expression expressed as a "correlation coefficient". In such measures, a high correlation coefficient between two samples indicates a high degree of similarity between the pattern of gene expression in the two samples. Conversely, a low correlation coefficient between two samples indicates a low degree of similarity between the pattern of gene expression in the two samples. Normalisation may be conducted to remove systematic variations or bias (including intensity bias, spatial bias, plate bias and background bias) prior to data analysis.

Correlation tests are known in the art and include a T-test and Pearson's test, as described in for example Hill, T. & Lewicki, P. (2006). *Statistics: Methods and Applications*. StatSoft, Tulsa, Okla., ISBN: 1884233597 (also StatSoft, Inc. (2006). *Electronic Statistics Textbook*. Tulsa, Okla.: StatSoft. WEB: http://www.statsoft.com/textbook/stathome.html). Reference is made to Khojasteh et al., 2005, *A stepwise framework for the normalization of array CGH data*, BMC Bioinformatics 2005, 6:274. An Intra-class correlation coefficient (ICC) may also be conducted, as described in Khojasteh et al, supra.

In preferred embodiments, a Pearson's test is conducted to generate a Pearson's correlation coefficient. A correlation coefficient of 1.0 indicates an identical gene expression pattern.

In a preferred embodiment, the cDNA is hybridised to a Sentrix HumanRef-8 Expression BeadChip and scanned using a Illumina BeadStation 500x. Preferably, the data is extracted, normalised and analysed using Illumina BeadStudio (Illumina, Inc, San Diego, Calif., USA). It will be clear to the reader however that any suitable chip and scanning hardware and software (which outputs a correlation measurement) may be used to assay similarity of gene expression profile.

Preferably, the gene expression correlation coefficient between any two isolates as preferably measured by the above means is greater than 0.65, preferably greater than 0.70, more preferably greater than 0.80, more preferably greater than 0.85, more preferably greater than 0.90, most preferably more than 0.95.

In some embodiments, the method described here generates mesenchymal stem cells whose gene expression correlation coefficient between any two or more isolates of mesenchymal stem cells so obtained is in the same order as, or slightly less than, the correlation coefficient between technical replicates of the same RNA sample, performed a period of time apart such as 1 month apart. In other embodiments, the gene expression correlation coefficient between any two or more isolates of mesenchymal stem cells is greater than 0.90, preferably greater than 0.95.

Preferably, the gene expression correlation coefficients are in such ranges for cells which have undergone the selection or sorting procedure described above. Preferably, the gene expression correlation coefficient between the majority of isolates, preferably all isolates, is in such ranges.

Thus, as shown in the Examples, the correlation coefficient shows a high degree of similarity between five mesenchymal stem cell cultures obtained, with a correlation coefficient between four of the lines of 0.96 and the one with 0.90; in contrast, the correlation coefficient between technical replicates of a RNA sample analysed one month apart is between 0.97 and 0.98.

Accordingly, we provide for a method of generating mesenchymal stem cells which are substantially similar or identical (preferably homogenous) with each other. The isolates preferably display a near identical gene expression profile.

As well as the "internal" homogeneity described above (i.e., homogeneity between the isolates of MSCs from the method), homogeneity may also be assessed between such isolates and other cells or cell types. In particular, comparisons may be made with mesenchymal stem cells derived by other methods, such as bone-marrow derived mesenchymal stem cells (BM-MSCs). In preferred embodiments, the MSCs obtained by the methods and compositions described here display a gene expression profile which is similar to, homogenous with, or identical with a BM-MSC. Thus, the MSCs obtained may show a correlation coefficient of gene expression of greater than 0.5, preferably greater than 0.6, preferably greater than 0.7, with BM-MSCs.

Thus, as shown in the Examples, pairwise comparision of gene expression between three independently derived hESC-MSC populations and three individual BM-MSC samples are found to be similar with a correlation coefficient of 0.72.

Regulators of Mesenchymal Stem Cell Formation

Our methods may also be used to identify putative regulators of mesenchymal stem cell formation from embryonic stem cells. The methods involve conducting the methods described for production of mesenchymal stem cells in the presence and absence of a candidate molecule, and identifying if the presence of the molecule has any effect on the process. For example, a molecule which accelerates the production of mesenchymal stem cells may be used as a positive regulator of mesenchymal stem cell formation. Conversely, a molecule which retards the process can be considered an inhibitor of mesenchymal stem cell formation.

In preferred embodiments, we also provide a cell, preferably a mesenchymal stem cell, obtainable according to the method. Hitherto, preparations of mesenchymal stem cells were either too impure, or not substantially phenotypically similar or identical (e.g., with respect to gene expression), or were not suitable for clinical purposes as they are produced by methods involving co-culture or presence of serum. With culture according to the invention, this can give rise to substantially 100% pure preparations of mesenchymal stem cells which are similar or identical (preferably homogenous) to each other.

In addition, we describe a process for producing differentiated cells, the method comprising obtaining a mesenchymal stem cell by a method as described herein, and differentiating the mesenchymal stem cell. For example, we provide for methods of differentiating to adipocytes, chondrocytes and osteocytes, etc. We further provide differentiated cells obtainable by such methods. Cell lines made from such mesenchymal stem cells and differentiated cells are also provided. The term cell line preferably refers to cells that can be maintained and grown in culture and display an immortal or indefinite life span.

The methods described here may be combined with decreasing the activity of mTOR to promote differentiation, as described in U.S. 60/609,216, herein incorporated by reference.

Uses

The methods and compositions described here may be used for up-regulating expression of mesenchymal or endothelial markers of a cell. They may also or instead be used for down-regulating expression of stem cell or pluripotency markers of a cell. The methods and compositions described here may be used to identify an agent capable of promoting or retarding self-renewal or differentiation of a stem cell. Such a method comprises performing a method according to any preceding claim in the presence of a candidate molecule, and determining an effect thereon.

The methods and compositions described here may also be used for the production of a progenitor cell line or a differentiated cell for the treatment of, or the preparation of a pharmaceutical composition for the treatment of, any one of the following: a disease treatable by regenerative therapy, cardiac failure, bone marrow disease, skin disease, burns, degenerative disease such as diabetes, Alzheimer's disease, Parkinson's disease and cancer.

Mesenchymal stem cells and differentiated cells made according to the methods described here can be used for a variety of commercially important research, diagnostic, and therapeutic purposes. These uses are generally well known in the art, but will be described briefly here.

For example, stem cells may be used to generate mesenchymal stem cells and differentiated cell populations for regenerative therapy. Mesenchymal stem cells and differentiated cells may be made by ex vivo expansion or directly administered into a patient. They may also be used for the re-population of damaged tissue following trauma.

Thus, adipocytes or fat tissues may therefrom may be used to fill up cavities or depressions during reconstructive or plastic surgery. Chondrocytes may be used for cartilage repair while osteocytes may be used for bone repair. The mesenchymal stem cells made by the methods and compositions described here may be differentiated into any of these cell types and used for the purposes described.

Embryonic stem cells and their tissue stem cell derivatives may be used as sources of mesenchymal stem cells and differentiated cells for the treatment of degenerative diseases such as diabetes, Alzheimer's disease, Parkinson's disease, etc. Stem cells, for example may be used as sources of mesenchymal stem cells and differentiated cells for NK or dendritic cells for immunotherapy for cancer, which mesenchymal stem cells and differentiated cells may be made by the methods and compositions described here.

It will be evident that the methods and compositions described here enable the production of mesenchymal stem cells, which may of course be made to differentiate using methods known in the art. Thus, any uses of differentiated cells will equally attach to those mesenchymal stem cells for which they are sources.

Mesenchymal stem cells and differentiated cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

We therefore describe a method of treatment of a disease comprising: (a) providing an embryonic stem (ES) cell; (b) establishing a mesenchymal stem cell line from the embryonic stem cell in which the mesenchymal stem cell is obtained by dispersing a embryonic stem (ES) cell colony, or a descendent thereof, and propagating the cell in the absence of co-culture in a serum free medium comprising FGF2; (d) optionally deriving a differentiated cell from the mesenchymal stem cell line; and (e) administering the mesenchymal stem cell line or the differentiated cell into a patient. The medium may optionally contain PDGF AB.

Our methods may generally be used for up-regulating expression of mesenchymal or endothelial markers of a cell.

Alternatively, or in addition, they may be used for down-regulating expression of stem cell or pluripotency markers of a cell.

We further provide a method according to any preceding aspect of the invention for the production of a progenitor cell line or a differentiated cell for the treatment of, or the preparation of a pharmaceutical composition for the treatment of, any one of the following: a disease treatable by regenerative therapy, cardiac failure, bone marrow disease, skin disease, burns, degenerative disease such as diabetes, Alzheimer's disease, Parkinson's disease and cancer.

We also provide a differentiated cell produced by a method according to any preceding aspect of the invention.

Differentiated Cells

Differentiated cells, such as terminally differentiated cells, may be derived from the mesenchymal stem cells or cell lines made according to the methods described. We therefore disclose methods for generating differentiated cells, the methods comprising generating mesenchymal stem cells or cell lines as described, and deriving differentiated cells from these. The mesenchymal stem cells made by the methods and compositions described here may be differentiated into any of these cell types and used for the purposes described.

Differentiated cells which may be made according to the methods described here may include any or all of the following:

i) adipocyte: the functional cell type of fat, or adipose tissue, that is found throughout the body, particularly under the skin. Adipocytes store and synthesize fat for energy, thermal regulation and cushioning against mechanical shock ii) cardiomyocytes: the functional muscle cell type of the heart that allows it to beat continuously and rhythmically iii) chondrocyte: the functional cell type that makes cartilage for joints, ear canals, trachea, epiglottis, larynx, the discs between vertebrae and the ends of ribs iv) fibroblast: a connective or support cell found within most tissues of the body. Fibroblasts provide an instructive support scaffold to help the functional cell types of a specific organ perform correctly.

v) hepatocyte: the functional cell type of the liver that makes enzymes for detoxifying metabolic waste, destroying red blood cells and reclaiming their constituents, and the synthesis of proteins for the blood plasma vi) hematopoietic cell: the functional cell type that makes blood. Hematopoietic cells are found within the bone marrow of adults. In the fetus, hematopoietic cells are found within the liver, spleen, bone marrow and support tissues surrounding the fetus in the womb.

vii) myocyte: the functional cell type of muscles viii) neuron: the functional cell type of the brain that is specialized in conducting impulses ix) osteoblast: the functional cell type responsible for making bone x) islet cell: the functional cell of the pancreas that is responsible for secreting insulin, glucogon, gastrin and somatostatin. Together, these molecules regulate a number of processes including carbohydrate and fat metabolism, blood glucose levels and acid secretions into the stomach.

Uses of Mesenchymal Stem Cells and Differentiated Cells

Mesenchymal stem cells and differentiated cells made according to the methods and compositions described here may be used for a variety of commercially important research, diagnostic, and therapeutic purposes.

For example, populations of differentiated cells may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

These and other uses of mesenchymal stem cells and differentiated cells are described in further detail below, and elsewhere in this document. The mesenchymal stem cells and differentiated cells may in particular be used for the preparation of a pharmaceutical composition for the treatment of disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

As shown in the Examples, the mesenchymal stem cells made by the methods and compositions described here have similar or identical properties to bone marrow derived mesenchymal stem cells (BM-MSCs). Therefore, the mesenchymal stem cells, and any differentiated cells made from these, may be used in any of the applications for which BM-MSCs are known to be used, or in which it is possible for them to be used.

Drug Screening

Mesenchymal stem cells and differentiated cells made according to the methods and compositions described here may also be used to screen for factors (such as solvents, small molecule drugs, peptides, polynucleotides, and the like) or environmental conditions (such as culture conditions or manipulation) that affect the characteristics of mesenchymal stem cells or differentiated cells.

In some applications, mesenchymal stem cells and differentiated cells are used to screen factors that promote maturation, or promote proliferation and maintenance of such cells in long-term culture. For example, candidate maturation factors or growth factors are tested by adding them to mesenchymal stem cells or differentiated cells in different wells, and then determining any phenotypic change that results, according to desirable criteria for further culture and use of the cells.

Furthermore, gene expression profiling of mesenchymal stem cells and differentiated cells may be used to identify receptors, transcription factors, and signaling molecules that are unique or highly expressed in these cells. Specific ligands, small molecule inhibitors or activators for the receptors, transcription factors and signaling molecules may be used to modulate differentiation and properties of mesenchymal stem cells and differentiated cells.

Particular screening applications relate to the testing of pharmaceutical compounds in drug research. The reader is referred generally to the standard textbook "In vitro Methods in Pharmaceutical Research", Academic Press, 1997, and U.S. Pat. No. 5,030,015), as well as the general description of drug screens elsewhere in this document. Assessment of the activity of candidate pharmaceutical compounds generally involves combining the differentiated cells with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug—drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Tissue Regeneration

Mesenchymal stem cells and differentiated cells made according to the methods and compositions described here may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells. Mesenchymal stem cells and differentiated cells may be used for tissue engineering, such as for the growing of skin grafts. Modulation of stem cell differentiation may be used for the bioengineering of artificial organs or tissues, or for prosthetics, such as stents.

Cancer

Mesenchymal stem cells and differentiated cells made by the methods and compositions described here may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

The mesenchymal stem cells and differentiated cells made according to the methods and compositions described here may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino)benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Stem Cells

As used in this document, the term "stem cell" refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells.

Totipotent Stem Cells

The term "totipotent" cell refers to a cell which has the potential to become any cell type in the adult body, or any cell of the extraembryonic membranes (e.g., placenta). Thus, the only totipotent cells are the fertilized egg and the first 4 or so cells produced by its cleavage.

Pluripotent Stem Cells

"Pluripotent stem cells" are true stem cells, with the potential to make any differentiated cell in the body. However, they cannot contribute to making the extraembryonic membranes which are derived from the trophoblast. Several types of pluripotent stem cells have been found.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

Sources of Stem Cells

Stem cells of various types, which may include the following non-limiting examples, may be used in the methods and compositions described here for producing mesenchymal stem cells and differentiated cells.

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Primary liver cell cultures can be obtained from human biopsy or surgically excised tissue by perfusion with an appropriate combination of collagenase and hyaluronidase. Alternatively, EP 0 953 633 A1 reports isolating liver cells by preparing minced human liver tissue, resuspending concentrated tissue cells in a growth medium and expanding the cells in culture. The growth medium comprises glucose, insulin, transferrin, $T_3$, FCS, and various tissue extracts that allow the hepatocytes to grow without malignant transformation. The cells in the liver are thought to contain specialized cells including liver parenchymal cells, Kupffer cells, sinusoidal endothelium, and bile duct epithelium, and also precursor cells (referred to as "hepatoblasts" or "oval cells") that have the capacity to differentiate into both mature hepatocytes or biliary epithelial cells (L. E. Rogler, Am. J. Pathol. 150:591, 1997; M. Alison, Current Opin. Cell Biol. 10:710, 1998; Lazaro et al., Cancer Res. 58:514, 1998).

U.S. Pat. No. 5,192,553 reports methods for isolating human neonatal or fetal hematopoietic stem or progenitor cells. U.S. Pat. No. 5,716,827 reports human hematopoietic cells that are Thy-1 positive progenitors, and appropriate growth media to regenerate them in vitro. U.S. Pat. No. 5,635,387 reports a method and device for culturing human hematopoietic cells and their precursors. U.S. Pat. No. 6,015,554 describes a method of reconstituting human lymphoid and dendritic cells.

U.S. Pat. No. 5,486,359 reports homogeneous populations of human mesenchymal stem cells that can differentiate into cells of more than one connective tissue type, such as bone, cartilage, tendon, ligament, and dermis. They are obtained from bone marrow or periosteum. Also reported are culture conditions used to expand mesenchymal stem cells. WO 99/01145 reports human mesenchymal stem cells isolated from peripheral blood of individuals treated with growth factors such as G-CSF or GM-CSF. WO 00/53795 reports adipose-derived stem cells and lattices, substantially free of adipocytes and red cells. These cells reportedly can be expanded and cultured to produce hormones and conditioned culture media.

Stem cells of any vertebrate species can be used. Included are stem cells from humans; as well as non-human primates, domestic animals, livestock, and other non-human mammals such as rodents, mice, rats, etc.

Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells.

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco#11965-092; Knockout Dulbecco's modified Eagles medium (KO DMEM), Gibco#10829-018; 200 mM L-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

In a preferred embodiment, the media comprises Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) are propagated in mEF medium, containing 90% DMEM (Gibco#11965-092), 10% FBS (Hyclone#30071-03), and 2 mM glutamine. mEFs are propagated in T150 flasks (Coming#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (.about.4000 rads gamma irradiation). Six-well culture plates (such as Falcon#304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Embryonic Stem Cells

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated. embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (.about.200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 $mm^3$ chunks. The tissue is then pipetted through a 100/µL tip to further disaggregate the cells. It is incubated at 37 degrees C. for about 5 min, then about 3.5 mL EG growth medium is added. EG growth medium is DMEM, 4500 mg/L D-glucose, 2200 mg/L mM sodium bicarbonate; 15% embryonic stem (ES) qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 µM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37 degrees C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad y-irradiation. Suitable feeders are STO cells (ATCC Accession No. CRL 1503). 0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Self-Renewal and Differentiation

Self-Renewal

Stem cells which are self-renewing may be identified by various means known in the art, for example, morphology, immunohistochemistry, molecular biology, etc.

Such stem cells preferably display increased expression of Oct4 and/or SSEA-1. Preferably, expression of any one or more of Flk-1, Tie-2 and c-kit is decreased. Stem cells which are self-renewing preferably display a shortened cell cycle compared to stem cells which are not self-renewing.

For example, in the two dimensions of a standard microscopic image, human embryonic stem cells display high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes.

Human embryonic stem and human embryonic germ cells may also be characterized by expressed cell markers. In general, the tissue-specific markers discussed in this disclosure can be detected using a suitable immunological technique—such as flow cytometry for membrane-bound markers, immunohistochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Linesfrom Human Gern Cell Tumors, in E. J. Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Differentiation

Differentiating cells, including mesenchymal stem cells and differentiated cells derived from these, preferably display enhanced dephosphorylation of 4E-BP1 and/or S6K1. They preferably display decreased expression of Oct4 and/or SSEA-1. Preferably, expression of any one or more of Flk-1, Tie-2 and c-kit is increased. Preferably, expression of any one or more of Brachyury, AFP, nestin and nurr1 expression increased. Stem cells which are self-renewing preferably display a lenghtened cell cycle compared to stem cells which are not self-renewing.

Differentiating stem cells, i.e., cells which have started to, or are committed to a pathway of differentiation can be characterized according to a number of phenotypic criteria, including in particular transcript changes. The criteria include but are not limited to characterization of morphological features, detection or quantitation of expressed cell markers and enzymatic activity, gene expression and determination of the functional properties of the cells in vivo. In general, differentiating stem cells will have one or more features of the cell type which is the final product of the differentiation process, i.e., the differentiated cell. For example, if the target cell type is a muscle cell, a stem cell which is in the process of differentiating to such a cell will have for example a feature of myosin expression.

In many respects, therefore, the criteria will depend on the fate of the differentiating stem cell, and a general description of various cell types is provided below.

Markers of interest for differentiated or differentiating neural cells include beta-tubulin EIII or neurofilament, characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated human embryonic stem cells; nestin, characteristic of neural precursors and other cells. A2B5 and NCAM are characteristic of glial progenitors and neural progenitors, respectively. Cells can also be tested for secretion of characteristic biologically active substances. For example, GABA-secreting neurons can be identified by production of glutamic acid decarboxylase or GABA. Dopaminergic neurons can be identified by production of dopa decarboxylase, dopamine, or tyrosine hydroxylase.

Markers of interest for differentiated or differentiating liver cells include alpha-fetoprotein (liver progenitors); albumin, $\alpha_1$-antitrypsin, glucose-6-phosphatase, cytochrome p450 activity, transferrin, asialoglycoprotein receptor, and glycogen storage (hepatocytes); CK7, CK19, and gamma-glutamyl transferase (bile epithelium). It has been reported that hepatocyte differentiation requires the transcription factor BNF-4 alpha (Li et al., Genes Dev. 14:464, 2000). Markers independent of HNF-4 alpha expression include alpha$_1$-antitrypsin, alpha-fetoprotein, apoe, glucokinase, insulin growth factors 1 and 2, IGF-1 receptor, insulin receptor, and leptin. Markers dependent on HNF-4 alpha expression include albumin, apoAI, apoAII, apoB, apoCIII, apoCII, aldolase B, phenylalanine hydroxylase, L-type fatty acid binding protein, transferrin, retinol binding protein, and erythropoietin (EPO).

Cell types in mixed cell populations derived from pPS cells can be recognized by characteristic morphology and the markers they express. For skeletal muscle: myoD, myogenin, and myf-5. For endothelial cells: PECAM (platelet endothelial cell adhesion molecule), Flk-1, tie-i, tie-2, vascular endothelial (VE) cadherin, MECA-32, and MEC-14.7. For smooth muscle cells: specific myosin heavy chain. For cardiomyocytes: GATA-4, Nkx2.5, cardiac troponin I, alpha-myosin heavy chain, and ANF. For pancreatic cells, pdx and insulin secretion. For hematopoietic cells and their progenitors: GATA-1, CD34, AC133, β-major globulin, and β-major globulin like gene PH1.

Certain tissue-specific markers listed in this disclosure or known in the art can be detected by immunological techniques—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez).

EXAMPLES

Example 1

Methods

Derivation of hESC-MSC (Mesenchymal Stem Cells)

Hues9 and H1 hESCs are grown as previously described[6,7].

To differentiate hESCs, a confluent 6 cm plate of hESCs is trypsinized for 3 mins, 37° C., neutralized, centrifuged and resuspended in Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.), and 5 ng/ml PDGF AB (Peprotech, Rocky Hill, N.J.) on a gelatinized 10 cm plate. The cells are trypsinized when confluent and split 1:4.

Sorting for CD105+ and CD24− is performed one week after hESCs have been trypsinized. The differentiating hESCs are trypsinized for 3 mins, neutralized, centrifuged, resuspended in the culture media and then plated on bacterial culture dish. After 2 hours at 37° C. in $CO^2$ incubator, the cells are harvested, washed with PBS and incubated with CD24-PE and CD105-FITC (PharMingen, San Diego, Calif.) for 90 mins at room temperature.

The cells are then washed with PBS and sorted on a FACS Aria using FACS Diva software (BD Biosciences Pharmingen, San Diego, Calif.). BM MSCs are prepared as previously described[26]. The cells are cultured in DMEM supplemented with penicillin-streptomycin-glutamine, non—essential amino acids and 10% fetal calf serum (Invitrogen-Gibco, Grand Island, N.Y.)

Differentiation into adipocytes, chondrocytes and osteocytes is performed as previously described[3]. Oil red, alcian blue and von Kossa staining is performed using standard techniques. Immunoreactivity for collagen type II is performed on paraformaldehyde fixed, paraffin-embedded sections using a goat anti-collagen á1 Type II and donkey anti-goat IgG antibody conjugated with HRP (Santa Cruz, Santa Cruz, Calif.).

Karyotyping

Cells received at about 80% confluence in Petri dish. Cells are treated with colcemid for mitotic arrest and harvested by standard hypotonic treatment and methanol: acetic acid (3:1) fixation. Slides are prepared by standard air drying method and hybridized with SKY paint probe (ASI). Post hybridization washes are performed according to the protocols provided by the manufacturer and established in our laboratory. 20-30 metaphase cells per culture were are. The karyotype of each culture is representative of >80% metaphase cells.

Transplantation Studies $2 \times 10^6$ cells are resuspended in 30 µl of saline and transferred into the renal subcapsular space as previously described[27] After four months, the mice are sacrificed and the kidneys are removed, fixed in 4% paraformaldehyde, paraffin-embedded, sectioned at 4 µM and stained with H&E.

Western Blot Analysis

Standard procedures are used[28]. Briefly, cells are lysed in RIPA buffer and centrifuged at 14,000 rpm for 15 minutes at 4° C. 20 µg supernatant is denatured, separated on 10 SDS-polyacrylamide gel, electro-blotted onto a nitrocellulose membrane and membrane is incubated sequentially with a primary antibody, then either a HRP conjugated-secondary antibody or a biotinylated secondary antibody followed by neutroavidin-HRP, and finally, a HRP enhanced chemiluminescent substrate, ECS (Pierce, Rockford, Ill.).

Primary antibodies used are 1:200 dilution of anti-OCT4, anti-SOX-2 and β-actin (Santa Cruz Biotechnology, Calif.), Secondary antibodies are HRP-conjugated goat anti-rabbit, rabbit anti-goat and rabbit antimouse.

PCR

Genomic PCR for mouse- and human-specific repeat sequences are performed as previously described[8]. Genomic PCR for mouse- and human-specific repeat sequences are performed as previously described[8]. Real time RT-PCR is performed by reverse transcribing 1 µg of total RNA using a High Capacity cDNA Archive Kit (Applied Biosystems, Foster City, Calif.). The cDNA is diluted 10× in water and amplified by Taqman primers (Applied Biosystems, Foster City, Calif.) for 40 cycles.

Surface Antigen Analysis

Cell surface antigens on hESC-MSCs, and hESCs are analyzed using FACS. The cells are trypsinized for 5 minutes, centrifuged, resuspended in culture media and incubated in a bacterial culture dish for 2-3 hours in a 37° C., 5% $CO^2$ incubator. Cell surface antigens on hESC-MSCs and hESCs are analyzed by FACS.

The cells are trypsinized for 1 minute, centrifuged, washed with PBS, fixed in 4% paraformaldehyde for 0.5 hour at room temperature, washed and blocked in 2% FCS for 0.5 hour at room temperature with agitation. $1.5 \times 10^5$ cells are then incubated with each of the following conjugated monoclonal antibodies: CD24-PE, CD29-PE, CD44-FITC, CD49a-PE, CD49e-PE, CD105-FITC, CD166-PE, CD34-FITC, CD45-FITC (PharMingen, San Diego, Calif.) for 90 mins at room temperature.

After incubation, cells are washed and resuspended in PBS. Nonspecific fluorescence is determined by incubation of similar cell aliquots with isotype-matched mouse monoclonal antibodies (PharMingen, San Diego, Calif.). Data are analyzed by collecting 20,000 events on a Cyan LX (Dako North America, Inc., Carpinteria, Calif.) instrument using WinMDI software. Nonspecific fluorescence is determined by incubation of similar cell aliquots with isotype-matched mouse monoclonal antibodies (PharMingen, San Diego, Calif.), or with secondary antibody alone.

Illumina Gene Chip Analysis

Total RNA (2 µg) from 3 samples each of primary BM and adipose-derived MSCs, from two biological replicates of HuES9.E1, HuES9.E3, HuES9.E1 and three undifferentiated hESC lines, H1, Hes3 and HuES9 are cnverted to biotinylated cRNA using the Illumina RNA Amplification Kit (Ambion, Inc., Austin, Tex.) according to the manufacturer's directions.

Samples are purified using the RNeasy kit (Qiagen, Valencia, Calif.). Hybridization to the Sentrix HumanRef-8 Expression BeadChip (Illumina, Inc., San Diego, Calif.), washing and scanning are performed according to the Illumina BeadStation 500x manual. The data are extracted, normalized and analyzed using Illumina BeadStudio provided by the manufacturer. Transcript signals that are below the limit of detection (LOD) at 99% confidence are eliminated as genes not expressed.

Example 2

Generating MSC Cultures from Human ES Cell Lines

When hESC colonies are dispersed by trypsin and then passaged on gelatinized tissue culture plates in the absence of feeder, and in serum-free media that is supplemented with serum replacement media, FGF2 and optionally PDGF AB, a culture of fibroblast-like cells which is similar or identical (preferably homogenous) to each other is generated within two weeks.

The cultures have a fibroblastic cellular morphology that resembled BM-MSCs (FIG. 1A). Dispersing hESC colonies by collagenase is not efficient in generating these fibroblast-like cells.

Figure 1B:
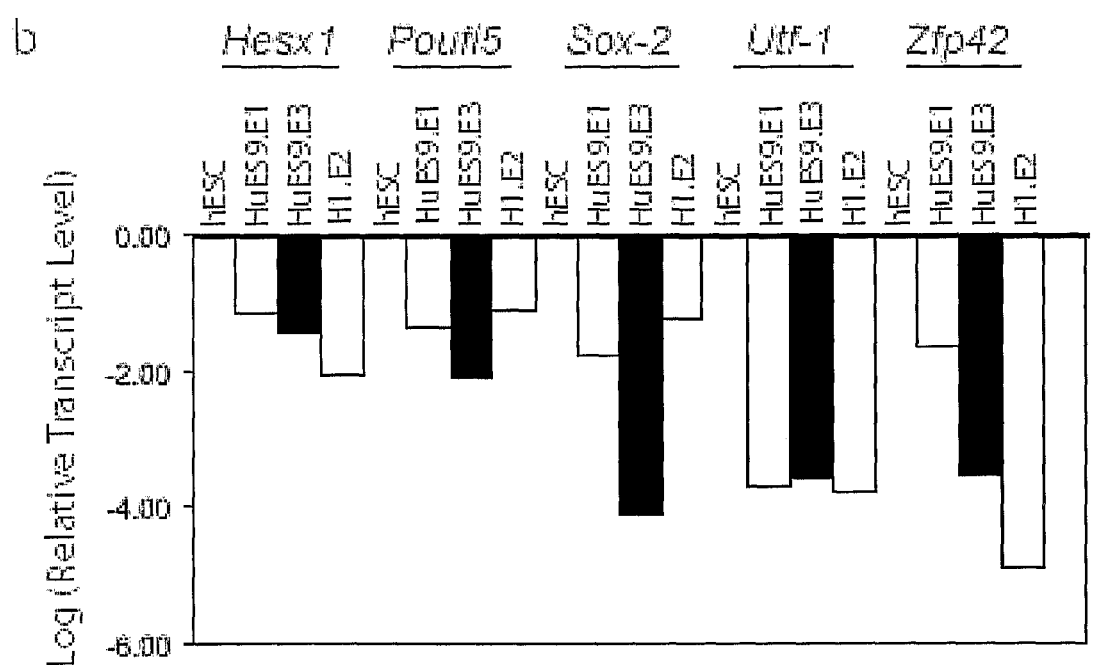
Figure 1C:
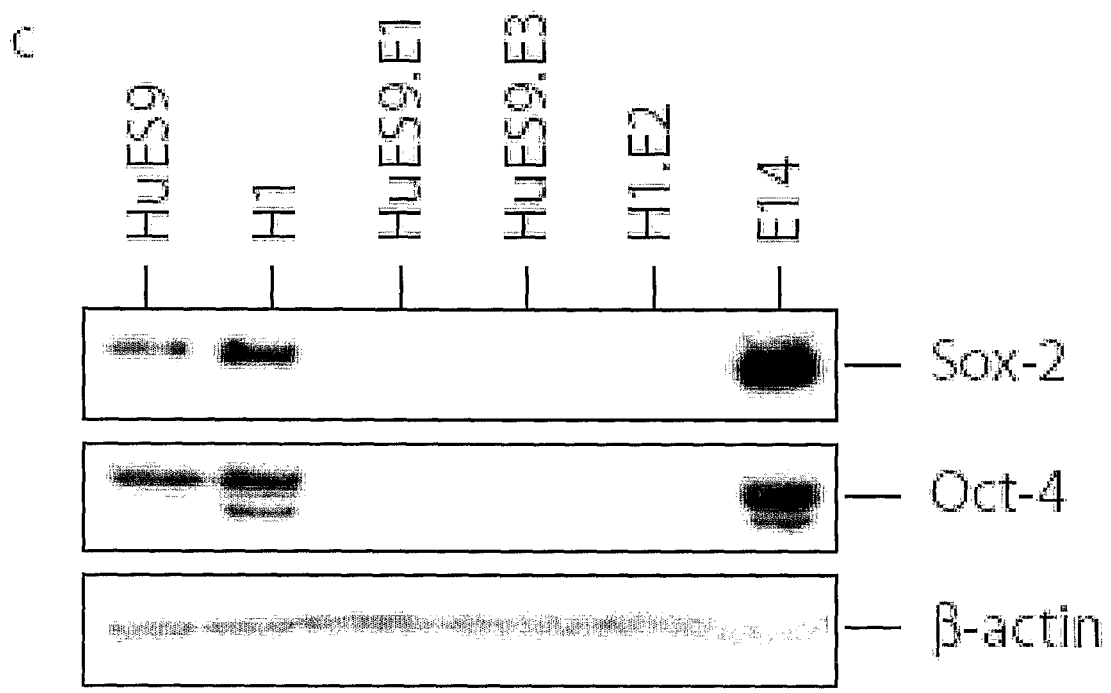
Figure 1D:
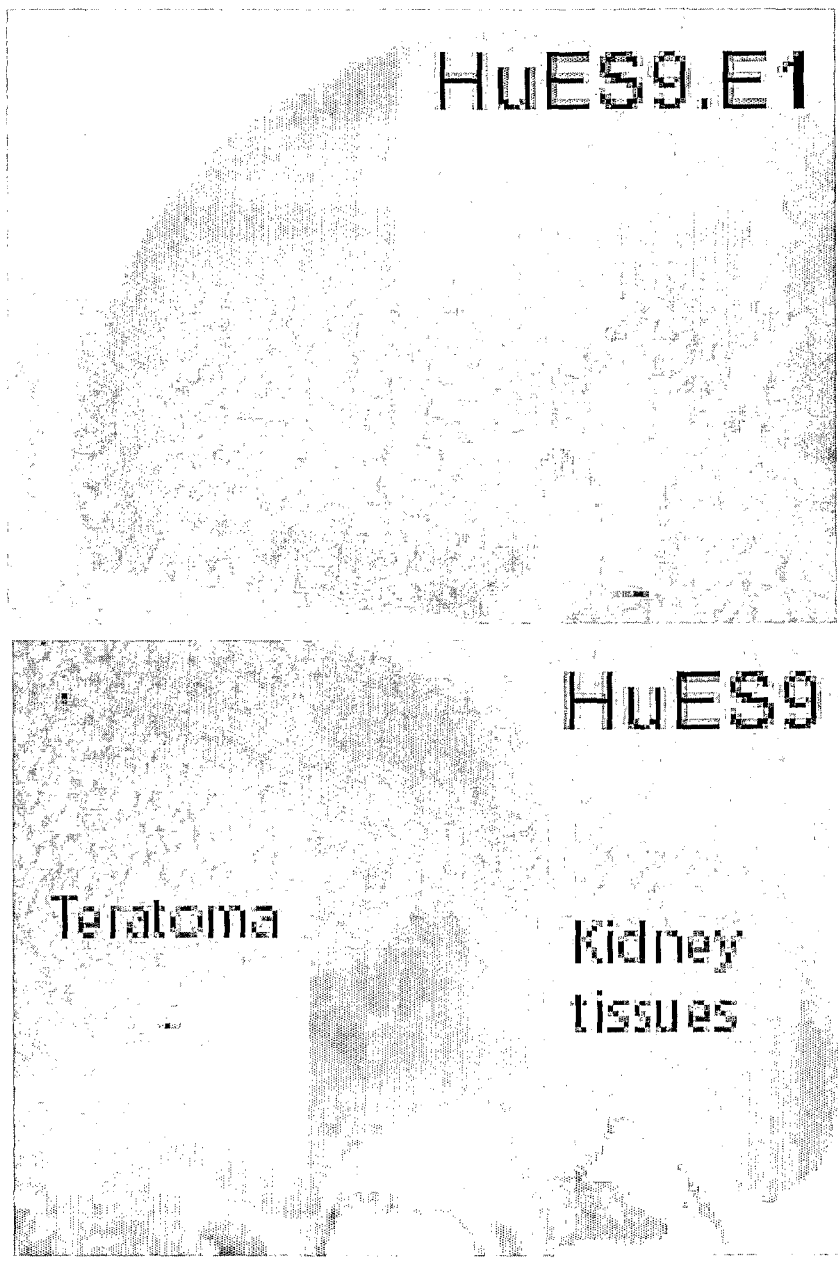

Two polyclonal cultures, huES9.E1 and huES9.E3, are independently generated from huES9 ESC line, while the third, H1.E2 is generated from H1 ESC line. Expression of several pluripotency-associated genes is generally reduced. For example, transcript levels of HESX1, POUFL5, SOX-2, UTF-1 and ZFP42 are >$10^{1-5}$ fold below that in the hESCs (FIG. 1B). Protein levels of OCT4, NANOG and SOX2 are also reduced (FIG. 1C). As typified by huES9.E1, these cells did not have detectable alkaline phosphatase activity (FIG. 1D).

Figure 1E:
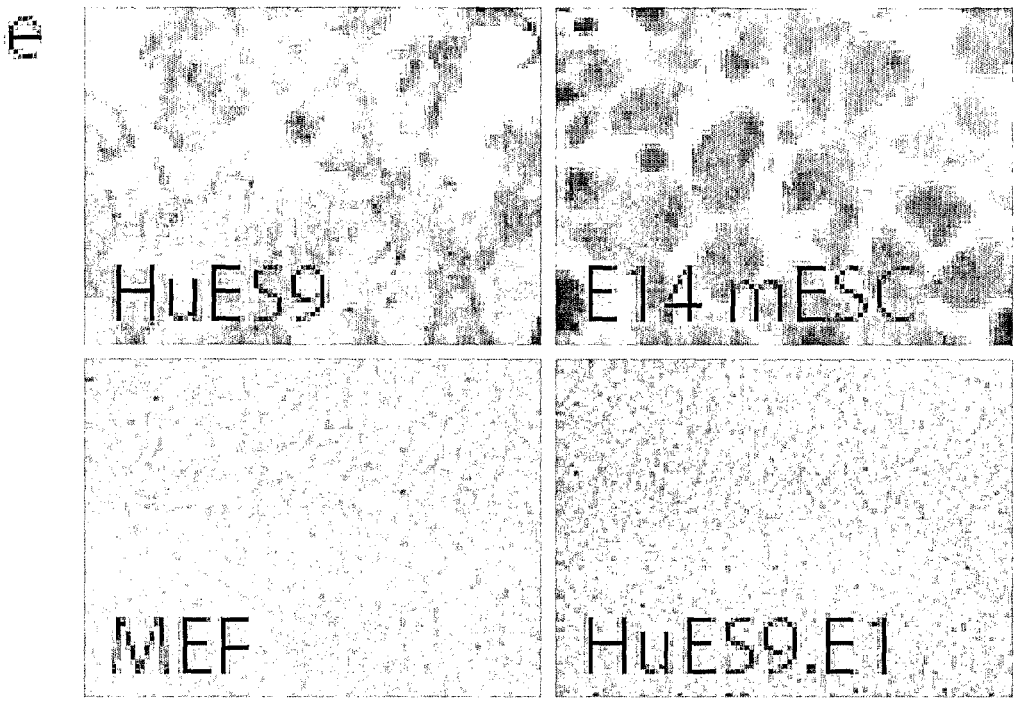
Figure 1F:
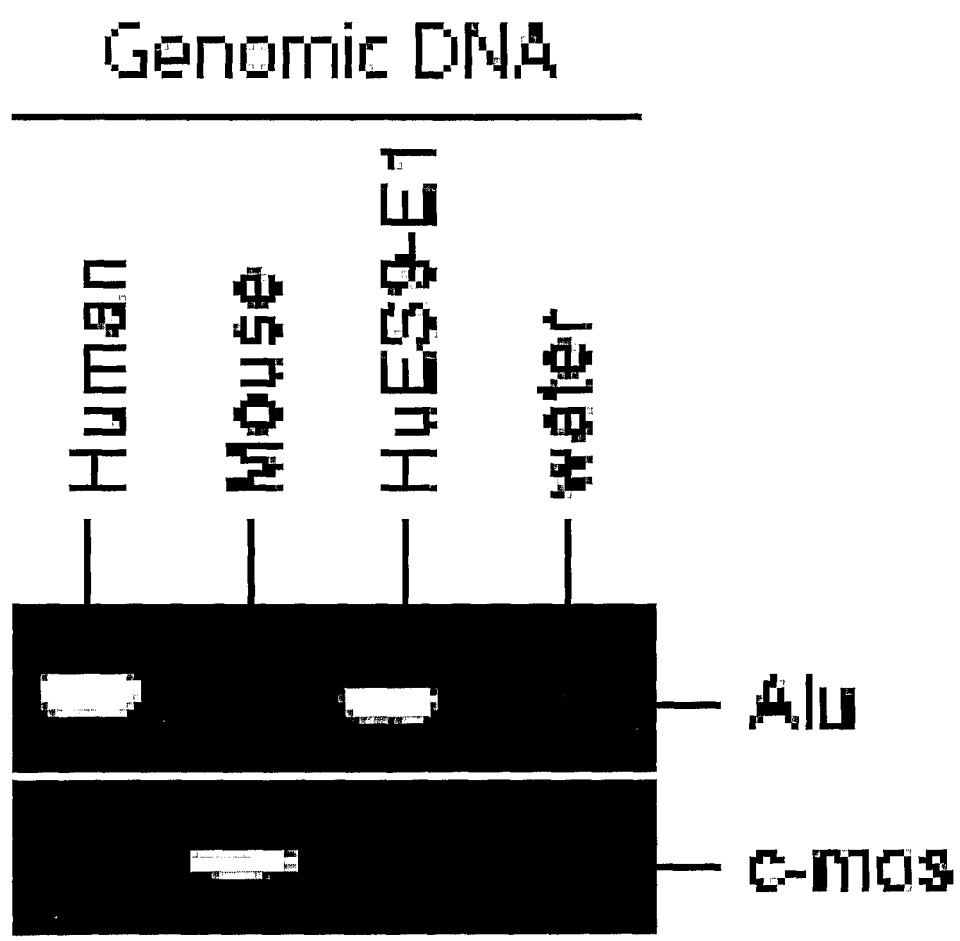
Figure 1G:
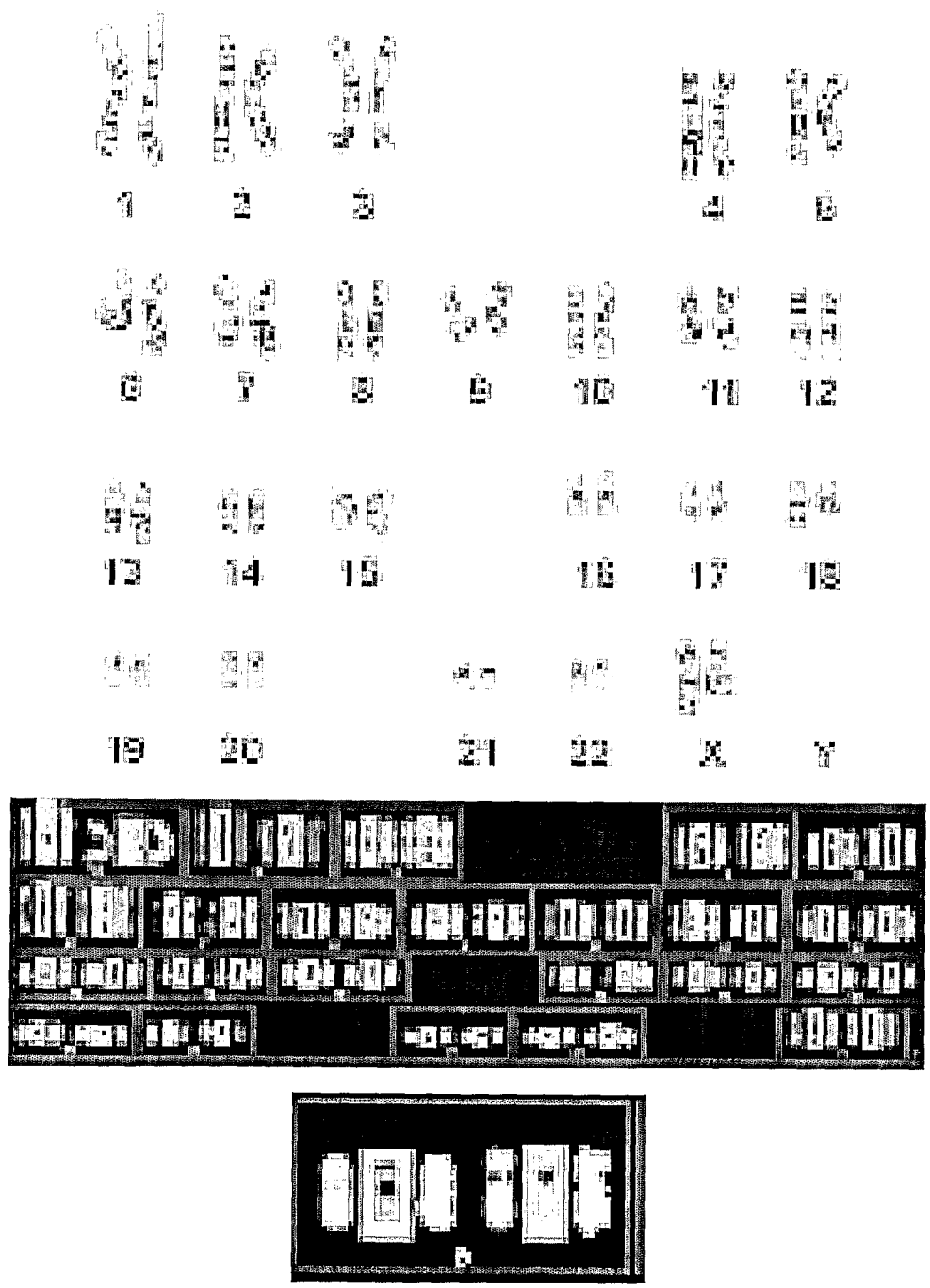

Unlike its parental HuES9 cells, renal subcapsular transplantation of 1×$10^6$ HuES9.E1 cells in immune compromised SCID mice did not induce the formation of a teratoma during a four-month observation period (FIG. 1E). To assess the possibility that these cells are contaminated or fused with mouse feeder cells[8], these cultures are tested and shown to be negative for mouse-specific c-mos repeat sequences but positive for human specific alu repeat sequences (FIG. 1F).

The average population doubling time of HuES9.E1, HuES9.E3 and H1.E2 are 72, 72 and 120 hours respectively. Population doubling time is highly dependent on cell density and is most optimal at between 30-80% confluency. After about 80 population doublings, HuES9.E1 have a 46 XX inv(9)(p13q12 karyotype. The chromosome 9 inversion originated from the parental huES9 hESC line[6]. HuES9.E3 also have 46 XX inv(9)(p13q12 karyotype while H1.E1 has a 46, XY karyotype after 36 and 32 population doubling time. We observed that the cells began to manifest abnormal, nonclonal chromosomal aberrations in ~10-30% of cells after about 35 population doublings (data not shown) and cells are not used after 35 population doublings.

Example 3

Surface Antigen Profile

Figure 2A:
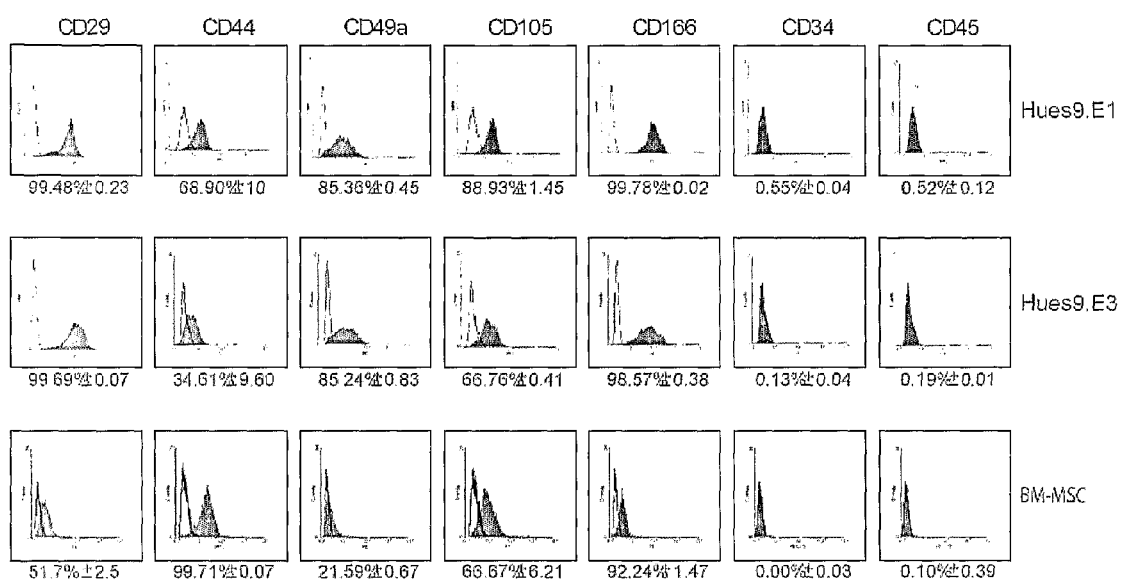
FIGS. 2A-2B. Surface antigen profiling by FACS analysis.

Surface antigen profiling of HuES9.E1, HuES9.E3 and H1.E2 by FACS analysis revealed a surface antigen profile that is qualitatively similar to that defined for BMMSCs i.e. CD29+, CD44+, CD49a and e+, CD105+, CD166+ and CD34−, CD45−[9-11] (FIG. 2A) The intensity of fluorescent labelling and distribution of labelled cells varied with each of the hESC-MSC cultures (FIG. 2A).

Figure 2B:
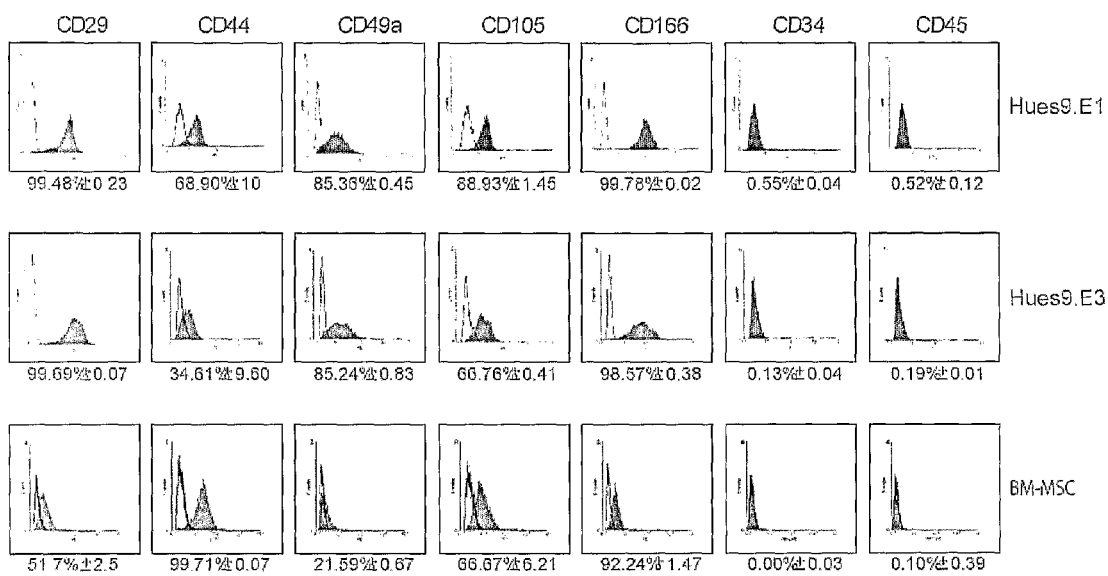

To compare the surface antigen profile of these cells to that of BM-MSCs, HuES9.E1, HuES9.E3 and H1.E1 are grown in the same BM-MSC culture media supplemented with 10% fetal calf serum for two passages. Despite the change in culture condition, HuES9.E1, HuES9.E3 and H1.E1 continued to be CD29+, CD44+, CD49a+, CD105+, CD166+ and CD34−, CD45− (FIG. 2B; data not shown for H1.E1) and are largely similar to that of BM-MSCs. An exception is CD49a which had a much lower expression in BM-MSCs. These data indicated that the hESC-MSCs exhibited characteristic BM-MSC surface antigen profiles that are stable and are not significantly influenced by changes in their microenvironment.

Example 4

Differentiation Potential of hESC-MSC: Adipogenesis, Chondrogenesis and Osteogenesis As all of the surface antigens associated with MSCs are also expressed on many other cell types and the expression of these surface antigens are variable, identification of presumptive MSCs have traditionally relies on functional parameters[9]. It is reported that the default differentiation pathway of MSCs in culture is osteogenesis with varying degrees of adipogenesis and chondrogenesis[9].

Differentiation potential of HuES9.E1 cells is therefore tested using standard differentiation conditions for adipogenesis, chondrogenesis and osteogenesis using published protocols[3].

Adipocytic differentiation is highly efficient with oil droplets observed in >99% of the cells (FIG. 3A). Consistent with its role as important transcription factor in adipogenesis[12], PPARγ mRNA in the hESC derived MSCs which is about 10-100 fold higher than that in their respective parental ESC lines increased by a further 2 fold (FIG. 3A).

Chondrogeneiss or the formation of cartilage is also efficient with >90% of cells producing proteoglycan in extracellular matrix as detected by alcian blue staining (FIG. 3B) and ~20% of the cells being immunoreactive for collagen II. Transcript level of aggrecan, an cartilage-specific extracellular matrix protein is also increased[13] (FIG. 3B). However, transcript level of collagen II, another cartilage-specific extracellular matrix protein is decreased despite the presence of collagen II immunoreactivity in the matrix. The reason is not known but some mRNAS particularly those with AU-rich elements are known to be destabilized when translated[14,15].

When HuES9.E1 cells are induced to undergo osteogenesis or the formation of bone, expression of bone-specific alkaline phosphatase (ALP) and bone sialoprotein (BSP)[16] is upregulated by 2-3 fold (FIG. 3C). However, mineralization, a more advanced stage of bone formation[17] as determined by von Kossa staining is poor (FIG. 3C). There is <1% positive staining in the differentiated culture.

Example 5

Gene Expression Profile

Gene expression profiling of the hESC-MSCs are performed to 1) assess the relatedness of hESC-MSC cultures with adult tissue-derived MSCs using BM-MSCs and adipose derived (ad)-MSCs from three different individuals, and three human ESC lines; 2) assess the relatedness between each of the three hESC-MSC cultures; 3) compare the similarity and differences between MSCs derived from hESC and those derived from BM.

Labeled cDNA prepared from total RNA RNA are hybridized to Illumina BeadArray containing about 24,000 unique features. Hierarchical clustering of expressed genes in three hESC-MSC cultures i.e. HuES9.E1, HuES9.E3 and H1.E2, three BM-MSC samples and three adipose derived (ad)-MSC samples revealed that the gene expression profile of hESC-MSCs is more closely related to that of adult tissue-derived MSCs, namely BM-MSC and ad-MSC than to their parent hESCs (FIG. 4A).

Figure 4B:
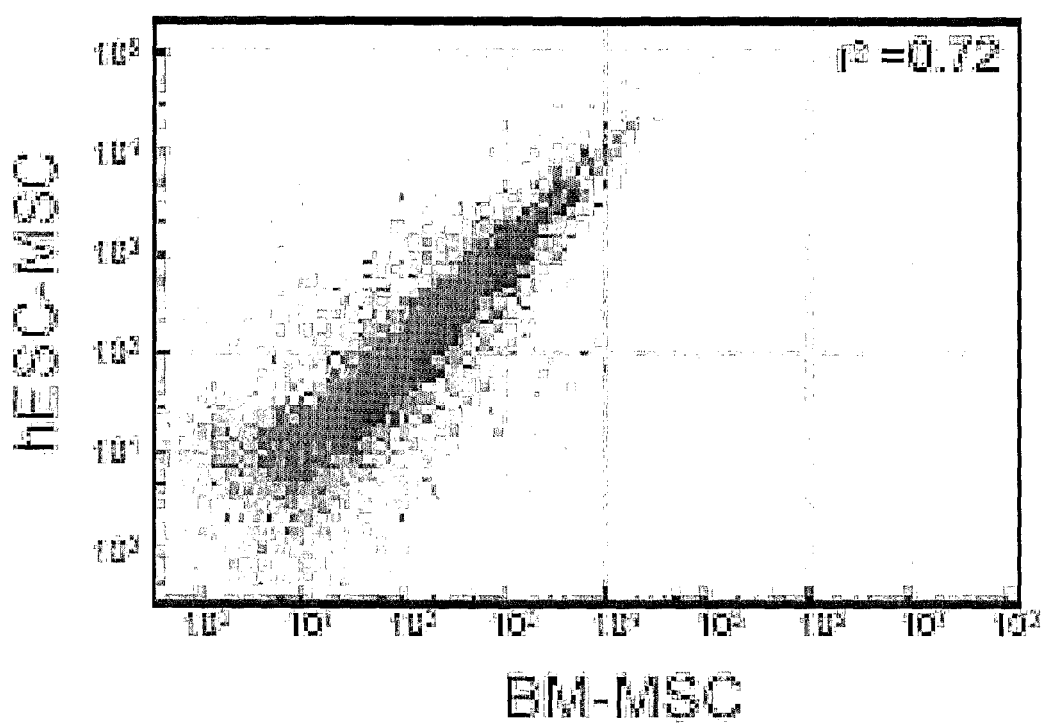
Figure 4B:
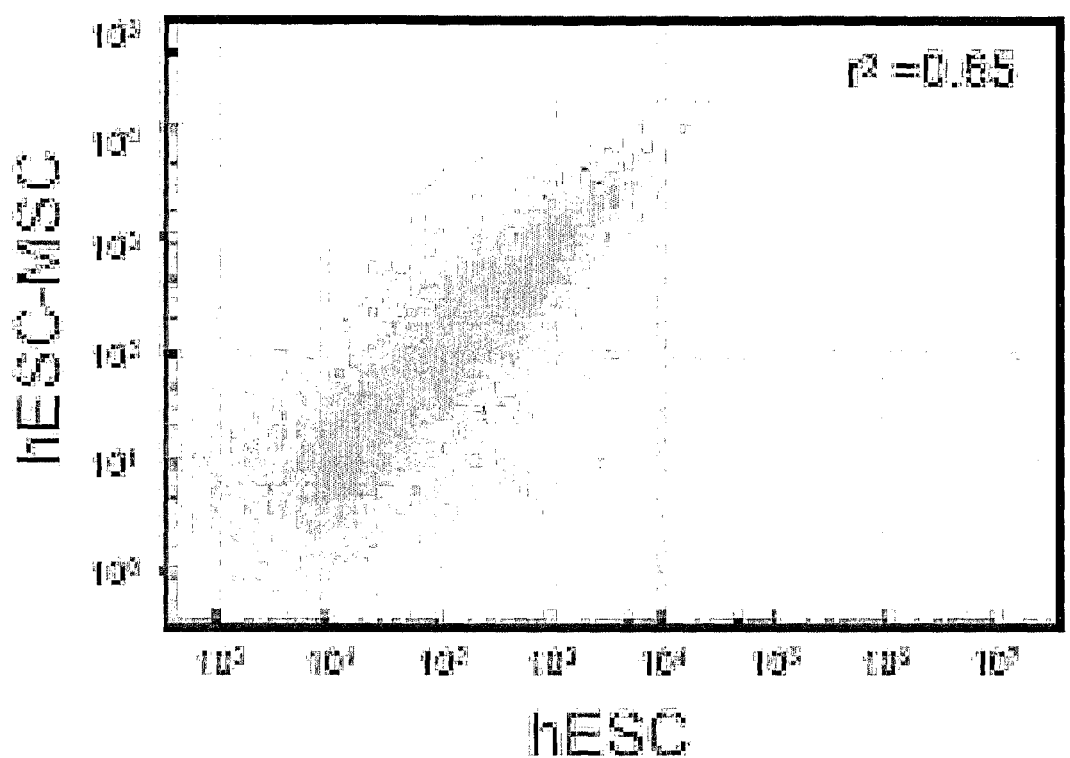
Figure 4C:
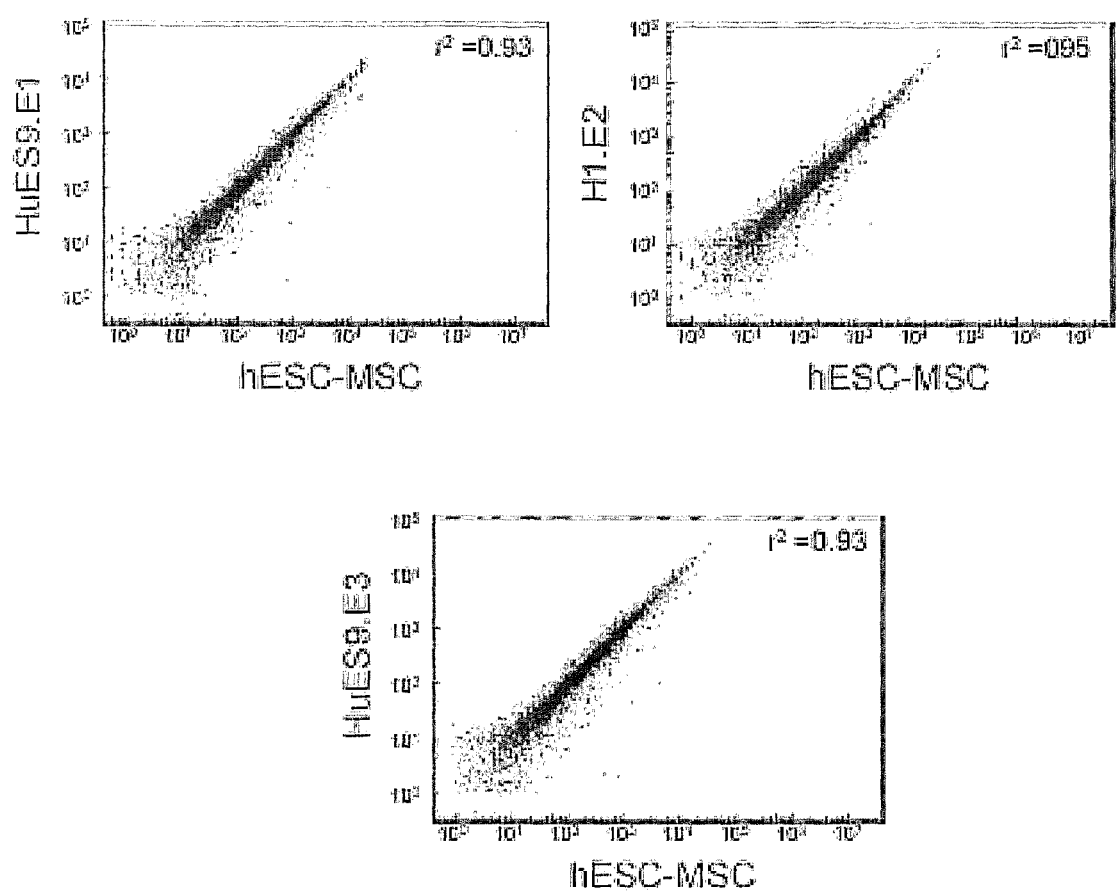
Figure 4D:
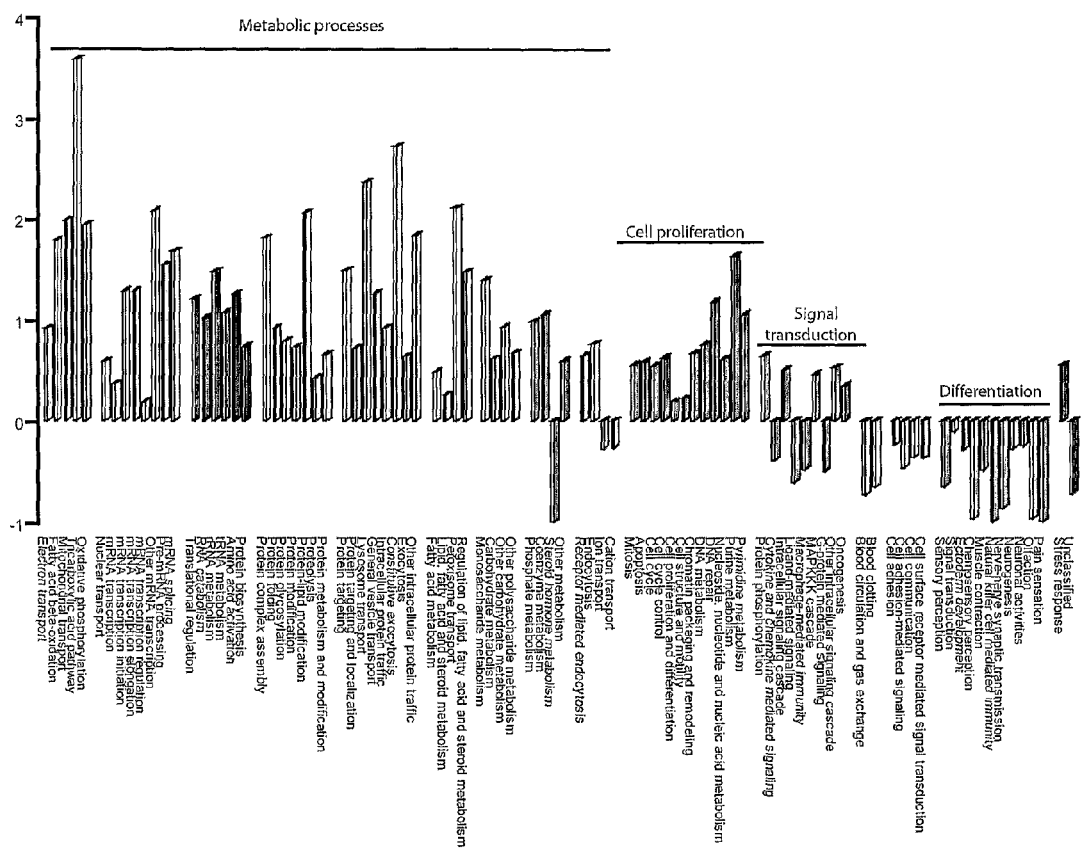
Figure 4E:
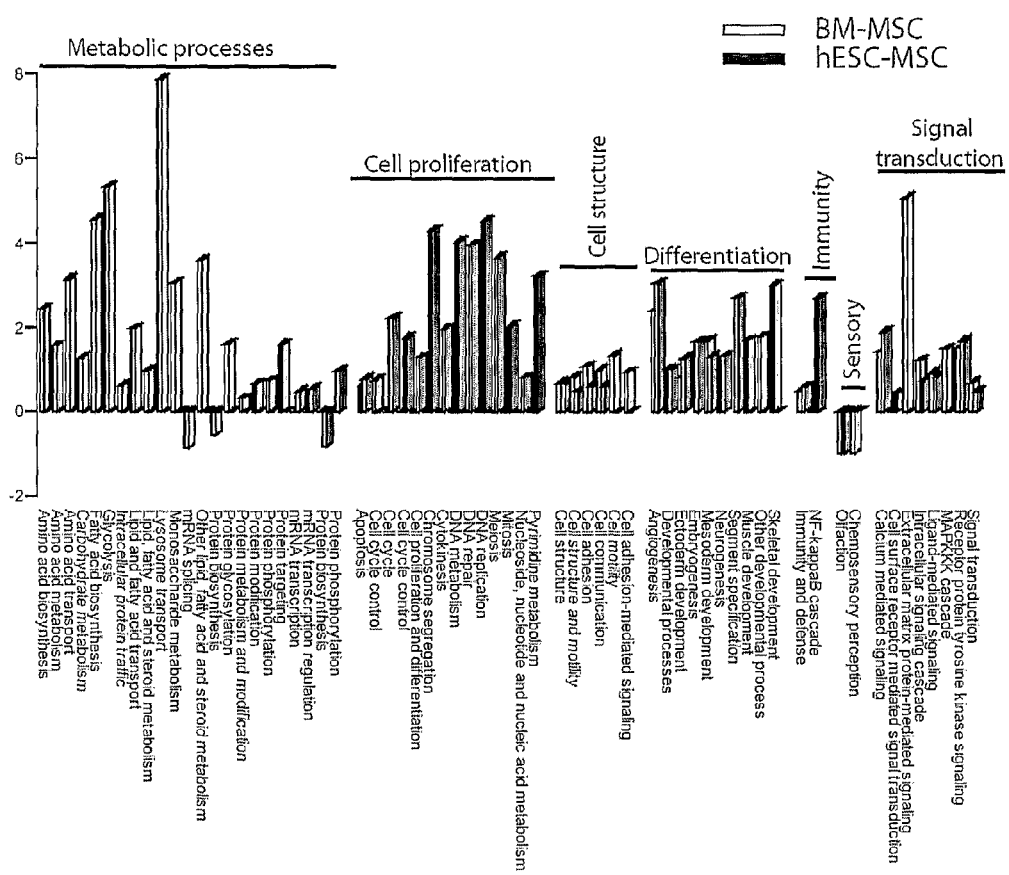

Interestingly, MSCs clustered according to their tissue of origin, and this can be further demarcated into adult versus embryonic tissue as suggested by the clustering of ad-MSCs and BMMSCs as a distinct group from hESC-MSCs. Pairwise comparison of gene expression between hESC-MSCs and BM-MSCs revealed a correlation coefficient of 0.72 suggesting that while there is significant conservation of gene expression in both hESC-MSCs and BM-MSCs, there are also significant differences (FIG. 4B). Pairwise comparison between hESC-MSCs and hESCs confirmed the distinction of hESC-MSCs from hESCs with a low correlation coefficient of 0.65 (FIG. 4C).

To assess the relatedness between each of the three hESC-MSC cultures, HuES9.E1, H1.E2 and HuES9.E3 are each compared to the same reference consisting of HuES9.E1, H1.E2 and HuES9.E3. The correlation coefficients of HuES9.E1, H1.E2 and HuES9.E3 to the same reference are virtually identical i.e. 0.93, 0.95 and 0.93, respectively suggesting that HuES9.E1, H1.E2 and HuES9.E3 are highly similar (FIG. 4C).

Of 8699 and 8505 genes that are expressed above the limit of detection at 99% confidence level in hESC-MSC and BM-MSC, respectively, 6376 genes are expressed in both hESC-MSCs and BM-MSCs at <2.0 fold difference. As these genes are likely to provide insights into the fundamental biology of MSCs, we examine the biological processes that are driven by these genes. Of the 6376 commonly expressed genes, 4,064 are found in the Panther classified gene list (March 2006; http://www.pantherdb.org/).

Classification of these genes into different biological processes revealed that the frequency of genes in some of the biological processes are significantly over or under represented (p<0.01) when compared to the reference list consisting of 23481 genes in NCBI: *H. sapiens* gene database. For example, there are an overrepresentation of genes in metabolic processes that are likely to be important for growth and self-renewal of putative stem cells. These processes include basal metabolic processes for catabolic and anabolic activities, biosynthesis of secretory products that require extensive post-translational modifications e.g. glycosylation, and cellular proliferation (FIG. 4C).

Consistent with their mesenchymal potential, there is also an under-representation of genes involved in ectoderm differentiation particularly neural development. The gene expression analysis also suggested that MAPKKK signalling is prominent in both BM-MSC and hESC-MSCs. MAPKKK signalling which consists of at least three subfamilies, namely the classical MAPS (also known as ERK), stress-activated protein kinase/c-Jun N-terminal kinase (JNK) and p38 kinase, are associated with proliferation, differentiation, development, regulation of responses to cellular stresses, cell cycle, death and survival[18-21].

Further analysis of the gene expression profiles of hESC-MSC and BM-MSC revealed that 1142 and 1134 genes are expressed at >2.0 fold in hESC-MSC and BM-MSC, respectively. Of these, 738 and 880 genes respectively, are located in Panther classified gene list (March 2006; http://www.pantherdb.org/) and classified into biological processes. Biological processes that are significantly over- or under-represented (p<0.01) when compared to the reference list of 23481 genes in NCBI: *H. sapiens* gene database are selected.

Genes that are preferentially expressed in BM-MSCs are clustered in biological processes that are involved in metabolic processes, cell structure, differentiation and signalling while preferentially expressed hESC-MSC genes are clustered in those processes involved in proliferation, differentiation, immunity and signal transduction (FIG. 3C). The overrepresentation of genes in biological processes associated with proliferation is consistent with the higher proliferative capacity of hESC-MSC over BM-MSC.

Although highly expressed genes in either hESC-MSC or BM-MSC are over-represented in the general categories of differentiation and signalling, the specific biological processes within each category are differently represented in hESC-MSC and BM-MSC. For example, differentiation processes that are associated with early embryonic development such as embryogenesis and segmentation are over-represented in hESC-MSC while those associated with late embryonic development e.g. skeletal development and muscle development are overrepresented in BM-MSC. Similarily, extracellular matrix protein-mediated signalling and MAPKKK cascade are overrepresented in BM-MSC. Together, these observations suggest that differentiation potential and signalling pathway utilisation in hESC-MSC and BM-MSC may not be identical.

Example 5

Distinguishing Surface Markers for hESCs and hESC-Derived MSCs for Isolating of Single Cell-Derived MSC Population The genome-wide gene expression is queried for highly expressed genes in either hESC-MSC or hESC that encode for membrane proteins to facilitate the isolation of MSCs from differentiating hESCs. From a list of top 20 highly expressed genes encoding for putative membrane proteins in either hESC-MSCs or hESCs, candidate genes are selected for which antibodies against their gene product is commercially available (Table E1A and E1B below). Among those candidate genes that are highly expressed in hESC derived

TABLE E1A

Highly expressed membrane proteins in hESC-derived MSC over hESC

| Symbol | Fold change | Accession | Synonyms |
| --- | --- | --- | --- |
| ANPEP | 715.50 | NM_001150.1 | CD13; LAP1; PEPN; gp150 |
| ENG | 479.50 | NM_000118.1 | END; ORW; HHT1; ORW1; CD105 |
| SCN9A | 251.20 | NM_002977.1 | PN1; NE-NA |
| TRPV2 | 187.90 | NM_016113.3 | VRL; VRL1; VRL-1; MGC12549 |
| RAMP1 | 182.30 | NM_005855.1 | |
| F2RL2 | 152.03 | NM_004101.2 | PAR3 |
| NTSR1 | 141.15 | NM_002531.1 | NTR |
| GABRA2 | 122.05 | NM_000807.1 | |
| SLC16A4 | 106.60 | NM_004696.1 | MCT4 |
| ITGA4 | 103.60 | NM_000885.2 | CD49D |
| NCAM2 | 93.31 | NM_004540.2 | NCAM21; MGC51008 |
| IL1R1 | 86.80 | NM_000877.2 | P80; IL1R; IL1RA; CD121A; D2S1473; IL-1R-alpha |
| PDGFRA | 80.25 | NM_006206.2 | CD140A; PDGFR2 |
| VCAM1 | 71.30 | NM_080682.1 | INCAM-100 |
| SSFA2 | 69.74 | NM_006751.3 | CS1; CS-1; KRAP; SPAG13; KIAA1927 |
| TRHDE | 58.63 | NM_013381.1 | PAP-II |
| EDG2 | 55.82 | NM_001401.3 | LPA1; edg-2; vzg-1; Gpcr26; Mrec1.3; rec.1.3 |
| NT5E | 48.15 | NM_002526.1 | eN; NT5; NTE; eNT; CD73; E5NT |
| FLRT2 | 46.51 | NM_013231.2 | KIAA0405 |
| FAP | 44.43 | NM_004460.2 | FAPA; DPPIV; SEPRASE |

TABLE E1B

Highly expressed membrane proteins in hESC over hESC-derived MSC

| Symbol | Fold change | Accession | Synonyms |
| --- | --- | --- | --- |
| ITGB1BP3 | 2642.33 | NM_014446.1 | MIBP |
| PTPRZ1 | 2126.50 | NM_002851.1 | PTPZ; HPTPZ; PTP18; PTPRZ; RPTPB |
| CNTN1 | 430.00 | NM_175038.1 | F3; GP135 |
| PCDH1 | 342.08 | NM_002587.3 | PC42; PCDH42; MGC45991 |
| PODXL | 303.06 | NM_005397.2 | PCLP; Gp200 |
| GPR64 | 217.67 | NM_005756.1 | HE6; TM7LN2 |
| PROM1 | 209.04 | NM_006017.1 | AC133; CD133; PROML1 |
| GPRC5C | 205.00 | NM_022036.2 | RAIG3; RAIG-3 |
| CD24 | 166.98 | NM_013230.1 | CD24A |

TABLE E1B-continued

Highly expressed membrane proteins in hESC over hESC-derived MSC

| Symbol | Fold change | Accession | Synonyms |
|---|---|---|---|
| CLDN3 | 166.42 | NM_001306.2 | RVP1; HRVP1; CPE-R2; CPETR2 |
| TACSTD1 | 163.81 | NM_002354.1 | EGP; KSA; M4S1; MK-1; EGP40; MIC18; TROP1; Ep-CAM; hEGP-2; CO17-1A; GA733-2 |
| HTR3A | 140.00 | NM_000869.1 | HTR3 |
| FGFR4 | 139.96 | NM_022963.1 | TKF; JTK2 |
| ADCY1 | 127.44 | NM_021116.1 | |
| FGFR3 | 123.27 | NM_022965.1 | ACH; CEK2; JTK4; HSFGFR3EX |
| IL17RB | 91.70 | NM_018725.2 | CRL4; EVI27; IL17BR; IL17RH1; MGC5245 |
| SORL1 | 66.79 | NM_003105.3 | LR11; LRP9; SORLA; gp250; SorLA-1 |
| GPM6B | 60.70 | NM_005278.2 | M6B |
| KCNS3 | 35.26 | NM_002252.3 | KV9.3; MGC9481 |
| FZD3 | 33.94 | NM_017412.2 | Fz-3; hFz3 |

Tables E1A and E1B above show highly expressed surface antigen encoding genes in hESC-derived MSCs (Table E1A) or their parental hESCs (Table E1B). Based on gene expression analysis by microarray hybridization, the top twenty genes that were highly expressed in hESC-derived MSCs (HuES9.E1, HuES9.E3 and H1.E2) vs hESCs (HuES9, H1 and Hes3 hESCs) (Table E1A) and vice versa (Table E1B).

Figure 5A:
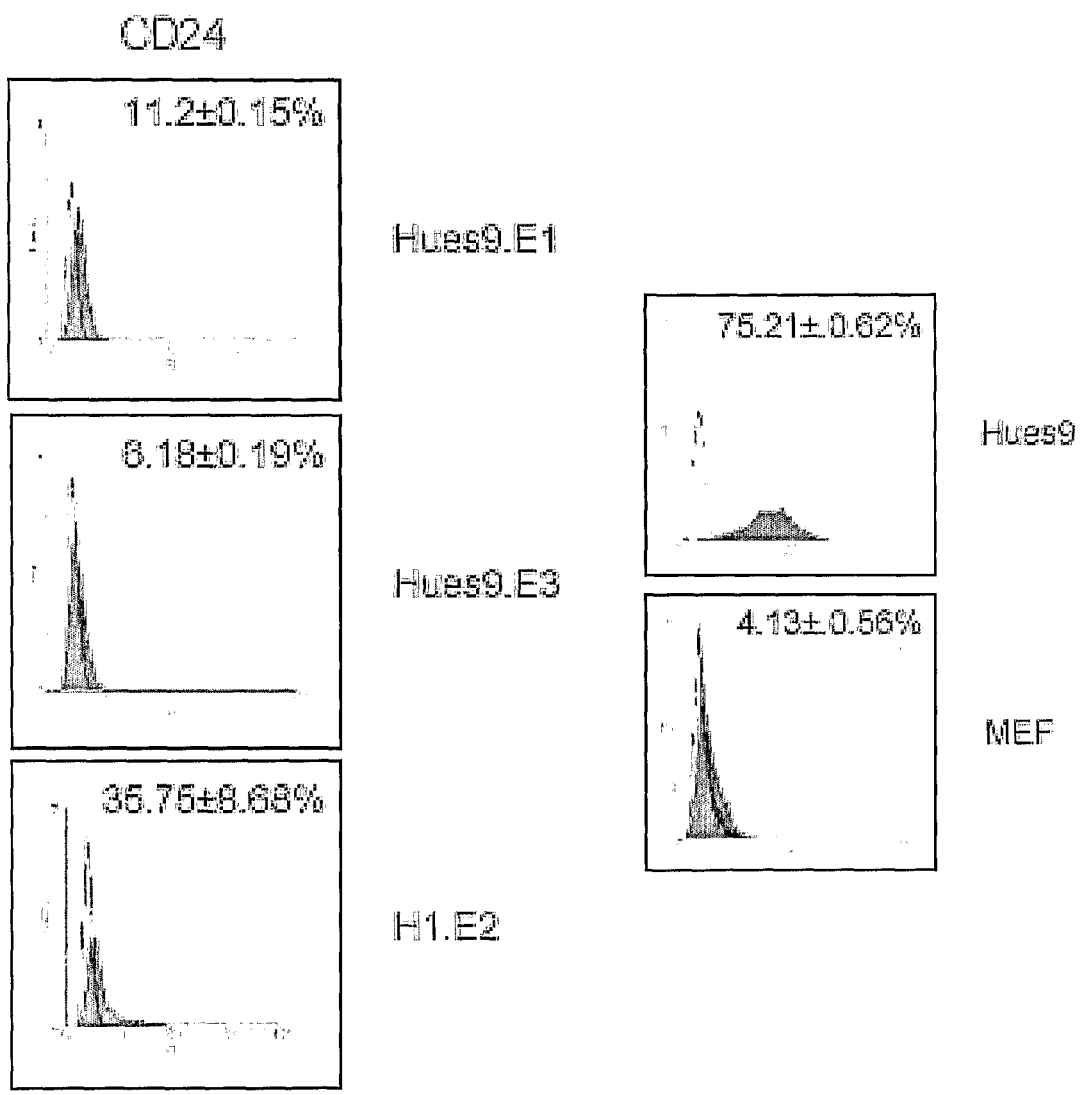
FIGS. 5A-5E. Positive and negative sorting for generation of hESC-MSC.

MSCs are ENG (CD105), ITGA4 (CD49d), PDGFRA, NT5E (CD73) that are characteristic surface markers of MSCs derived from adult tissues[9-11] and among those candidate genes that are highly expressed in hESC are previously identified as highly expressed hESC-specific genes, ITGB1BP3 and PODXL[22] and CD 24 whose expression has not been associated with hESCs. We confirmed that CD24 is highly expressed in hESC vs hESC-MSC (FIG. 5A).

Example 6

Deriving a Homogenous hESC-MSC Population

We next tested the utility of these markers to enhance the homogeneity of hESC-MSCs. One week after trypsinization and culture in media supplemented with serum replacement media, FGF2 and optionally PDGF AB, the cells in the culture is sorted by FACS for CD105 and against CD24.

Figure 5B:
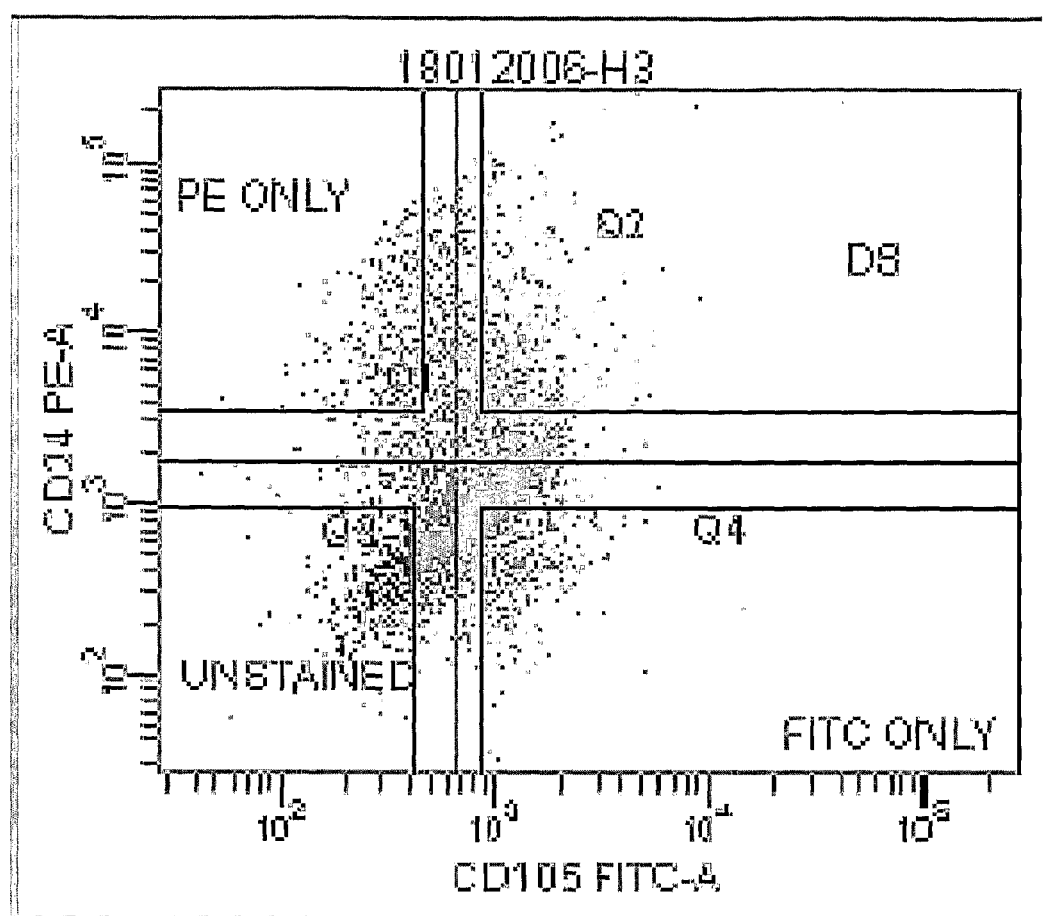

CD105+ and CD24− cells constituted 5% of the culture (FIG. 5B). Sorted cells are plated onto 10×96 well plates at 1 cell/well, 1×24 well plate at 100 cells/well and 3×6 well plates at 1000 cells/well. Of these, only five of the eighteen 1000 cells/wells generated MSC-like cultures suggesting that these cultures are likely to be generated from a single cell.

Figure 5C:
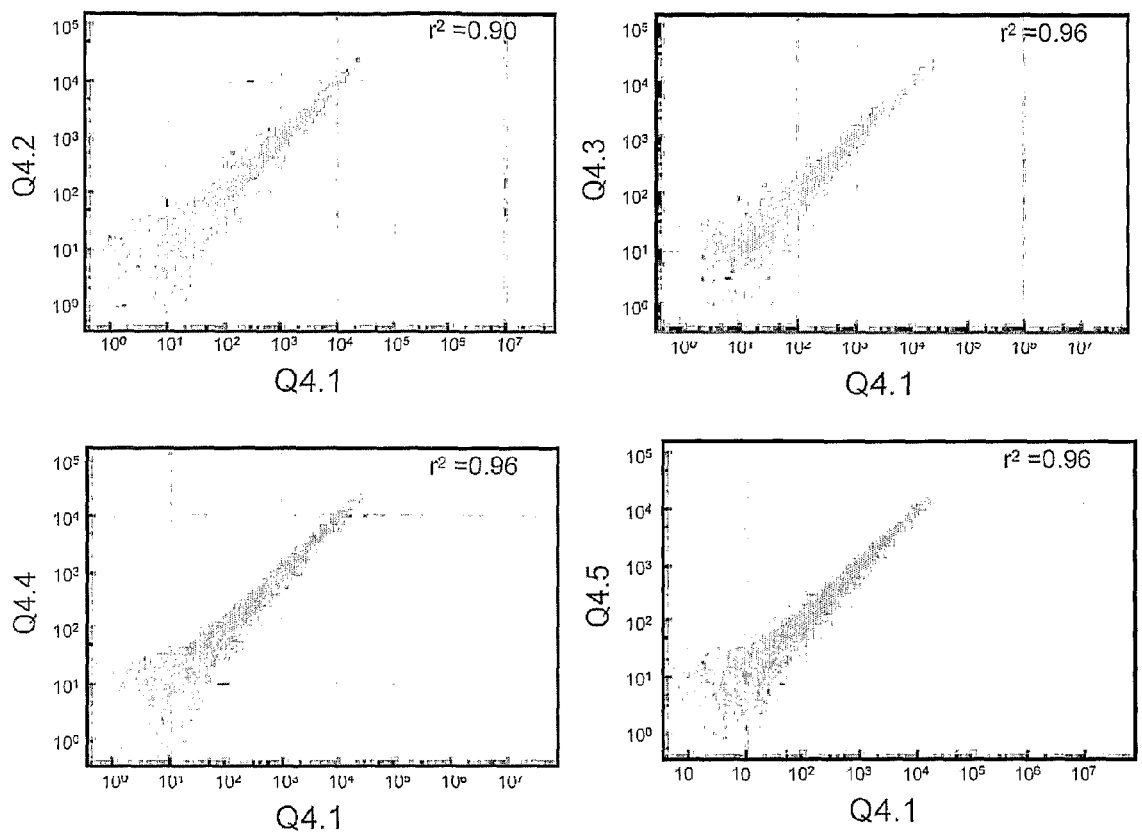

Genome-wide gene expression profiling of these five cultures, Q4.1 to Q4.5 using the Illumina BeadArray containing about 24,000 unique features revealed a high degree of similarity among the five cultures with four of the lines having a correlation coefficient of 0.96 and the remaining one with 0.90 (FIG. 5C). In our hands, the correlation coefficient between technical replicates performed at least one month apart using the same RNA sample is routinely in the range of 0.97 to 0.98. Q4.1 to Q4.5 are also highly similar to the hESC-MSCs consisting of huES9.E1, H1.E2 and huES9.E3, and BM-MSCs with a correlation coefficient of 0.87 and 0.81, respectively (FIG. 5D).

Figure 5D:
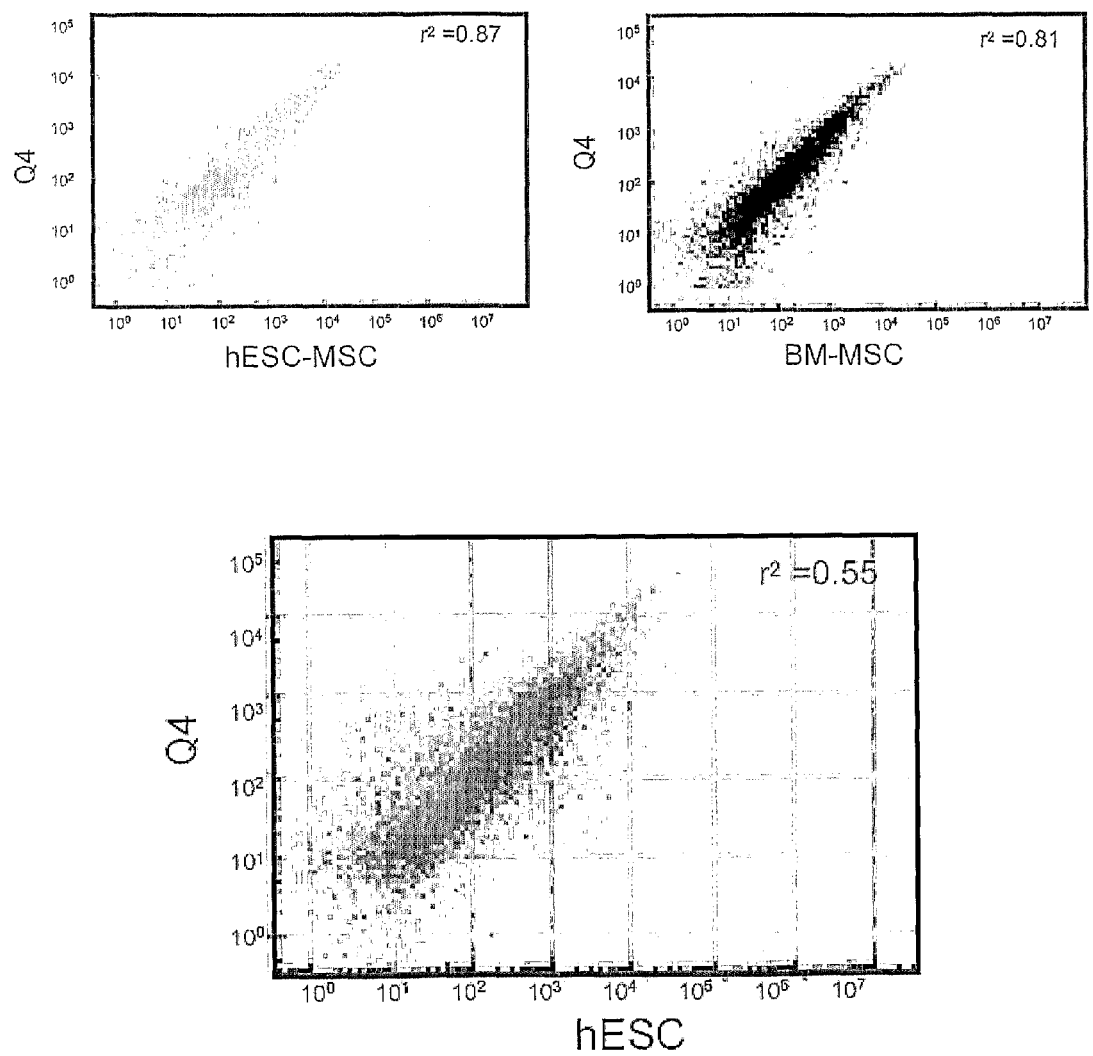
Figure 5E:
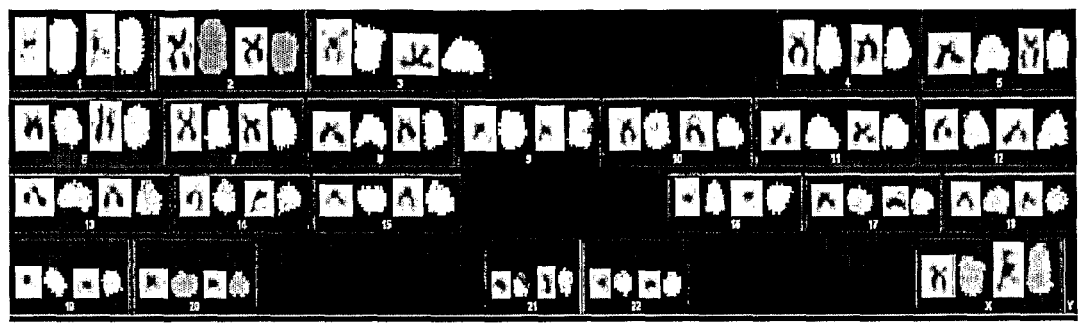

In contrast, the correlation coefficient of Q4.1 to Q4.5 to their parental HuES9.E1 hESC line is a low 0.55 (FIG. 5D). Chromosomal analysis using G banding and SKY is performed on randomly selected Q4.3 culture. Q4.3 has a normal karyotype with a chromosome 9 inversion that originated from its parental HuES9 hESC line (FIG. 5E)[6]. Together these observations show that highly homogenous MSC cultures can be generated by sorting for CD105+ and CD24− cells from trypsinized hESC culture after propagation in media supplemented with bFGF2 and optionally PDGF BB for one week.

The incorporation of positive and negative selectable markers into the derivation protocol resulted in the derivation of five monoclonal isolates with a genome-wide expression profile that is almost identical to each other and confirmed the specificity of the selection or sorting criteria. Global pairwise gene expression comparison between the five isolates reveal a near identical gene expression profile that is comparable to that observed for technical replicates using the same RNA samples.

Examples 7 to 15 describe experiments to analyse the proteome of human ESC-derived MSCs (hESC-MSCs). In these experiments, a chemically defined serum-free culture media is conditioned by human ESC-derived MSCs (hESC-MSCs) is analysed using a clinically compliant protocol. The conditioned media is analyzed by multidimensional protein identification technology (MuDPIT) and cytokine antibody array analysis, and reveals the presence of 201 unique gene products.

86-88% of these gene products have detectable transcript levels by microarray or qRT-PCR assays. Computational analysis predicts that these gene products will significantly drive three major groups of biological processes: metabolism, defense response, and tissue differentiation including vascularization, hematopoiesis and skeletal development. It also predicts that the 201 gene products activate important signalling pathways in cardiovascular biology, bone development and hematopoiesis such as Jak-STAT, MAPK, Toll-like receptor, TGF-beta signalling and mTOR signaling pathways.

Example 7

Analysis of Proteome of Human ESC-derived MSCs (hESC-MSCs): Materials and Methods Preparation of Conditioned Media HuES9.E1 cells are cultured as described above. 80% confluent HuES9.E1 cell cultures are washed 3 times with PBS, cultured overnight in a chemically defined media consisting of DMEM media without phenol red (Catalog 31053; Invitrogen-Gibco, Grand Island, N.Y.) and supplemented with ITS (Invitrogen-Gibco, Grand Island, N.Y.), 5 ng/ml FGF2 (Invitrogen-Gibco, Grand Island, N.Y.), 5 ng/ml PDGF AB (Peprotech, Rocky Hill, N.J.) glutamine-penicillin-streptomycin and β-mercaptoethanol. The cultures are then rinsed three times with PBS and then replaced with fresh defined media. After three days, the media are collected, centrifuged at 500×g and the supernatant is 0.2μ filtered. For LC MS/MS analysis, the conditioned media is placed in dialysis cassettes with MW cutoff of 3500 (Pierce Biotechnology, Rockford, Ill.), dialyzed against 3 changes of 10 vol. 0.9% NaCl, then concentrated 20 times using Slide-A-Lyzer Concentrating Solution, then dialysing against 10 changes of 100 vol. 0.9% NaCl before filtering with a 0.2μ filter. A same volume of non-conditioned media is dialyzed and concentrated in parallel with the conditioned media.

Cytokine Antibody Blot Assays

One ml of conditioned or non-conditoned media is assayed for the presence of cytokines and other proteins using Ray-Bio® Cytokine Antibody Arrays according to manufacturer's instruction (RayBio Norcross, Ga.).

LC MS/MS Analysis

Proteins in two ml of dialyzed conditioned (CM) or non-conditioned media (NCM) are reduced, alkylated, and tryptic digested as described {Washburn, 2001 #2997}. The samples are then desalted by passing the digested mixture through a conditioned Sep-Pak C-18 SPE cartridge (Waters, Milford, Mass., USA), washed twice with a 3% acetonitrile (ACN) (J T Baker, Phillipsburg, N.J.) and 0.1% formic acid (FA) buffer, and eluted with a 70% ACN and 0.1% FA buffer. The eluted samples are then dehydrated by speedvac to about 10% of their initial volumes and adjusted to 50 µl with 0.1% formic acid. The samples are kept at 4° C. prior to LC-MS/MS analysis.

The desalted peptide mixture is analyzed by MudPIT with a LC-MS/MS system (LTQ, ThermoFinnign, San Jose, Calif., USA). The sample is loaded into a strong cation exchange (SCX) column (Biobasic SCX, 5 um, Thermo Electron, San Jose, USA) and fractioned by 6 salt steps with 50 ul of buffers (0, 2, 5, 10, 100, and 1000 mM of ammonium chloride in a 5% ACN and 0.1% FA) in first dimension. The peptides eluted from SCX column are concentrated and desalted in a Zorbax peptide trap (Agilent, Pola Alto, Calif., USA). The second dimensional chromatographic separation is carried out with a home-packed nanobored C18 column (75 um i.d×10 cm, 5 µm particles) directly into a pico-frit nanospray tip (New Objective, Wubrun, Mass., USA), operating at a flow rate of 200 nL/min with a 120 min gradient.

The LTQ is operated in a data-dependent mode by performing MS/MS scans for the 3 of the most intense peaks from each MS scan. For each experiment, ms/ms (dta) spectra of the 6 salt steps are combined into a single mascot generic file by a home-written program. Protein identification is achieved by searching the combined data against the IPI human protein database via an in-house Mascot server. The search parameters are: a maximum of 2 missed cleavages using trypsin; fixed modification is carbaminomethylation and variable modifications are oxidation of methionine and protein N-terminal acetylation. The mass tolerances are set to 2.0 and 0.8 Da for peptide precursor and fragment ions respectively. Protein identifications are accepted as true positive if two different peptides are found with score 50 or above. Since many growth factors and cytokines are small proteins/peptides and secreted in small amount, the corresponding MS/MS spectra will be weak and only one peptide per protein will be identified. For those peptides with Mascot score of between 20 and 50, manual validation of the MS/MS spectra is performed.

Bioinformatics

The validated proteins are collated by removing the background proteins identified in the non-conditioned medium. The IPI identifier of each protein is then converted to gene symbol by using the protein cross-reference table. Gene products are classified into the different biological processes or pathways of the GO classification system Gene Ontology (GO) classification on GeneSpring GX7.3 Expression Analysis (Agilent Technologies, Palo Alto, Calif.). and then comparing the frequency of genes in each process or pathway to that in the Genbank human genome database, those processes of pathways with significantly higher gene frequency (p<0.05) are assumed to be significantly modulated by the secretion of MSC.

qRT-PCR

Total RNA is extracted from HuES9.E1 cells with Trizol Reagent (Gibco-BRL) and purified over a spin column (Nucleospin RNA II System, Macherey-Nagel GmbH &Co., Düren, Germany) according to the manufacturers' protocol. 1 µg total RNA is converted to cDNA with random primers in a 50 µl reaction volume using a High Capacity cDNA Archive Kit (Applied Biosystems, Foster City, Calif., USA). The cDNA is diluted with distilled water to a volume of 100 µl. 1 µl is used for each primer set in a pathway-specific $RT^2$ Profiler PCR Arrays (SuperArray, Frederick, USA) according to the manufacturer's protocol. The plates used for the analysis are: Chemokines & Receptors PCR Array (cat. no. APH-022), NFkB Signaling Pathway PCR Array (cat. no. APH-025), Inflammatory Cytokines & Receptors PCR Array (cat. no. APH-011), Common Cytokine PCR Array (cat. no. APH-021), JAK/STAT Signaling Pathway PCR Array (cat. no. APH-039).

Example 8

Analysis of Proteome of Human ESC-derived MSCs (hESC-MSCs): Preparation of Conditioned Media (CM) and Non-Conditioned Media (NCM)

To ensure that there is minimal contamination of conditioned media by media supplements such as serum replacement media, HuES9.E1 MSCs are grown to about 80% confluency, washed three times with PBS, incubated overnight in a chemically defined media consisting of DMEM supplemented with ITS (insulin, transferrin and selenoprotein), 5 ng/ml FGF2, 5 ng/ml PDGF AB, glutamine-penicillin-streptomycin and β-mercaptoethanol. HuES9.E1 MSCs can be propagated in this minimal media for at least a week. The next day, the cell culture is again washed three times with PBS, and incubated with the fresh defined media.

Figure 6:
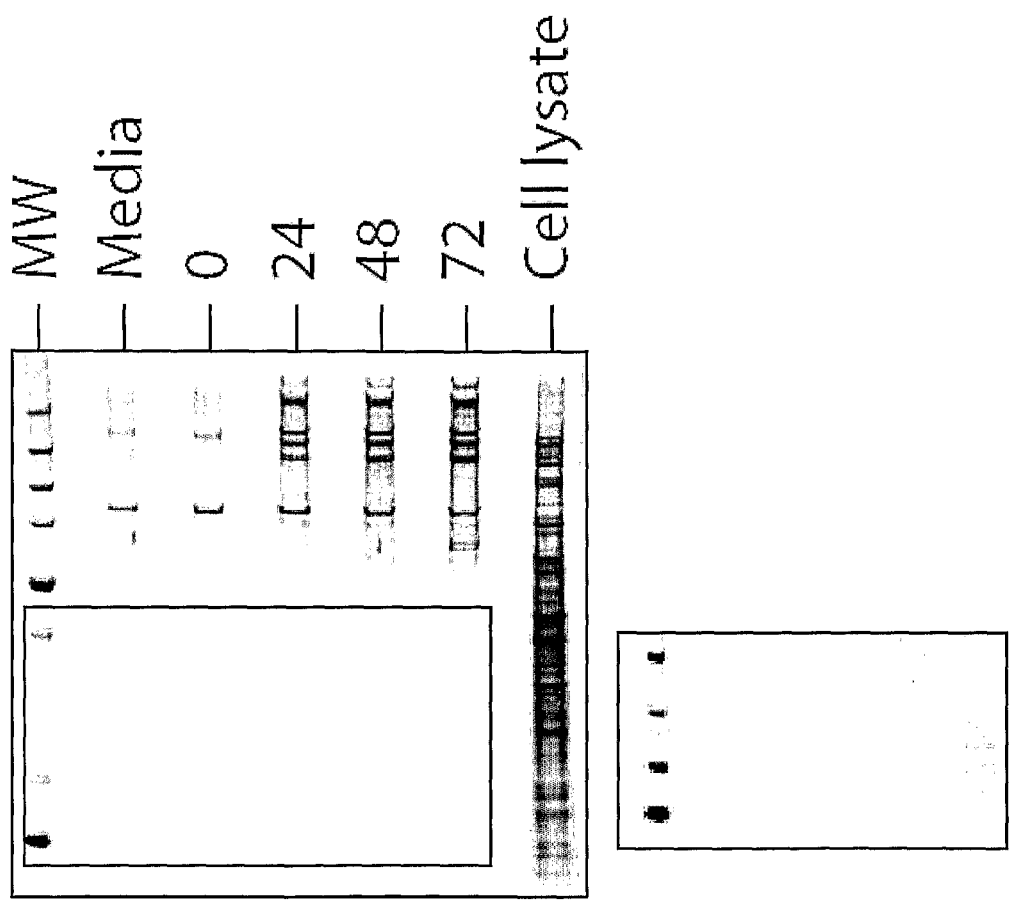
FIG. 6. Protein analysis of media conditioned by HuES9.E1 MSC culture. 80% confluent HuES9.E1 cell cultures are washed 3 times with PBS, cultured overnight in a chemically defined media consisting of DMEM media without phenol red and supplemented with ITS, 5 ng/ml FGF2, 5 ng/ml PDGF AB glutamine-penicillin-streptomycin and β-mercaptoethanol. The cultures are then rinsed three times with PBS and then replaced with fresh defined media. An aliquot of media are removed at 0, 24, 48 and 72 hours, centrifuged at 500×g and the supernatant is 0.2μ filtered. 10 μl of the media is separated on a 4-12% SDS-PAGE and silver-stained.

The media is collected after three days of conditioning. The conditioned media (CM) is always analyzed or processed in paralled with an equivalent volume of non-condtioned media (NCM). For LC MS/MS analysis, the media is concentrated ~10× before extensive dialysis against 0.9% saline as described in the materials and methods. The average protein concentration of concentrated CM and NCM are 98.0±17.9 µg/ml and 41.6±1.2 µg/ml (n=3), respectively. The conditioning of media by MSCs is monitored by running aliquots of the media on protein gels. Protein composition of the media increased in complexity with time (FIG. 6). The CM had a more complex protein composition than NCM.

Example 9

Analysis of Proteome of Human ESC-derived MSCs (hESC-MSCs): Analysis of MSC Conditioned Media by LC MS/MS and Antibody Array LC MS/MS analysis identified 250 proteins that are present in two independently prepared batches of CM, but not in a similarly processed NCM. These are:

1. IPI00021428 Actin, alpha skeletal muscle; 2. IPI00414057 Actin alpha 1 skeletal muscle protein; 3. IPI00008603 Actin, aortic smooth muscle; 4. IPI00021439 Actin, cytoplasmic 1; 5. IPI00023006 Actin, alpha cardiac; 6. IPI00021440 Actin, cytoplasmic 2; 7. IPI00025416 Actin, gamma-enteric smooth muscle; 8. IPI00479925 agrin; 9. IPI00015102 CD166 antigen precursor; 10. IPI00007423 Acidic leucine-rich nuclear phosphoprotein 32 family member B; 11. IPI00413331 36 kDa protein; 12. IPI00412577 34 kDa protein; 13. IPI00413506 33 kDa protein; 14. IPI00418169 Hypothetical protein DKFZp686P03159; 15. IPI00003815 Rho GDP-dissociation inhibitor 1; 16. IPI00004656 Beta-2-microglobulin precursor; 17. IPI00218042 Splice Isoform BMP1-5 of Bone morphogenetic protein 1 precursor; 18. IPI00009054 Splice Isoform BMP1-3 of Bone morphogenetic protein 1 precursor; 19. IPI00014021 Splice Isoform BMP1-1 of Bone morphogenetic protein 1 precursor; 20. IPI00218040 Splice Isoform BMP1-4 of Bone morphogenetic protein 1 precursor; 21. IPI00006980 Protein C14orf166; 22. IPI00296165 Complement C1r subcomponent precursor; 23. IPI00152540 OTTHUMP00000016748; 24. IPI00305064 Splice Isoform CD44 of CD44 antigen precursor; 25. IPI00297160 Hypothetical protein DKFZp451K1918; 26. IPI00293539 Splice Isoform 2 of Cadherin-11 precursor; 27. IPI00304227 Splice Isoform 1 of Cadherin-11 precursor; 28. IPI00386476 Cadherin 11, type 2, isoform 1 preproprotein; 29. IPI00024046 Cadherin-13 precursor;

30. IPI00290085 Neural-cadherin precursor; 31. IPI00029739 Splice Isoform 1 of Complement factor H precursor; 32. IPI00012011 Cofilin, non-muscle isoform; 33. IPI00007257 calsyntenin 1 isoform 2; 34. IPI00218539 Splice Isoform B of Collagen alpha-1(XI) chain precursor; 35. IPI00477350 Collagen, type XI, alpha 1; 36. IPI00329573 Splice Isoform Long of Collagen alpha-1(XII) chain precursor; 37. IPI00221384 Splice Isoform Short of Collagen alpha-1(XII) chain precursor; 38. IPI00400935 Collagen alpha-1(XVI) chain precursor; 39. IPI00297646 Collagen alpha-1(I) chain precursor; 40. IPI00164755 Prepro-alpha2(I) collagen precursor; 41. IPI00304962 Collagen alpha-2(I) chain precursor; 42. IPI00021033 Collagen alpha-1(III) chain precursor; 43. IPI00167087 COL3A1 protein; 44. IPI00021034 Collagen alpha-1 (IV) chain precursor; 45. IPI00479324 alpha 2 type IV collagen preproprotein; 46. IPI00306322 Collagen alpha-2(IV) chain precursor; 47. IPI00303313 Collagen alpha-1(V) chain precursor; 48. IPI00477611 184 kDa protein; 49. IPI00293881 COL5A2 protein; 50. IPI00018279 Collagen alpha-3(V) chain precursor; 51. IPI00291136 Collagen alpha-1(VI) chain precursor; 52. IPI00304840 Splice Isoform 2C2 of Collagen alpha-2(VI) chain precursor; 53. IPI00220613 Splice Isoform 2C2A of Collagen alpha-2(VI) chain precursor; 54. IPI00022200 alpha 3 type VI collagen isoform 1 precursor; 55. IPI00072918 alpha 3 type VI collagen isoform 4 precursor; 56. IPI00220701 Splice Isoform 2 of Collagen alpha-3(VI) chain precursor; 57. IPI00072917 alpha 3 type VI collagen isoform 3 precursor; 58. IPI00021828 Cystatin B; 59. IPI00007778 Di-N-acetylchitobiase precursor; 60. IPI00295741 Cathepsin B precursor;

61. IPI00299219 Protein CYR61 precursor; 62. IPI00514900 42 kDa protein; 63. IPI00333770 Similar to Dedicator of cytokinesis protein 10; 64. IPI00478332 Similar to Dedicator of cytokinesis protein 9; 65. IPI00000875 Elongation factor 1-gamma; 66. IPI00465248 Alpha-enolase; 67. IPI00013769 Alpha-enolase, lung specific; 68. IPI00216171 Gamma-enolase; 69. IPI00218803 Splice Isoform B of Fibulin-1 precursor; 70. IPI00296537 Splice Isoform C of Fibulin-1 precursor; 71. IPI00328113 Fibrillin-1 precursor; 72. IPI00019439 fibrillin 2 precursor; 73. IPI00385645 Splice Isoform 2 of Fibroblast growth factor 17 precursor; 74. IPI00216602 Splice Isoform 5 of Fibroblast growth factor receptor 2 precursor; 75. IPI00216604 Splice Isoform 8 of Fibroblast growth factor receptor 2 precursor; 76. IPI00034099 Hypothetical protein FLJ21918; 77. IPI00333541 Filamin-A; 78. IPI00302592 Filamin A, alpha; 79. IPI00339227 Hypothetical protein DKFZp68601166; 80. IPI00414283 Fibronectin precursor (FN) (Cold-insoluble globulin) (CIG). Splice isoform 3; 81. IPI00339225 Splice Isoform 5 of Fibronectin precursor; 82. IPI00339319 Splice Isoform 11 of Fibronectin precursor; 83. IPI00556632 Splice Isoform 12 of Fibronectin precursor; 84. IPI00411462 Hypothetical protein DKFZp686B18150; 85. IPI00029723 Follistatin-related protein 1 precursor; 86. IPI00005401 Polypeptide N-acetylgalactosaminyltransferase 5; 87. IPI00219025 Glutaredoxin-1; 88. IPI00171411 Golgi phosphoprotein 2; 89. IPI00026314 Gelsolin precursor;

90. IPI00219757 Glutathione S-transferase P; 91. IPI00027569 Heterogeneous nuclear ribonucleoprotein C-like 1; 92. IPI00003881 HNRPF protein; 93. IPI00442294 Splice Isoform 1 of Neurotrimin precursor; 94. IPI00003865 Splice Isoform 1 of Heat shock cognate 71 kDa protein; 95. IPI00037070 Splice Isoform 2 of Heat shock cognate 71 kDa protein; 96. IPI00220362 10 kDa heat shock protein, mitochondrial; 97. IPI00024284 Basement membrane-specific heparan sulfate proteoglycan core protein precursor; 98. IPI00297284 Insulin-like growth factor binding protein 2 precursor; 99. IPI00297284 Insulin-like growth factor binding protein 2 precursor; 100. IPI00029236 Insulin-like growth factor binding protein 5 precursor; 101. IPI00029236 Insulin-like growth factor binding protein 5 precursor; 102. IPI00029235 Insulin-like growth factor binding protein 6 precursor; 103. IPI00029235 Insulin-like growth factor binding protein 6 precursor; 104. IPI00016915 Insulin-like growth factor binding protein 7 precursor; 105. IPI00016915 Insulin-like growth factor binding protein 7 precursor; 106. IPI00328163 K-ALPHA-1 protein; 107. IPI00021396 Vascular endothelial growth factor receptor 2 precursor; 108. IPI00298281 Laminin gamma-1 chain precursor; 109. IPI00219219 Galectin-1; 110. IPI00023673 Galectin-3 binding protein precursor; 111. IPI00021405 Splice Isoform A of Lamin-A/C; 112. IPI00216953 Splice Isoform ADelta10 of Lamin-A/C; 113. IPI00180173 PREDICTED: similar to tropomyosin 4; 114. IPI00401614 PREDICTED: similar to FKSG30; 115. IPI00374397 PREDICTED: similar to tropomyosin 4; 116. IPI00374732 PREDICTED: similar to PPIA protein; 117. IPI00402104 PREDICTED: similar to peptidylprolyl isomerase A isoform 1; cyclophilin A; peptidyl-pro; 118. IPI00455415 PREDICTED: similar to Heterogeneous nuclear ribonucleoprotein C-like dJ845O24.4; 119. IPI00454722 PREDICTED: similar to Phosphatidylethanolamine-binding protein; 120. IPI00454852 PREDICTED: similar to Teratocarcinoma-derived growth factor 1;

121. IPI00002802 Protein-lysine 6-oxidase precursor; 122. IPI00410152 latent transforming growth factor beta binding protein 1 isoform LTBP-1L; 123. IPI00220249 Latent transforming growth factor beta-binding protein, isoform 1L precursor; 124. IPI00220249 Latent transforming growth factor beta-binding protein, isoform 1L precursor"; 125. IPI00410152 latent transforming growth factor beta binding protein 1 isoform LTBP-1L; 126. IPI00020986 Lumican precursor; 127. IPI00291006 Malate dehydrogenase, mitochondrial precursor; 128. IPI00005707 Macrophage mannose receptor 2 precursor; 129. IPI00020501 Myosin-11; 130. IPI00019502 Myosin-9; 131. IPI00604620 Nucleolin; 132. IPI00220740 Splice Isoform 2 of Nucleophosmin; 133. IPI00219446 Phosphatidylethanolamine-binding protein; 134. IPI00299738 Procollagen C-endopeptidase enhancer 1 precursor; 135. IPI00015902 Beta platelet-derived growth factor receptor precursor; 136. IPI00216691 Profilin-1; 137. IPI00169383 Phosphoglycerate kinase 1; 138. IPI00219568 Phosphoglycerate kinase, testis specific; 139. IPI00296180 Urokinase-type plasminogen activator precursor; 140. IPI00215943 Splice Isoform 3 of Plectin 1; 141. IPI00215942 Splice Isoform 2 of Plectin 1;

142. IPI00014898 Splice Isoform 1 of Plectin 1; 143. IPI00398777 plectin 1 isoform 8; 144. IPI00398776 plectin 1 isoform 7; 145. IPI00186711 plectin 1 isoform 6; 146. IPI00420096 plectin 1 isoform 3; 147. IPI00398779 plectin 1 isoform 11; 148. IPI00398778 plectin 1 isoform 10; 149. IPI00398002 plectin 1 isoform 1; 150. IPI00419585 Peptidyl-prolyl cis-trans isomerase A;

151. IPI00472718 peptidylprolyl isomerase A isoform 2; 152. IPI00000874 Peroxiredoxin-1; 153. IPI00024915 Peroxiredoxin-5, mitochondrial precursor; 154. IPI00375306 peroxiredoxin 5 precursor, isoform b; 155. IPI00012503 Splice Isoform Sap-mu-0 of Proactivator polypeptide precursor; 156. IPI00374179 proteasome activator subunit 1 isoform 2; 157. IPI00030154 Proteasome activator complex subunit 1; 158. IPI00168812 PTK7 protein tyrosine kinase 7 isoform d precursor; 159. IPI00419941 PTK7 protein tyrosine kinase 7 isoform a precursor; 160. IPI00003590 Quiescin Q6, isoform a; 161. IPI00015916 Bone-derived growth factor (Fragment); 162. IPI00015916 Bone-derived growth factor; 163. IPI00298289 Splice Isoform 2 of Reticulon-4; 164. IPI00021766 Splice Isoform 1 of Reticulon-4; 165. IPI00013895 Calgizzarin; 166. IPI00010402 Hypothetical protein; 167. IPI00218733 Superoxide dismutase; 168. IPI00014572 SPARC precursor; 169. IPI00005614 Splice Isoform Long of Spectrin beta chain, brain 1; 170. IPI00008780 Stanniocalcin-2 precursor; 171. IPI00301288 SEL-OB protein; 172. IPI00216138 Transgelin; 173. IPI00018219 Transforming growth factor-beta-induced protein ig-h3 precursor; 174. IPI00304865 transforming growth factor, beta receptor III"; 175. IPI00296099 Thrombospondin-1 precursor; 176. IPI00032292 Metalloproteinase inhibitor 1 precursor; 177. IPI00027166 Metalloproteinase inhibitor 2 precursor; 178. IPI00220828 Thymosin beta-4; 179. IPI00180240 thymosin-like 3;

180. IPI00299633 OTTHUMP00000031270 (Fragment); 181. IPI00465028 Triosephosphate isomerase 1 variant (Fragment); 182. IPI00451401 Splice Isoform 2 of Triosephosphate isomerase; 183. IPI00010779 Tropomyosin 4; 184. IPI00216975 Splice Isoform 2 of Tropomyosin alpha-4 chain; 185. IPI00180675 Tubulin alpha-3 chain; 186. IPI00218343 Tubulin alpha-6 chain; 187. IPI00216298 Thioredoxin; 188. IPI00472175 CDNA FLJ46672 fis, clone TRACH3009008, highly similar to Thioredoxin reductase; 189. IPI00450472 Ubiquitin-conjugating enzyme E2I; 190. IPI00018352 Ubiquitin carboxyl-terminal hydrolase isozyme L1; 191. IPI00010207 Ubiquitin-fold modifier 1 precursor; 192. IPI00260630 URB; 193. IPI00021263 14-3-3 protein zeta/delta; 194. IPI00642991 Hypothetical protein DKFZp686F10164; 195. IPI00470919 Hypothetical protein DKFZp686K08164; 196. IPI00719088 collagen, type VI, alpha 1 precursor; 197. IPI00654685 Similar to SPARC precursor; 198. IPI00641961 Collagen, type XII, alpha 1; 199. IPI00645849 Extracellular matrix protein 1; 200. IPI00554786 Thioredoxin reductase 1; 201. IPI00645018 Plasminogen activator, urokinase; 202. IPI00552339 Tissue inhibitor of metalloproteinase 1; 203. IPI00642997 Actin, cytoplasmic 2; 204. IPI00719778 Similar to Annexin A2; 205. IPI00647915 Transgelin 2; 206. IPI00552815 Collagen, type V, alpha 1; 207. IPI00552981 CDNA PSEC0266 fis, clone NT2RP3003649, highly similar to Homo sapiens fibulin-1D mRNA; 208. IPI00180776 29 kDa protein; 209. IPI00552416 Filamin A, alpha;

210. IPI00640698 Actin, gamma-enteric smooth muscle; 211. IPI00514530 Actin, alpha 1, skeletal muscle; 212. IPI00556442 Insulin-like growth factor binding protein 2 variant (Fragment); 213. IPI00513782 Gelsolin; 214. IPI00478731 29 kDa protein; 215. IPI00396479 24 kDa protein; 216. IPI00334627 39 kDa protein; 217. IPI00555762 PTK7 protein tyrosine kinase 7 isoform a variant (Fragment); 218. IPI00658202 97 kDa protein; 219. IPI00006273 CYR61 protein; 220. IPI00719405 TMSL6 protein; 221. IPI00658096 Thymosin beta-4; 222. IPI00376163 5 kDa protein; 223. IPI00556217 Fibrillin 1 variant (Fragment); 224. IPI00514817 Similar to Lamin A/C; 225. IPI00644087 Progerin; 226. IPI00655812 Rhabdomyosarcoma antigen MU-RMS-40.12; 227. IPI00604517 Similar to Nucleolin; 228. IPI00444262 CDNA FLJ45706 fis, clone FEBRA2028457, highly similar to Nucleolin; 229. IPI00412473 Protein; 230. IPI00414489 Protein; 231. IPI00411463 Protein; 232. IPI00556415 Transgelin variant (Fragment); 233. IPI00718825 Calmodulin; 234. IPI00478156 17 kDa protein; 235. IPI00386621 CALM3 protein; 236. IPI00647001 Acidic; 237. IPI00642650 Similar to Stanniocalcin 2 precursor; 238. IPI00641471 Collagen-like protein; 239. IPI00514669 SH3 domain binding glutamic acid-rich protein like 3; 240. IPI00719422 Triosephosphate isomerase (Fragment); 241. IPI00003734 Putative S100 calcium-binding protein H_NH0456N16.1; 242. IPI00029574 11 kDa protein; 243. IPI00641047 Gelsolin; 244. IPI00647556 Gelsolin; 245. IPI00654821 hypothetical protein LOC54845 isoform 1; 246. IPI00647572 Dickkopf related protein-3 precursor; 247. IPI00639879 Similar to Cytokinesis protein sepA; 248. IPI00657746 Similar to Dedicator of cytokinesis protein 8; 249. IPI00555993 Vascular endothelial growth factor receptor 3 variant; 250. IPI00552545 Dedicator of cytokinesis protein 8.

Together, these 250 proteins are encoded by 132 unique known genes: ACTA1; COL5A2; HSPA8; PSAP; ACTA2; COL5A3; HSPE1; PSME1; ACTB; COL6A1; HSPG2; PTK7; ACTC; COL6A2; IGFBP2; QSCN6; ACTG1; COL6A3; IGFBP5; RTN4; ACTG2; CSTB; IGFBP6; S100A11; AGRN; CTBS; IGFBP7; SH3BGRL3; ALCAM; CTSB; K-ALPHA-1; SOD1; ANP32B; CYR61; KDR; SPARC; ANXA2; DOCK10; LAMC1; SPTBN1; ARHGDIA; DOCK8; LGALS1; STC2; B2M; ECM1; LGALS3BP; SVEP1; BMP1; EEF1G; LMNA; TAGLN; C14orf166; ENO1; LOX; TAGLN2; C1R; ENO1B; LTBP1; TGFBI; CALM1; ENO2; LUM; TGFBR3; CD109; FBLN1; MDH2; THBS1; CD44; FBN1; MRC2; TIMP1; CDH11; FBN2; MYH11; TIMP2; CDH13; FGF17; MYH9; TMSB4X; CDH2; FGFR2; NCL; TMSL3; CFH/HF1; FLJ21918; NPM1; TMSL6; CFL1; FLNA; PBP; TPI1; CLSTN1; FN1; PCOLCE; TPM4; COL11A1; FSTL1; PDGFRB; TUBA3; COL12A1; GALNT5; PFN1; TUBA6; COL16A1; GLRX; PGK1; TXN; COL1A1; GOLPH2; PGK2; TXNRD1; COL1A2; GSN; PLAU; UBE2I; COL3A1; GSTP1; PLEC1; UCHL1; COL4A1; HNRPCL1; PPIA; UFM1; COL4A2; HNRPF; PRDX1; URB; COL5A1; HNT; PRDX5; YWHAZ.

There are 32 unknown proteins: IPI00642991 Hypothetical protein DKFZp686F10164; IPI00470919 Hypothetical protein DKFZp686K08164; IPI00654685 Similar to SPARC precursor; IPI00719778 Similar to Annexin A2; IPI00552981 CDNA PSEC0266 fis, clone NT2RP3003649, highly similar to Homo sapiens fibulin-1D mRNA; IPI00180776 29 kDa protein; IPI00478731 29 kDa protein; IPI00396479 24 kDa protein; IPI00334627 39 kDa protein; IPI00658202 97 kDa protein; IPI00376163 5 kDa protein; IPI00514817 Similar to Lamin A/C; IPI00644087 Progerin; IPI00655812 Rhabdomyosarcoma antigen MU-RMS-40.12; IPI00604517 Similar to Nucleolin; IPI00444262 CDNA FLJ45706 fis, clone FEBRA2028457, highly similar to Nucleolin; IPI00412473 Protein; IPI00414489 Protein; IPI00411463 Protein; IPI00478156 17 kDa protein; IPI00386621 CALM3 protein; IPI00647001 Acidic; IPI00642650 Similar to Stanniocalcin 2 precursor; IPI00641471 Collagen-like protein; IPI00514669 SH3 domain binding glutamic acid-rich protein like 3; IPI00003734 Putative S100 calcium-binding protein H_NH0456N16.1; IPI00029574 11 kDa protein; IPI00654821 hypothetical protein LOC54845 isoform 1; IPI00647572 Dickkopf related protein-3 precursor; IPI00639879 Similar to Cytokinesis protein sepA; IPI00657746 Similar to Dedicator of cytokinesis protein 8; IPI00555993 Vascular endothelial growth factor receptor 3 variant.

The MSCs described in this document can therefore be used as sources of any or all of these proteins, or any proteins or other molecules which are secreted or expressed by them.

Figure 7:
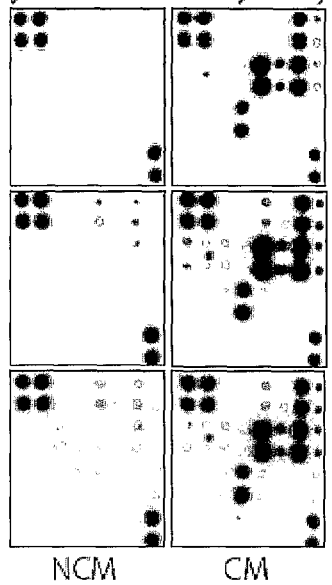
FIG. 7. Antibody array. One ml of conditioned (CM) or non-conditoned media (NCM) is incubated with a RayBio® Cytokine Antibody Arrays according to manufacturer's instruction (RayBio Norcross, Ga.). The antibody map for each array is listed in the Examples. Binding of ligands to specific antibody is visualized using HRP-based chemiluminescence assay. Different exposures of each membrane is analysed. An antigen is scored as present if a signal is present on the membrane hybridized with CM but absent on that hybridized with NCM. Data from analysis of 4 independent batches of CM and NCM is summarized in the Examples.
Figure 7:
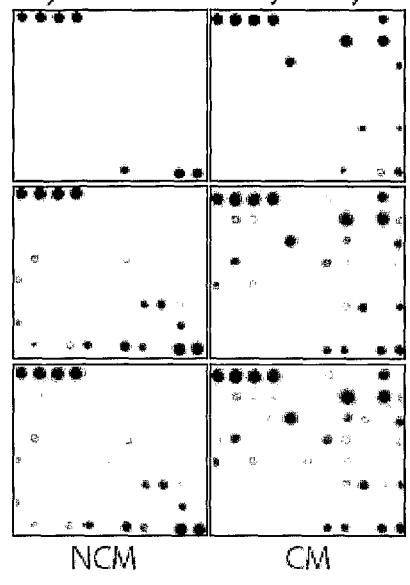
Figure 7:
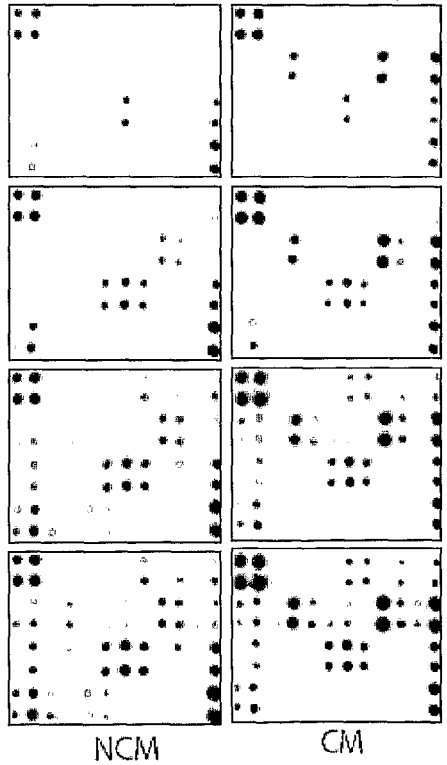
Figure 7:
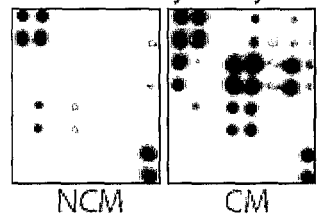
Figure 7:
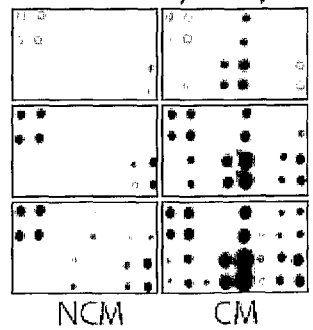

MSCs have been shown to secrete a broad spectrum of cytokines and growth factors that affect cells on their vicinity[8]. Many of these factors are small molecules that are not easily detectable during shot-gun LC MS/MS analysis. Therefore, the CM and NCM are also analyzed by hybridization to 5 different antibody arrays that together carried antibodies against 101 cytokines/growth factors (See also FIG. 7).

Layout of Antibody Arrays

| | RayBio ® Angiogenesis array I | | | | | | | |
|---|---|---|---|---|---|---|---|---|
| | A | B | C | D | E | F | G | H |
| 1 | POS | POS | NEG | NEG | Angiogenin | EGF | ENA-78 | b FGF |
| 2 | POS | POS | NEG | NEG | Angiogenin | EGF | ENA-78 | b FGF |
| 3 | GRO | IFN-□ | IGF-I | IL-6 | IL-8 | LEPTIN | MCP-1 | PDGF-BB |
| 4 | GRO | IFN-□ | IGF-I | IL-6 | IL-8 | LEPTIN | MCP-1 | PDGF-BB |
| 5 | PIGF | RANTES | TGF-□1 | TIMP-1 | TIMP-2 | Thrombopoietin | VEGF | VEGF-D |
| 6 | PIGF | RANTES | TGF-□1 | TIMP-1 | TIMP-2 | Thrombopoietin | VEGF | VEGF-D |
| 7 | BLANK | BLANK | BLANK | BLANK | BLANK | BLANK | Neg | POS |
| 8 | BLANK | BLANK | BLANK | BLANK | BLANK | BLANK | Neg | POS |

| | RayBio ® Human Chemokine Antibody Array I | | | | | | | | | | | |
|---|---|---|---|---|---|---|---|---|---|---|---|---|
| | A | B | C | D | E | F | G | H | I | J | K | L |
| 1 | POS | POS | NEG | NEG | BLC | CCL28 | Ckβ8-1 | CTACK | CXCL16 | ENA-78 | Eotaxin | Eotaxin-2 |
| 2 | POS | POS | NEG | NEG | BLC | CCL28 | Ckβ8-1 | CTACK | CXCL16 | ENA-78 | Eotaxin | Eotaxin-2 |
| 3 | Eotaxin-3 | Fractalkine | GCP-2 | GRO | GROα | HCC-4 | I-309 | I-TAC | IL-8 | IP-10 | Lymphotactin | MCP-1 |
| 4 | Eotaxin-3 | Fractalkine | GCP-2 | GRO | GROα | HCC-4 | I-309 | I-TAC | IL-8 | IP-10 | Lymphotactin | MCP-1 |
| 5 | MCP-2 | MCP-3 | MCP-4 | MDC | MIG | MIP-1α | MIP-1β | MIP-1δ | MIP-3α | MIP-3β | MPIF-1 | NAP 2 |
| 6 | MCP-2 | MCP-3 | MCP-4 | MDC | MIG | MIP-1α | MIP-1β | MIP-1δ | MIP-3α | MIP-3β | MPIF-1 | NAP 2 |
| 7 | PARC | RANTES | SDF-1α | SDF-1β | TARC | TECK | BLANK | BLANK | BLANK | BLAND | BLANK | POS |
| 8 | PARC | RANTES | SDF-1α | SDF-1β | TARC | TECK | BLANK | BLANK | BLANK | BLAND | BLANK | POS |

| | RayBio ® Matrix Metalloproteinases Antibody Array I | | | | | | | |
|---|---|---|---|---|---|---|---|---|
| | A | B | C | D | E | F | G | H |
| 1 | POS | POS | NEG | NEG | MMP-1 | MMP-2 | MMP-3 | MMP-8 |
| 2 | POS | POS | NEG | NEG | MMP-1 | MMP-2 | MMP-3 | MMP-8 |
| 3 | MMP-9 | MMP-10 | MMP-13 | TIMP-1 | TIMP-2 | TIMP-3 | TIMP-4 | POS |
| 4 | MMP-9 | MMP-10 | MMP-13 | TIMP-1 | TIMP-2 | TIMP-3 | TIMP-4 | POS |

| | RayBio ® Human Cytokine Antibody Array I | | | | | | | |
|---|---|---|---|---|---|---|---|---|
| | A | B | C | D | E | F | G | H |
| 1 | POS | POS | NEG | NEG | GCSF | GM-CSF | GRO | GROα |
| 2 | POS | POS | NEG | NEG | GCSF | GM-CSF | GRO | GROα |
| 3 | IL-1α | IL-2 | IL-3 | IL-5 | IL-6 | IL-7 | IL-8 | IL-10 |
| 4 | IL-1α | IL-2 | IL-3 | IL-5 | IL-6 | IL-7 | IL-8 | IL-10 |
| 5 | IL-13 | IL-15 | IFN-γ | MCP-1 | MCP-2 | MCP-3 | MIG | RANTES |
| 6 | IL-13 | IL-15 | IFN-γ | MCP-1 | MCP-2 | MCP-3 | MIG | RANTES |
| 7 | TGF-β1 | TNF-α | TNF-β | BLANK | BLANK | BLANK | BLANK | POS |
| 8 | TGF-β1 | TNF-α | TNF-β | BLANK | BLANK | BLANK | BLANK | POS |

| RayBio ® Human Cytokine Antibody Array V | | | | | | | | | | | |
|---|---|---|---|---|---|---|---|---|---|---|---|
| A | B | C | D | E | F | G | H | I | J | K | L |
| 1 POS | POS | POS | POS | NEG | NEG | ENA-78 | GCSF | GM-CSF | GRO | GRO-α | POS |
| 2 I-309 | IL-1α | IL-1β | IL-2 | IL-3 | IL-4 | IL-5 | IL-6 | IL-7 | IL-8 | IL-10 | I-309 |
| 3 IL-12 p40p70 | IL-13 | IL-15 | IFN-γ | MCP-1 | MCP-2 | MCP-3 | MCSF | MDC | MIG | MIP-1β | IL-12 p40p70 |
| 4 MIP-1δ | RANTES | SCF | SDF-1 | TARC | TGF-β1 | TNF-α | TNF-β | EGF | IGF-1 | Angiogenin | MIP-1δ |
| 5 Oncostatin M | Thrombopoietin | VEGF | PDGF-BB | LEPTIN | BDNF | BLC | Ckβ8-1 | Eotaxin | Eotaxin-2 | Eotaxin-3 | Oncostatin M |
| 6 FGF-4 | FGF-6 | FGF-7 | FGF-9 | Flt-3 Ligand | Fractalkine | GCP-2 | GDNF | HGF | IGFBP-1 | IGFBP-2 | FGF-4 |
| 7 IGFBP-3 | IGFBP-4 | IL-16 | IP-10 | LIF | LIGHT | MCP-4 | MIF | MIP-3α | NAP-2 | NT-3 | IGFBP-3 |
| 8 NT-4 | Osteoprotegerin | PARC | PIGF | TGF-β2 | TGF-β3 | TIMP-1 | TIMP-2 | NEG | POS | POS | NT-4 |

72 of the cytokines/growth factors are found to be reproducibly secreted by HuES9.E1 MSCs in at least three of four independently prepared CM and not in NCM. 72 proteins identified by antibody array (Name GeneSymbol GeneID): 1. MDC ADAM11 GI_11496997-A; 2. Angiogenin ANG GI_42716312-S; 3. BDNF BDNF GI_34106709-A; 4. I-309 CCL11 GI_4506832-S; 5. Eotaxin CCL11 GI_22538399; 6. MIP-1δ CCL15 GI_34335180-A; 7. HCC-4 CCL16 GI_22538800; 8. MCP-1 CCL2 GI_22538812-S; 9. Ckβ8-1 CCL23 GI_22538807-A; 10. Eotaxin-2 CCL24 GI_22165426-S; 11. Eotaxin-3 CCL26 GI_22547151-S; 12. RANTES CCL5 GI_22538813; 13. MCP-3 CCL7 GI_13435401-S; 14. MCP-2 CCL8 GI_22538815-S; 15. MCSF CSF1 GI_27262666-I; 16. GM-CSF CSF2 GI_27437029-S; 17. GCSF CSF3 GI_27437048; 18. Fractalkine CX3CL1 GI_4506856-S; 19. GRO-a CXCL1 GI_4504152-S; 20. I-TAC CXCL11 GI_14790145-S; 21. SDF-1 CXCL12 GI_40316923; 22. BLC CXCL13 GI_5453576-S; 23. ENA-78 CXCL5 GI_41872613-S; 24. IP-10 CXCR3 GI_4504098-S; 25. EGF EGF GI_6031163-S; 26. FGF-4 FGF4 GI_4503700; 27. FGF-6 FGF6 GI_10337586; 28. FGF-7 FGF7 GI_15147344; 29. FGF-9 FGF9 GI_4503706-S; 30. Flt 3 Ligand FLT3LG GI_38455415-S; 31. GDNF GDNF GI_40549410; 32. GCP-2 GOLGA4 GI_45359854-S; 33. HGF HGF GI_33859834-S; 34. IFN-γ IFNG GI_10835170-S; 35. IGF-I IGF1 GI_19923111-S; 36. IGFBP-1 IGFBP1 GI_4504614-S; 37. IGFBP-2 IGFBP2 GI_10835156-S; 38. IGFBP-4 IGFBP4 GI_10835020-S; 39. IL-10 IL10 GI_24430216-S; 40. IL-12p40p70 IL12B GI_24497437-S; 41. IL-13 IL13 GI_26787977-S; 42. IL-16 IL16 GI_27262654-A; 43. IL-1a IL1A GI_27894329-S; 44. IL-1β IL1B GI_27894305-S; 45. IL-2 IL2 GI_28178860-S; 46. IL-3 IL3 GI_28416914-S; 47. IL-6 IL6 GI_10834983-S; 48. IL-7 IL7 GI_28610152-S; 49. IL-8 IL8 GI_28610153-S; 50. SCF KITLG GI_4580419-A; 51. LEPTIN LEP GI_4557714-S; 52. LIF LIF GI_6006018-S; 53. MIF MIF GI_4505184-S; 54. MMP-1 MMP1 GI_13027798-S; 55. MMP-10 MMP10 GI_4505204-S; 56. MMP-13 MMP13 GI_13027796-S; 57. MMP 3 MMP3 GI_13027803-S; 58. MMP-9 MMP9 GI_4826835-S; 59. PARC PARC GI_24307990; 60. PDGF-BB PDGFB GI_15451785-A; 61. PIGF PIGF GI_27894289-A; 62. TGF-β1 TGFB1 GI_10863872; 63. TGF-β2 TGFB2 GI_4507462-S; 64. Thrombopoietin THPO GI_40805871-S; 65. TIMP-1 TIMP1 GI_4507508-S; 66. TIMP-2 TIMP2 GI_9257247-S; 67. TIMP-3 TIMP3 GI_21536431-S; 68. TIMP-4 TIMP4 GI_4507514-S; 69. TNF-α TNF GI_25952110; 70. Osteoprotegerin TNFRSF11B GI_22547122-S; 71. VEGF VEGF GI_30172563-S; 72. Lymphotactin XCL1 GI_4506852-S.

29 proteins not detected by antibody array (Name GeneSymbol GeneID): b FGF CCL23 GI_22538807-A; MCP-4 CCL13 GI_22538799-S; TARC CCL17 GI_22538801-S; MIP-3b CCL19 GI_22165424-S; MIP-3a CCL20 GI_4759075-S; MPIF-1 CCL23 GI_22538807-A; TECK CCL25 GI_22538797-A; CTACK CCL27 GI_22165428-S; CCL28 CCL28 GI_22538810-A; MIP-1b CCL4 GI_4506844-S; SDF-1a CXCL12 GI_40316923-I; SDF-1b CXCL12 GI_40316923-I; CXCL16 CXCL16 GI_11545764-S; MIG CXCL9 GI_4505186-S; MIP-1a CXCR6 GI_5730105-S; IGFBP-3 IGFBP3 GI_19923110-S; IL-15 IL15 GI_26787979-A; IL-4 IL4 GI_27477091-A; IL-5 IL5 GI_28559032-S; TNF-b LTA GI_6806892-S; MMP-2 MMP2 GI_11342665-S; MMP-8 MMP8 GI_4505220-S; NAP-2 NAP1L4 GI_21327711-S; NT-3 NTF3 GI_45359869-S; NT-4 NTF5 GI_34328933-S; Oncostatin M OSM GI_28178862-S; TGF-b1 TGFB1 GI_10863872-S; LIGHT TNFSF14 GI_25952146-A; VEGF-D VEGFD GI_19924297-S.

However, only 3 gene products, namely IGFBP2, TIMP1 and TIMP2 are also detected by LC MS/MS analysis, possibly because many of cytokines and growth factors are small molecules and are not detectable during conventional LC MS/MS analysis.

The lists of 132 and 72 gene products identified by LC MS/MS and antibody array analysis respectively have 3 common genes, namely IGFBP2, TIMP1 and TIMP2. Therefore in the final tally, a total of 201 unique gene products are identified (Table E2 below).

TABLE E2

Alphabetical list of 201 unique gene products identified by LC-MS/MS and antibody array. The proteins identified by LC-MS/MS and antibody array are combined and represented by their gene symbol. Transcript level for each gene is assessed using a high throughput Illumina BeadArray.

ACTA1
ACTA2
ACTB
ACTC
ACTG1
ACTG2
ADAM11
AGRN
ALCAM
ANG
ANP32B
ANXA2
ARHGDIA
B2M
BDNF*
BMP1

TABLE E2-continued

Alphabetical list of 201 unique gene products identified by LC-MS/MS and antibody array. The proteins identified by LC-MS/MS and antibody array are combined and represented by their gene symbol. Transcript level for each gene is assessed using a high throughput Illumina BeadArray.

C14orf166
C1R
CALM1
CCL1
CCL2
CCL5
CCL7
CCL8
CCL11
CCL15
CCL16
CCL23
CCL24
CCL26
CD44
CD109
CDH2
CDH11
CDH13
CFH/HF1
CFL1
CLSTN1
COL1A1
COL1A2
COL3A1
COL4A1
COL4A2
COL5A1
COL5A2
COL5A3
COL6A1
COL6A2
COL6A3
COL11A1
COL12A1
COL16A1
CSF1*
CSF2*
CSF3*
CSTB
CTBS
CTSB
CX3CL1*
CXCL1*
CXCL5*
CXCL11*
CXCL12*
CXCL13†
CXCR3*
CYR61
DOCK8
DOCK10
ECM1
EEF1G
EGF
ENO1
ENO1B
ENO2
FBLN1
FBN1
FBN2
FGF4
FGF6
FGF7
FGF9
FGF17
FGFR2
FLJ21918
FLNA
FLT3LG
FN1
FSTL1
GALNT5
GDNF

TABLE E2-continued

Alphabetical list of 201 unique gene products identified by LC-MS/MS and antibody array. The proteins identified by LC-MS/MS and antibody array are combined and represented by their gene symbol. Transcript level for each gene is assessed using a high throughput Illumina BeadArray.

GLRX
GOLGA4
GOLPH2
GSN
GSTP1
HGF
HNRPCL1
HNRPF
HNT
HSPA8
HSPE1
HSPG2
IFNG†
IGF1
IGFBP1
IGFBP2
IGFBP4
IGFBP5
IGFBP6
IGFBP7
IL1A*
IL1B*
IL2*
IL3*
IL6*
IL7*
IL8*
IL10*
IL12B*
IL13*
IL16*
k-ALPHA-1
KDR
KITLG
LAMC1
LEP
LGALS1
LGALS3BP
LIF
LMNA
LOX
LTBP1
LUM
MDH2
MIF*
MMP1
MMP3*
MMP9
MMP10
MMP13
MRC2
MYH11
MYH9
NCL
NPM1
PARC
PBP
PCOLCE
PDGFB
PDGFRB
PFN1
PGK1
PGK2
PIGF
PLAU
PLEC1
PPIA
PRDX1
PRDX5
PSAP
PSME1
PTK7
QSCN6
RTN4

TABLE E2-continued

Alphabetical list of 201 unique gene products identified by LC-MS/MS and antibody array. The proteins identified by LC-MS/MS and antibody array are combined and represented by their gene symbol. Transcript level for each gene is assessed using a high throughput Illumina BeadArray.

S100A11
SH3BGRL3
SOD1
SPARC
SPTBN1
STC2
SVEP1
TAGLN
TAGLN2
TGFB1
TGFB2*
TGFBI*
TGFBR3
THBS1
THPO
TIMP1
TIMP2
TIMP3
TIMP4
TMSB4X
TMSL3
TMSL6
TNF*
TNFRSF11B*
TPI1
TPM4
TUBA3
TUBA6
TXN
TXNRD1
UBE2I
UCHL1
UFM1
URB
VEGF†
XCL1
YWHAZ 29 of these gene products namely ENA-78, FGF-4, FGF-7, FGF-9, GCP-2, G-CSF, GM-CSF, GRO-a, HCC-4, HGF, IGFBP-1, IGFBP-2, IGFBP-4, IL-1β, IL-6, IL-8, IP-10, LIF, MCP-1, MCSF, MIF, Osteoprotegerin, PARC, PIGF, SCF, TGF-β2, TIMP-1, TIMP-2, VEGF have been previously reported to be secreted by adult tissue derived MSCs (13, 16, 19-21). Four other proteins that are reported to be secreted bu adult tissue derived MSCs, namely IGFBP-3, MIP-3α, Oncostatin M and TGF-β3 (see above) are not present in our list of 201 gene products.

Example 10

Analysis of Proteome of Human ESC-derived MSCs (hESC-MSCs): Verification by Genome Wide-Gene Expression Analysis Comparison of the 201 gene products to a genome-wide gene expression profile of the hESC-MSCs generated by hybridizing total RNA to a Illumina BeadArray revealed that 134 or 67% of the gene products had gene transcript levels that are present at above the limit of detection (LOD) with a 99% confidence (Table E2). While 115 or 88% of the 132 gene products identified by LC MS/MS had detectable transcript levels (Table E2), 27 or 38% of the 72 gene products identified by antibody array had detectable transcript levels and 45 or 62% had no detectable transcript level (Table E2). Probes for two of the gene products, ENO1B and SVEP1 are not present on the Illumina BeadArray. It is possible that transcript levels for most of the 72 gene may be too low in abundance for detection by Illumina BeadArray as mRNAs encoding for cytokines/chemokines are known to contain AU-rich elements that caused rapid degradation of the mRNA during translation (22,23).

More sensitive qRT-PCR assays are therefore performed. 42 of the 72 gene products are randomly selected and tested. 36 or 86% of the 42 gene products have detectable transcript levels as defined as having a normalized $C_t$ value of <35 (Table E3 below). This frequency is similar to 88% frequency observed for gene products identified by LC MS/MS and whose gene transcripts are detectable by Illumina BeadArray. In addition, all 15 that have detectable transcript levels by Illumina BeadArray, also have detectable transcript levels by qRT-PCR (Table E3). 21 of 27 (78%) gene products that did not have detectable transcript levels by Illumina BeadArray have transcript level detectable by qRT-PCR (Table E3).

TABLE E3

Quantitative RT-PCR assay for the presence of transcripts. 42 of the 72 gene producits identified by antibody array are randomly selected for qRT-PCR analysis. 12 gene products have transcript levels that are above the limit of detection (LOD) at 99% confidence on the Illumina BeadArray, a high throughput genome-wide gene expression assay. The $C_t$ value for each gene is normalized against β-actin.

|    | Symbol | Illumina BeadArray | Normalized $C_t$ |
|----|--------|--------------------|-----------------|
| 1. | BDNF | >LOD | 13.38 |
| 2. | CCL2 | >LOD | 11.28 |
| 3. | CCL7 | >LOD | 17.35 |
| 4. | CCL8 | >LOD | 30.28 |
| 5. | CXCL1 | >LOD | 14.09 |
| 6. | CXCL12 | >LOD | 16.83 |
| 7. | CXCL5 | >LOD | 19.93 |
| 8. | IL1A | >LOD | 16.6 |
| 9. | IL1B | >LOD | 11.44 |
| 10 | IL6 | >LOD | 18.92 |
| 11 | IL8 | >LOD | 8.53 |
| 12 | MIF | >LOD | 16.23 |
| 13 | MMP3 | >LOD | 15.96 |
| 14 | TGFB2 | >LOD | 15.16 |
| 15 | TNFRSF11B | >LOD | 12.28 |
| 16 | CCL1 | <LOD | 34.67 |
| 17 | CCL11 | <LOD | 26.13 |
| 18 | CCL23 | <LOD | 37.33 |
| 19 | CCL24 | <LOD | 10.82 |
| 20 | CCL26 | <LOD | 30.38 |
| 21 | CCL5 | <LOD | 27.97 |
| 22 | CSF1 | <LOD | 14.35 |
| 23 | CSF2 | <LOD | 23.92 |
| 24 | CSF3 | <LOD | 32.47 |
| 25 | CX3CL1 | <LOD | 25.04 |
| 26 | CXCL11 | <LOD | 22.38 |
| 27 | CXCR3 | <LOD | 28.41 |
| 28 | IL10 | <LOD | 27.4 |
| 29 | IL12B | <LOD | 22.17 |
| 30 | IL13 | <LOD | 14.96 |
| 31 | IL16 | <LOD | 32.98 |
| 32 | IL2 | <LOD | 31.87 |
| 33 | IL3 | <LOD | 32.24 |
| 34 | IL7 | <LOD | 22.3 |
| 35 | TGFB1 | <LOD | 10.63 |
| 36 | TNF | <LOD | 31.72 |
| 37 | CCL15 | <LOD | >35 |
| 38 | CCL16 | <LOD | >35 |
| 39 | CXCL13 | <LOD | >35 |
| 40 | IFNG | <LOD | >35 |
| 41 | VEGF | <LOD | >35 |
| 42 | XCL1 | <LOD | >35 |

Example 11

Analysis of Proteome of Human ESC-derived MSCs (hESC-MSCs): Biological Processes that are Modulated by the Secreted Proteins To investigate if the secreted products have the potential to repair the injured tissues or organs, gene products are first classified according to their biological processes and pathways according to the Gene Ontology (GO). The frequency of unique genes in the secreted MSC proteome associated with each process or pathway is then compared to the gene-frequency for the respective pathway or process in a database collated from Unigene, Entrez and GenBank. Significantly higher frequencies of genes ($p<0.05$) are associated with 58 biological processes and 30 pathways.

Biological processes classified by GO modulated by the 201 unique gene products:

| GO Biological Processes | # genes (ref) | % (ref) | # genes (expt) | % (expt) | p-value |
|---|---|---|---|---|---|
| 1. GO:42221: response to chemical stimulus | 130 | 0.53 | 23 | 11.56 | 2.50E−24 |
| 2. GO:42330: taxis | 130 | 0.53 | 23 | 11.56 | 2.50E−24 |
| 3. GO:6935: chemotaxis | 130 | 0.53 | 23 | 11.56 | 2.50E−24 |
| 4. GO:9605: response to external stimulus | 157 | 0.65 | 24 | 12.06 | 9.45E−24 |
| 5. GO:50896: response to stimulus | 158 | 0.650 | 24 | 12.06 | 1.11E−23 |
| 6. GO:9628: response to abiotic stimulus | 150 | 0.62 | 23 | 11.56 | 7.83E−23 |
| 7. GO:48513: organ development | 116 | 0.48 | 11 | 5.53 | 3.06E−09 |
| 8. GO:7275: development | 827 | 3.40 | 23 | 11.56 | 3.27E−07 |
| 9. GO:16052: carbohydrate catabolism | 51 | 0.21 | 6 | 3.02 | 3.66E−06 |
| 10. GO:19320: hexose catabolism | 51 | 0.21 | 6 | 3.02 | 3.66E−06 |
| 11. GO:44248: cellular catabolism | 51 | 0.21 | 6 | 3.02 | 3.66E−06 |
| 12. GO:44265: cellular macromolecule catabolism | 51 | 0.21 | 6 | 3.02 | 3.66E−06 |
| 13. GO:44275: cellular carbohydrate catabolism | 51 | 0.21 | 6 | 3.02 | 3.66E−06 |
| 14. GO:46164: alcohol catabolism | 51 | 0.21 | 6 | 3.02 | 3.66E−06 |
| 15. GO:46365: monosaccharide catabolism | 51 | 0.21 | 6 | 3.02 | 3.66E−06 |
| 16. GO:6007: glucose catabolism | 51 | 0.21 | 6 | 3.02 | 3.66E−06 |
| 17. GO:6096: glycolysis | 51 | 0.21 | 6 | 3.02 | 3.66E−06 |
| 18. GO:9057: macromolecule catabolism | 51 | 0.21 | 6 | 3.02 | 3.66E−06 |
| 19. GO:9056: catabolism | 53 | 0.22 | 6 | 3.02 | 4.60E−06 |
| 20. GO:15980: energy derivation by oxidation of organic compounds | 65 | 0.27 | 6 | 3.02 | 1.53E−05 |
| 21. GO:19318: hexose metabolism | 65 | 0.27 | 6 | 3.02 | 1.53E−05 |
| 22. GO:44262: cellular carbohydrate metabolism | 65 | 0.27 | 6 | 3.02 | 1.53E−05 |
| 23. GO:5975: carbohydrate metabolism | 65 | 0.27 | 6 | 3.02 | 1.53E−05 |
| 24. GO:5996: monosaccharide metabolism | 65 | 0.27 | 6 | 3.02 | 1.53E−05 |
| 25. GO:6006: glucose metabolism | 65 | 0.27 | 6 | 3.02 | 1.53E−05 |
| 26. GO:6066: alcohol metabolism | 65 | 0.27 | 6 | 3.02 | 1.53E−05 |
| 27. GO:6091: generation of precursor metabolites and energ | 65 | 0.27 | 6 | 3.02 | 1.53E−05 |
| 28. GO:6092: main pathways of carbohydrate metabolism | 65 | 0.27 | 6 | 3.02 | 1.53E−05 |
| 29. GO:43170: macromolecule metabolism | 571 | 2.35 | 16 | 8.04 | 2.03E−05 |
| 30. GO:1525: angiogenesis | 44 | 0.18 | 5 | 2.51 | 2.90E−05 |
| 31. GO:1568: blood vessel development | 47 | 0.19 | 5 | 2.51 | 4.02E−05 |
| 32. GO:1944: vasculature development | 47 | 0.19 | 5 | 2.51 | 4.02E−05 |
| 33. GO:48514: blood vessel morphogenesis | 47 | 0.19 | 5 | 2.51 | 4.02E−05 |
| 34. GO:6950: response to stress | 10 | 0.04 | 3 | 1.51 | 6.18E−05 |
| 35. GO:9611: response to wounding | 10 | 0.04 | 3 | 1.51 | 6.18E−05 |
| 36. GO:1660: fever | 2 | 0.01 | 2 | 1.01 | 6.64E−05 |
| 37. GO:31649: heat generation | 2 | 0.01 | 2 | 1.01 | 6.64E−05 |
| 38. GO:43207: response to external biotic stimulus | 2 | 0.01 | 2 | 1.01 | 6.64E−05 |
| 39. GO:6952: defense response | 2 | 0.01 | 2 | 1.01 | 6.64E−05 |
| 40. GO:6954: inflammatory response | 2 | 0.01 | 2 | 1.01 | 6.64E−05 |
| 41. GO:6955: immune response | 2 | 0.01 | 2 | 1.01 | 6.64E−05 |
| 42. GO:9607: response to biotic stimulus | 2 | 0.01 | 2 | 1.01 | 6.64E−05 |
| 43. GO:9613: response to pest, pathogen or parasite | 2 | 0.01 | 2 | 1.01 | 6.64E−05 |
| 44. GO:9887: organ morphogenesis | 53 | 0.22 | 5 | 2.51 | 7.23E−05 |
| 45. GO:1659: thermoregulation | 3 | 0.01 | 2 | 1.01 | 1.98E−04 |
| 46. GO:30097: hemopoiesis | 26 | 0.11 | 3 | 1.51 | 1.22E−03 |
| 47. GO:48534: hemopoietic or lymphoid organ development | 26 | 0.11 | 3 | 1.51 | 1.22E−03 |
| 48. GO:1501: skeletal development | 38 | 0.16 | 3 | 1.51 | 3.67E−03 |
| 49. GO:1503: ossification | 38 | 0.16 | 3 | 1.51 | 3.67E−03 |
| 50. GO:31214: biomineral formation | 38 | 0.16 | 3 | 1.51 | 3.67E−03 |
| 51. GO:46849: bone remodeling | 38 | 0.16 | 3 | 1.51 | 3.67E−03 |
| 52. GO:6793: phosphorus metabolism | 13 | 0.05 | 2 | 1.01 | 4.88E−03 |
| 53. GO:6796: phosphate metabolism | 13 | 0.05 | 2 | 1.01 | 4.88E−03 |
| 54. GO:9888: tissue development | 54 | 0.22 | 3 | 1.51 | 9.82E−03 |
| 55. GO:45045: secretory pathway | 34 | 0.14 | 2 | 1.01 | 3.14E−02 |
| 56. GO:6887: exocytosis | 34 | 0.14 | 2 | 1.01 | 3.14E−02 |
| 57. GO:46903: secretion | 36 | 0.15 | 2 | 1.01 | 3.49E−02 |
| 58. GO:1570: vasculogenesis | 5 | 0.02 | 1 | 0.50 | 4.02E−02 |

| GO Pathways | p-value |
|---|---|
| 1. Cytokine-cytokine receptor interaction | 4.97E−47 |
| 2. ECM-receptor interaction | 3.21E−17 |
| 3. Jak-STAT signaling pathway | 1.19E−10 |

-continued

|  | | p-value |
|---|---|---|
| 4. | MAPK signaling pathway | 1.19E−08 |
| 5. | Toll-like receptor signaling pathway | 1.34E−05 |
| 6. | TGF-beta signaling pathway | 0.000292 |
| 7. | mTOR signaling pathway | 0.0143 |
| 8. | Fc epsilon RI signaling pathway | 0.00267 |
| 9. | Epithelial cell signaling in Helicobacter pylori infection | 0.0183 |
| 10. | Cell Communication | 1.17E−17 |
| 11. | Gap junction | 0.00077 |
| 12. | Tight junction | 0.0459 |
| 13. | Focal adhesion | 1.54E−21 |
| 14. | Regulation of actin cytoskeleton | 2.65E−13 |
| 15. | Leukocyte transendothelial migration | 3.88E−05 |
| 16. | Complement and coagulation cascades | 0.0488 |
| 17. | Antigen processing and presentation | 0.0102 |
| 18. | Apoptosis | 0.00648 |
| 19. | T cell receptor signaling pathway | 0.000866 |
| 20. | Hematopoietic cell lineage | 3.32E−14 |
| 21. | Type I diabetes mellitus | 4.60E−06 |
| 22. | Carbon fixation | 0.000257 |
| 23. | Glycolysis or Gluconeogenesis | 0.00106 |
| 24. | Stilbene, coumarine and lignin biosynthesis | 0.00348 |
| 25. | Phenylalanine metabolism | 0.00488 |
| 26. | Phenylalanine, tyrosine and tryptophan biosynthesis | 0.00567 |
| 27. | Methane metabolism | 0.00739 |
| 28. | Reductive carboxylate cycle (CO2 fixation) | 0.00739 |
| 29. | Inositol metabolism | 0.0163 |
| 30. | Citrate cycle (TCA cycle) | 0.0404 |

|  | GO Pathways | p-value |
|---|---|---|
| 1. | Cytokine-cytokine receptor interaction | 4.97E−47 |
| 2. | ECM-receptor interaction | 3.21E−17 |
| 3. | Jak-STAT signaling pathway | 1.19E−10 |
| 4. | MAPK signaling pathway | 1.19E−08 |
| 5. | Toll-like receptor signaling pathway | 1.34E−05 |
| 6. | TGF-beta signaling pathway | 0.000292 |
| 7. | mTOR signaling pathway | 0.0143 |
| 8. | Fc epsilon RI signaling pathway | 0.00267 |
| 9. | Epithelial cell signaling in Helicobacter pylori infection | 0.0183 |
| 10. | Cell Communication | 1.17E−17 |
| 11. | Gap junction | 0.00077 |
| 12. | Tight junction | 0.0459 |
| 13. | Focal adhesion | 1.54E−21 |
| 14. | Regulation of actin cytoskeleton | 2.65E−13 |
| 15. | Leukocyte transendothelial migration | 3.88E−05 |
| 16. | Complement and coagulation cascades | 0.0488 |
| 17. | Antigen processing and presentation | 0.0102 |
| 18. | Apoptosis | 0.00648 |
| 19. | T cell receptor signaling pathway | 0.000866 |
| 20. | Hematopoietic cell lineage | 3.32E−14 |
| 21. | Type I diabetes mellitus | 4.60E−06 |
| 22. | Carbon fixation | 0.000257 |
| 23. | Glycolysis or Gluconeogenesis | 0.00106 |
| 24. | Stilbene, coumarine and lignin biosynthesis | 0.00348 |
| 25. | Phenylalanine metabolism | 0.00488 |
| 26. | Phenylalanine, tyrosine and tryptophan biosynthesis | 0.00567 |
| 27. | Methane metabolism | 0.00739 |
| 28. | Reductive carboxylate cycle (CO2 fixation) | 0.00739 |
| 29. | Inositol metabolism | 0.0163 |
| 30. | Citrate cycle (TCA cycle) | 0.0404 |

Figure 8:
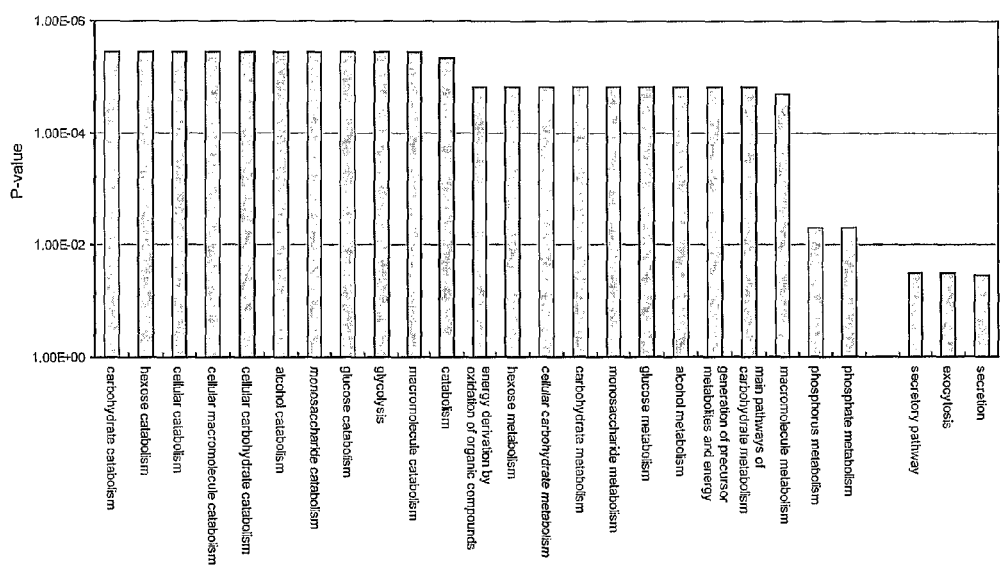
FIG. 8. Distribution of 201 gene products into biological processes. The 201 genes are classified into different biological processes in the GO classification system. 58 biological processes that are over-represented by the frequency of genes in the secretory proteome relative to the frequency of the genes in a database collated from Unigene, Entrez and GenBank with a p-value of <0.05 are grouped into three major groups: metabolism, defense response and tissue differentiation.
Figure 8:
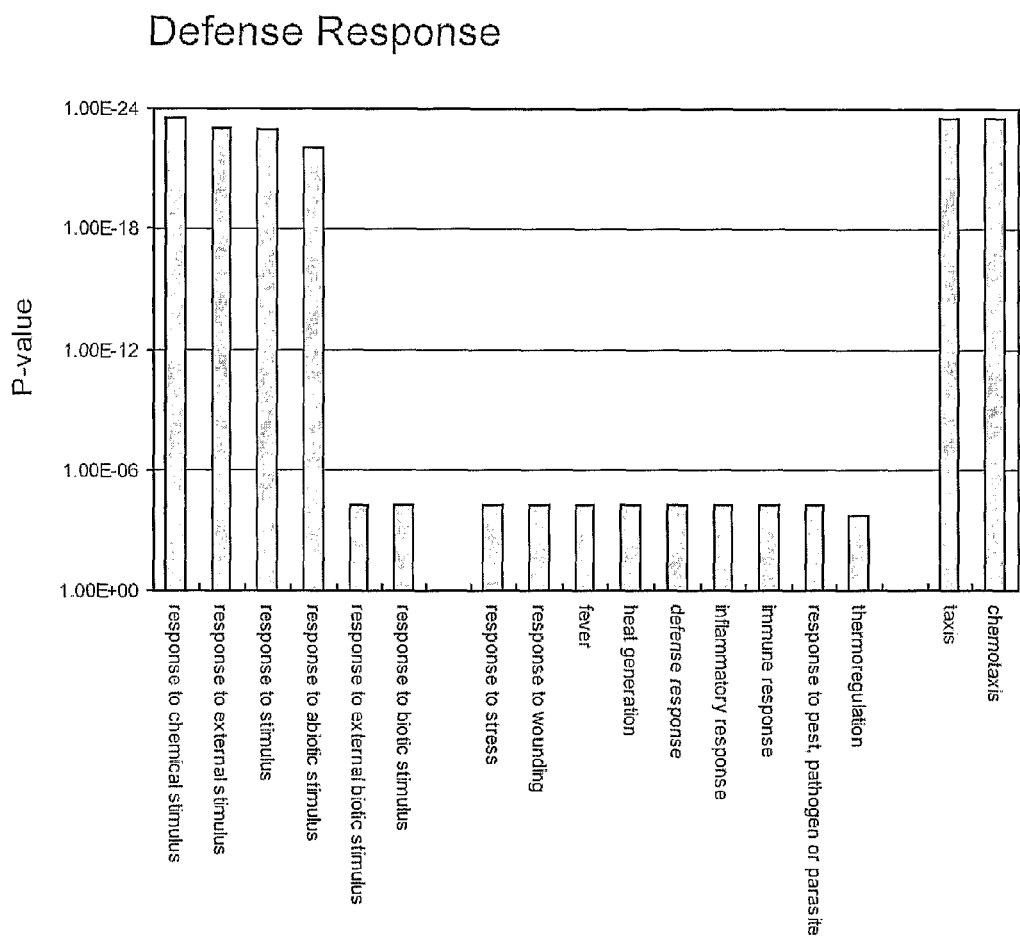
Figure 8:
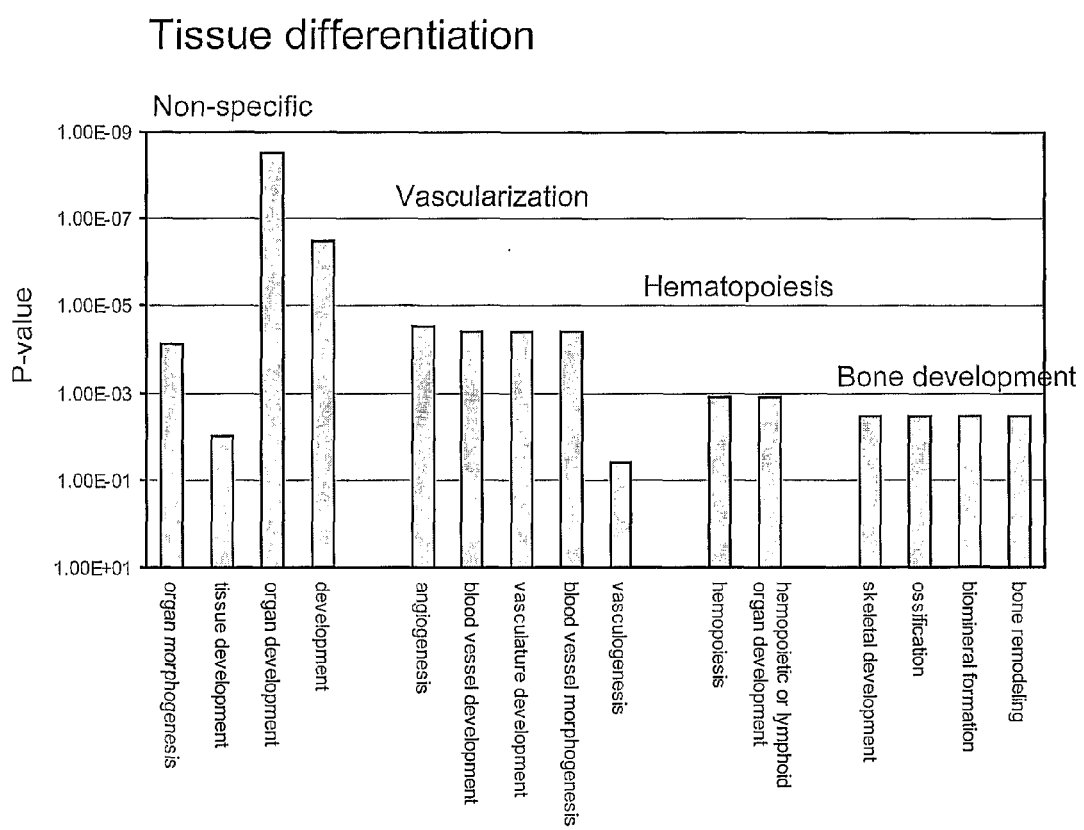
Figure 9:
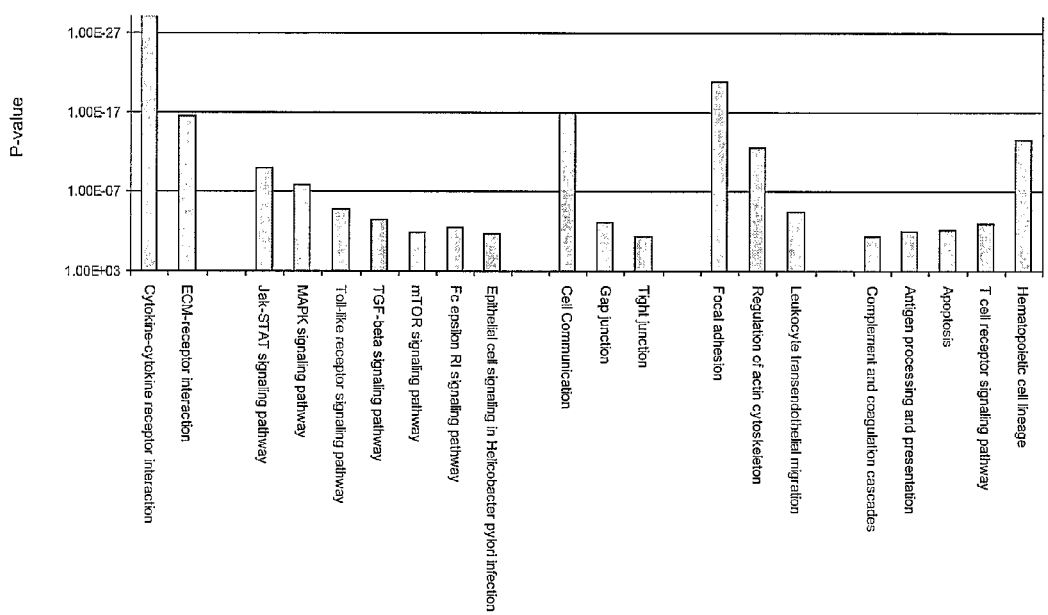
FIG. 9. Distribution of 201 gene products into pathways. The 201 genes are classified into different pathways in the GO classification system. 30 biological processes that are over-represented by the frequency of genes in the secretory proteome relative to the frequency of the genes in a database collated from Unigene, Entrez and GenBank with a p-value of <0.05 are categorised into several major categories: receptor binding, signal transduction, cell-cell interaction, cell migration, immune response and metabolism.
Figure 9:
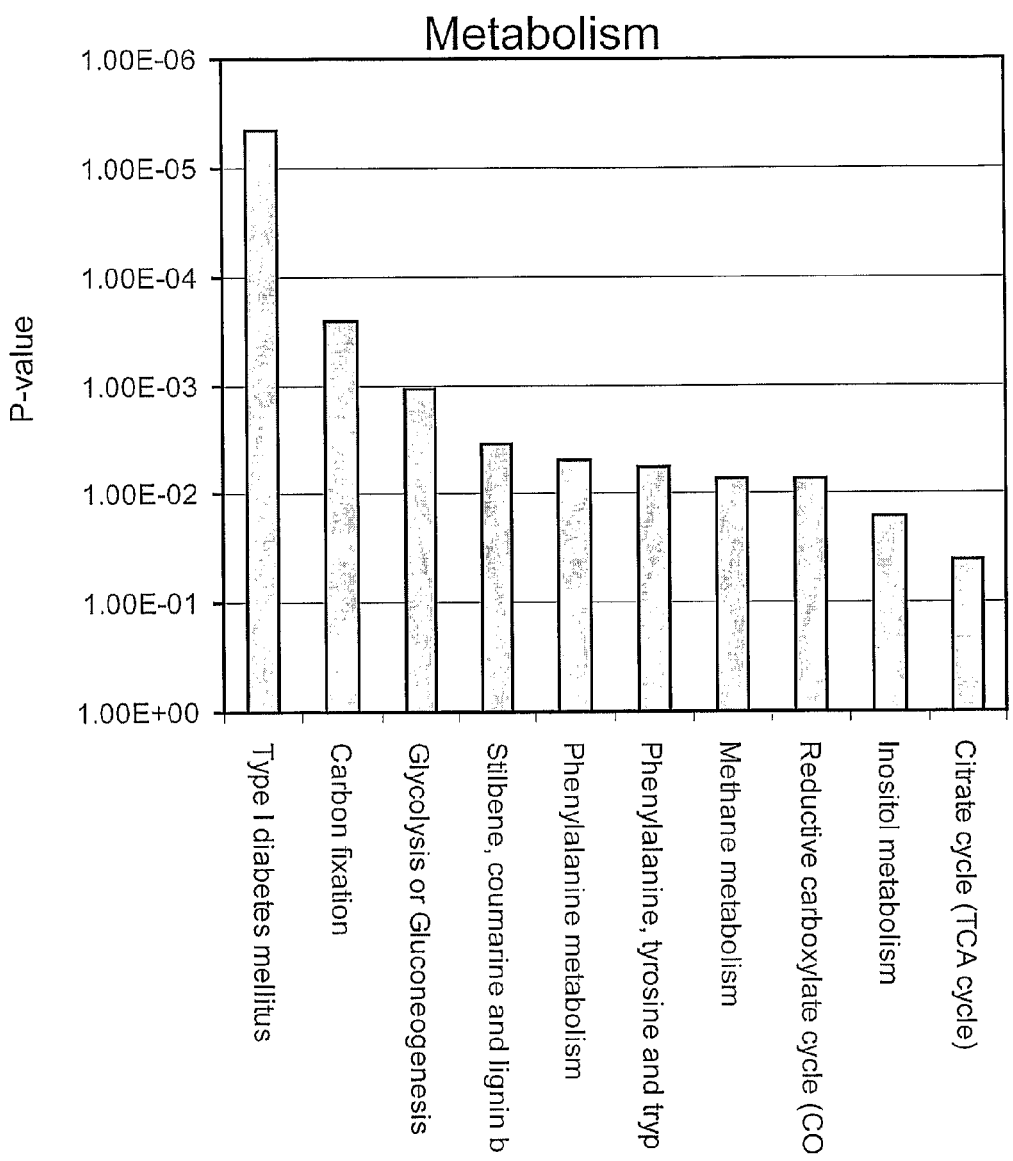

The 58 biological processes could be approximated into three major groups: metabolism, defense response and tissue differentiation while the 30 pathways could be broadly categorized into: receptor binding, signal transduction, cell-cell interaction, cell migration, immune response and metabolism (FIG. 8, FIG. 9). The postulated biological processes and pathways both suggest that the secreted proteins have a major impact on the cellular metabolism that will modulate energy production, breakdown, biosynthesis and secretion of macromolecules, processes essential for the removal of damaged tissues and regeneration of new tissues (FIG. 8, FIG. 9).

Consistent with the predominant presence of cytokines and chemokines in the MSC-conditioned media, the analysis also predicted that the secreted factors could elicit many cellular responses that are dependent on external stimuli e.g. chemotaxis, taxis and many immune responses (FIG. 8). Notably, the conditioned media could also induce biological processes that are important in tissue differentiation particularly processes that promote vascularization, hematopoiesis and bone development (FIG. 8). In those pathways predicted to be modulated by the secreted proteome, receptor-mediated binding of cytokine and ECM pathways are consistent with the predominance of cytokines and ECM components in the secreted proteome (FIG. 9). The main signal transduction pathways that could be activated by the secreted proteome include Jak-STAT signaling pathway, MAPK signaling pathway, Toll-like receptor signaling pathway, TGF-beta signaling pathway, mTOR signaling pathway, Fc epsilon RI signaling pathway and Epithelial cell signaling in *Helicobacter pylori* infection. The computational analysis of the secreted proteome also suggested that MSC secretion could enhance cell-cell interaction, migration and immune responses.

Example 12

Analysis of Proteome of Human ESC-derived MSCs (hESC-MSCs): Discussion

MSCs have been used in pre-clinical and clinical trials to treat a myriad of diseases (3-5,24-27). However the underlying mechanism has remained imprecisely understood. Although MSCs have to potential to differentiate into numerous cell type e.g. endothelial cells, cardiomyctes, chondrocytes that can potentially repair or regenerate damaged tissues, the therapeutic effects of MSCs cannot be solely mediated by generation of MSC-derived reparative cell types as differentiation of MSCs is generally too inefficient to mediate tissue repair or restore tissue function. It has been increasingly proposed that some of the therapeutic effects of MSCs may be mediated by paracrine factors secreted by MSCs (8). Here we describe the composition of the secreted proteome of hESC-MSCs through a combination of two techniques, LC-LC-MS and antibody arrays.

Although shot-gun proteomic analysis by LC-LC-MS is a sensitive technique and has high throughput capability, it is difficult to detect small proteins/peptides that include most of the cytokines, chemokines and growth factors. This is partially mitigated by the use of antibody arrays. The qualitative proteomic profile of the MSC secretion using the two techniques is highly reproducible. Proteins identified by LC MS/MS are present in two independently prepared batches of CM while those identified by antibody array are present in at least three of four independently prepared batches of CM. The resulting proteomic profile of secretion by hESC-MSCs included almost all the factors that are previously reportedly secreted by adult tissue-derived MSCs (13,16,19-21) as well as many others that have not been described. The robustness of the proteomic profiling is further substantiated by the detection of transcripts for 86-88% of gene products in the proteomic profile using a high throughput microarray-based gene expression analysis.

To evaluate and assess the potential functions of the MSC secretion on a global scale, we utilized the more readily available computational tools for gene expression analysis, based on gene products rather than on post-translationally modified proteins. Consistent with the predominance of cytokines and chemokines in the secretion, computational analysis predicted many processes and pathways that are generally associated with the functions of cytokines and chemokines such as chemotaxis, taxis, cellular response to external stimuli, breakdown, biosynthesis and secretion of macromolecules, cytokine-cytokine receptor interactions, cell-cell communication, and basal metabolism e.g. glucose and amino acid metabolism. The MSCs described here can be used to treat diseases which these functions may have a role in.

Although these processes and pathways are not specific to the process of injury, repair and regeneration in any particular cell or tissue type, their facilitation of immune cell migration to the site of injury, ECM remodelling and increase in the cellular metabolism will have reparative effects on most injured or diseased tissues.

Aside from these generic pathways associated with cytokines and chemokines, computational analysis also predicted that the secreted proteins regulate many processes involved in vascularization, hematopoiesis and skeletal development. Coincidentally, most reported MSC-mediated tissue repair or regeneration are associated with cardiovascular, hematopoietic and musculoskeletal tissues (3-5,24-27). Pathway analysis further uncovered candidate pathways that may be involved in mediating some of the paracrine effects of MSCs. In fact, many of these candidate pathways have already been implicated in many aspects of cardiovascular, hematopoietic and musculoskeletal biology. For example, Jak-STAT signaling is associated with cardioprotection (28), hematopoiesis (29,30), and skeletal repair and remodelling (31,32); MAPI signaling plays a crucial role in many aspects of cardiovascular responses (33,34), skeletal repair and remodelling (32, 35), and hematopoiesis (36); Toll-like receptor signalling has been implicated in the initiation and progression of cardiovascular pathologies (37), and modulation of innate and adaptive immunity (38); TGF-beta signalling is critical in correct heart development cardiac remodeling, progression to heart failure and vascularization (39-41) hematopoiesis (42), formation and remodelling of bone and cartilage (27,43) as well as general wound healing (44); and mTOR as an important regulator of cell growth and proliferation plays a non-specific yet critical role in both normal physiology and diseases (45-47).

In conclusion, our analysis of the secreted proteome in hESC-derived MSCs which includes many of the cytokines reportedly secreted by adult tissue-derived MSCs suggests that the secreted proteome could potentially exert modulating effects on tissue repair and regeneration particularly in the cardiovascular, hematopoietic and musculoskeletal tissues, and therefore provide molecular support for a MSC-mediated paracrine effect on tissue repair and regeneration in MSC transplantation studies. This secreted proteome also uncovered many highly testable hypotheses for the molecular mechanisms in MSC-mediated tissue repair and also potential "druggable" targets to modulate tissue repair and regeneration. The significant similarity between hESC-derived MSCs and adult tissue-derived MSCs suggest that conditioned media of either MSC cultures are likely to have similar biological activities.

Accordingly, this demonstrates that the MSCs derived by our methods have significant biological similarities to their bone marrow derived counterparts. These findings demonstrate the resemblance of the hESC-MSCs to adult BM-derived MSCs in their ability to secrete paracrine factors. Furthermore, any one or more proteins secreted from the MSCs described here, including in the form of conditioned media, may be used for the same purposes as the MSCs described herein.

hESC-derived MSCs, however, have several advantages over adult tissue-derived MSCs. The use of hESC cell lines as a tissue source of MSC constitutes an infinitely renewable and expansible tissue source, and enhances the reproducible and consistent batch to batch preparation of MSCs and therefore CM in a clinically compliant manner. It also boosts the scalability of preparing CM and the potential of developing low cost off-the-shelf therapeutics. In addition, the development of a serum-free chemically defined medium for the preparation of hESC-derived MSC CM reduces confounding and variable contaminants associated with complex media supplements such as serum or serum replacement media. Therefore, our elucidation of the CM is very relevant for the translation of MSC-based biologics towards clinical applications.

Example 13

Listing of 201 Genes in Each of the 58 Biological Processes

| Alcohol Metabolism | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

| Angiogenesis | |
|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |

Angiogenesis

| | |
|---|---|
| GI_42716312-S ANG | angiogenin, ribonuclease, RNase A family, 5 |
| GI_10337586-S FGF6 | fibroblast growth factor 6 |

Biomineral Formation

| | |
|---|---|
| GI_27262662-A CDH11 | cadherin 11, type 2, OB-cadherin (osteoblast) |
| GI_5902810-A BMP1 | bone morphogenetic protein 1 |
| GI_4507170-S SPARC | secreted protein, acidic, cysteine-rich (osteonectin) |

Blood Vessel Devolopment

| | |
|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Blood Vessel Morphogenesis

| | |
|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Bone Remodeling

| | |
|---|---|
| GI_27262662-A CDH11 | cadherin 11, type 2, OB-cadherin (osteoblast) |
| GI_5902810-A BMP1 BMP1 | bone morphogenetic protein 1 |
| GI_4507170-S SPARC | secreted protein, acidic, cysteine-rich (osteonectin) |

Carbohydrate Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Carbohydrate Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Carbohydrate Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Macromolecule Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Chemotaxis

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

Defense Response

| | |
|---|---|
| GI_27894305-S IL1B | interleukin 1, beta |
| GI_27894329-S IL1A | interleukin 1, alpha |

Development

| | |
|---|---|
| GI_42716312-S ANG | angiogenin, ribonuclease, RNase A family, 5 |
| GI_5902810-A BMP1 | bone morphogenetic protein 1 |
| GI_27262662-A CDH11 | cadherin 11, type 2, OB-cadherin (osteoblast) |
| GI_27262662-A CSF1 | colony stimulating factor 1 (macrophage) |
| GI_27437029-S CSF2 | colony stimulating factor 2 (granulocyte-macrophage) |
| GI_27437048-A CSF3 | colony stimulating factor 3 (granulocyte) |
| GI_34222286-S CYR61 | cysteine-rich, angiogenic inducer, 61 |
| GI_24430140-S FBN1 | fibrillin 1 (Marfan syndrome) |
| GI_4755135-S FBN2 | fibrillin 2 (congenital contractural arachnodactyly) |
| GI_10337586-S FGF6 | fibroblast growth factor 6 |
| GI_24430216-S IL10 | interleukin 10 |
| GI_28610153-S IL8 | interleukin 8 |
| GI_11321596-S KDR | kinase insert domain receptor (a type III receptor tyrosine kinase) |
| GI_4580419-A KITLG | KIT ligand |
| GI_6006018-S LIF | leukemia inhibitory factor (cholinergic differentiation factor) |
| GI_7262388-S PCOLCE | procollagen C-endopeptidase enhancer |
| GI_4507170-S SPARC | secreted protein, acidic, cysteine-rich (osteonectin) |
| GI_10863872-S TGFB1 | transforming growth factor, beta 1 (Camurati-Engelmann disease) |
| GI_4507470-S TGFBR3 | transforming growth factor, beta receptor III (betaglycan, 300 kDa) |
| GI_40317625-S THBS1 | thrombospondin 1 |
| GI_40805871-S THPO | thrombopoietin (myeloproliferative leukemia virus oncogene ligand, megakaryocyte growth and development factor) |
| GI_4507508-S TIMP1 | TIMP metallopeptidase inhibitor 1 |
| GI_30172563-S VEGF | vascular endothelial growth factor |

Energy Derivation by Oxidation of Organic Compounds

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Exocytosis

| | |
|---|---|
| GI_22538815-S CCL8 | chemokine (C-C motif) ligand 8 |
| GI_22538813-S CCL5 | chemokine (C-C motif) ligand 5 |

Fever

| | |
|---|---|
| GI_27894305-S IL1B | interleukin 1, beta |
| GI_27894329-S IL1A | interleukin 1, alpha |

Generation of Precursor Metabolites and Energy

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |

Generation of Precursor Metabolites and Energy -continued

| | |
|---|---|
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Glucose Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Glucose Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Glycolysis

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Heat Generation

| | |
|---|---|
| GI_27894305-S IL1B | interleukin 1, beta |
| GI_27894329-S IL1A | interleukin 1, alpha |

Hemopoiesis

| | |
|---|---|
| GI_27262662-A CSF1 | colony stimulating factor 1 (macrophage) |
| GI_4580419-A KITLG | KIT ligand |
| GI_24430216-S IL10 | interleukin 10 |

Hemopoietic or Lymphoid Organ Development

| | |
|---|---|
| GI_27262662-A CSF1 | colony stimulating factor 1 (macrophage) |
| GI_4580419-A KITLG | KIT ligand |
| GI_24430216-S IL10 | interleukin 10 |

Hexose Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |

Hexose Catabolism

| | |
|---|---|
| GI_21735620-S MDH2 | malate dehydrogenase 2, NAD (mitochondrial) |
| GI_26024330-S TPI1 | triosephosphate isomerase 1 |

Hexose Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Immune Response

| | |
|---|---|
| GI_27894305-S IL1B | interleukin 1, beta |
| GI_27894329-S IL1A | interleukin 1, alpha |

Inflammatory Response

| | |
|---|---|
| GI_27894305-S IL1B | interleukin 1, beta |
| GI_27894329-S IL1A | interleukin 1, alpha |

Macromolecule Metabolism

| | |
|---|---|
| GI_5902810-A BMP1 | bone morphogenetic protein 1 |
| GI_31542249-S C1R | complement component 1, r subcomponent |
| GI_22538429-A CTSB | cathepsin B |
| GI_16507965-S ENO1 | enolase 1, (alpha) |
| GI_16507966-S ENO2 | enolase 2 (gamma, neuronal) |
| GI_33859834-S HGF | hepatocyte growth factor (hepapoietin A; scatter factor) |
| GI_21735620-S MDH2 | malate dehydrogenase 2, NAD (mitochondrial) |
| GI_13027798-S MMP1 | matrix metallopeptidase 1 (interstitial collagenase) |
| GI_4505204-S MMP10 | matrix metallopeptidase 10 (stromelysin 2) |
| GI_13027796-S MMP13 | matrix metallopeptidase 13 (collagenase 3) |
| GI_13027803-S MMP3 | matrix metallopeptidase 3 (stromelysin 1, progelatinase) |
| GI_4826835-S MMP9 | matrix metallopeptidase 9 (gelatinase B, 92 kDa gelatinase, 92 kDa type IV collagenase) |
| GI_22095338-S PGK1 | phosphoglycerate kinase 1 |
| GI_31543396-S PGK2 | phosphoglycerate kinase 2 |
| GI_4505862-S PLAU | plasminogen activator, urokinase |
| GI_26024330-S TPI1 | triosephosphate isomerase 1 |

Macromolecule Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Main Pathways of Carbohydrate Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Monosaccharide Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Monosaccharide Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Organ Development

| | |
|---|---|
| GI_27262662-A CSF1 | colony stimulating factor 1 (macrophage) |
| GI_27262662-A CDH11 | cadherin 11, type 2, OB-cadherin (osteoblast) |
| GI_4580419-A KITLG | KIT ligand |
| GI_5902810-A BMP1 | bone morphogenetic protein 1 |
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_4507170-S SPARC | secreted protein, acidic, cysteine-rich (osteonectin) |
| GI_42716312-S ANG | angiogenin, ribonuclease, RNase A family, 5 |
| GI_24430216-S IL10 | interleukin 10 |
| GI_10337586-S FGF6 | fibroblast growth factor 6 |

Organ Morphogenesis

| | |
|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Ossification

| | |
|---|---|
| GI_27262662-A CDH11 | cadherin 11, type 2, OB-cadherin (osteoblast) |
| GI_5902810-A BMP1 | bone morphogenetic protein 1 |
| GI_4507170-S SPARC | secreted protein, acidic, cysteine-rich (osteonectin) |

| Phosphate Metabolism | |
| --- | --- |
| GI_22095338-S PGK1 | phosphoglycerate kinase 1 |
| GI_31543396-S PGK2 | phosphoglycerate kinase 2 |

| Phosphorus Metabolism | |
| --- | --- |
| GI_22095338-S PGK1 | phosphoglycerate kinase 1 |
| GI_31543396-S PGK2 | phosphoglycerate kinase 2 |

| Response to Abiotic Stimulus | |
| --- | --- |
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

| Response to Biotic Stimulus | |
| --- | --- |
| GI_27894305-S IL1B | interleukin 1, beta |
| GI_27894329-S IL1A | interleukin 1, alpha |

| Response to Chemical Stimulus | |
| --- | --- |
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |

-continued

| Response to Chemical Stimulus | |
| --- | --- |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

| Response to External Biotic Stimulus | |
| --- | --- |
| GI_27894305-S IL1B | interleukin 1, beta |
| GI_27894329-S IL1A | interleukin 1, alpha |

| Response to External Stimulus | |
| --- | --- |
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_27894305-S IL1B | interleukin 1, beta |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

| Response to Pest, Pathogen or Parasite | |
| --- | --- |
| GI_27894305-S IL1B | interleukin 1, beta |
| GI_27894329-S IL1A | interleukin 1, alpha |

| Response to Stimulus | |
| --- | --- |
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 |

Response to Stimulus

| | |
|---|---|
| | (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_27894305-S IL1B | interleukin 1, beta |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

Response to Stress

| | |
|---|---|
| GI_27894305-S IL1B | interleukin 1, beta |
| GI_4505862-S PLAU | plasminogen activator, urokinase |
| GI_27894329-S IL1A | interleukin 1, alpha |

Response to Wounding

| | |
|---|---|
| GI_27894305-S IL1B | interleukin 1, beta |
| GI_4505862-S PLAU | plasminogen activator, urokinase |
| GI_27894329-S IL1A | interleukin 1, alpha |

Secretion

| | |
|---|---|
| GI_22538815-S CCL8 | chemokine (C-C motif) ligand 8 |
| GI_22538813-S CCL5 | chemokine (C-C motif) ligand 5 |

Secretory Pathway

| | |
|---|---|
| GI_22538815-S CCL8 | chemokine (C-C motif) ligand 8 |
| GI_22538813-S CCL5 | chemokine (C-C motif) ligand 5 |

Skeletal Development

| | |
|---|---|
| GI_27262662-A CDH11 | cadherin 11, type 2, OB-cadherin (osteoblast) |
| GI_5902810-A BMP1 BMP1 | bone morphogenetic protein 1 |
| GI_4507170-S SPARC | secreted protein, acidic, cysteine-rich (osteonectin) |

Taxis

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |

Taxis

| | |
|---|---|
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

Thermoregulation

| | |
|---|---|
| GI_27894305-S IL1B | interleukin 1, beta |
| GI_27894329-S IL1A | interleukin 1, alpha |

Tissue Development

| | |
|---|---|
| GI_27262662-A CDH11 | cadherin 11, type 2, OB-cadherin (osteoblast) |
| GI_5902810-A BMP1 BMP1 | bone morphogenetic protein 1 |
| GI_4507170-S SPARC | secreted protein, acidic, cysteine-rich (osteonectin) |

Vasulogenesis

| | |
|---|---|
| GI_30172563-S VEGF | vascular endothelial growth factor |

Vasculature Development

| | |
|---|---|
| GI_11321596-S KDR | kinase insert domain receptor (a type II I receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Example 14

Listing of 201 Genes in Each of the 30 Pathways

| Antigen processing and presentation - *Homo sapiens* (human) | |
|---|---|
| GI_22538429-A CTSB | cathepsin B |
| GI_37704380-S B2M | beta-2-microglobulin |
| GI_24234685-A HSPA8 | heat shock 70 kDa protein 8 |
| GI_30581139-A PSME1 | proteasome (prosome, macropain) activator subunit 1 (PA28 alpha) |
| Apoptosis - *Homo sapiens* (human) | |
| GI_41281560-S CLSTN1 | calsyntenin 1 |
| GI_28416914-S IL3 | interleukin 3 (colony-stimulating factor, multiple) |
| GI_27894329-S IL1A | interleukin 1, alpha |
| GI_27894305-S IL1B | interleukin 1, beta |
| GI_25952110-S TNF | tumor necrosis factor (TNF superfamily, member 2) |
| Carbon fixation - *Homo sapiens* (human) | |
| GI_21735620-S MDH2 | malate dehydrogenase 2, NAD (mitochondrial) |
| GI_26024330-S TPI1 | triosephosphate isomerase 1 |
| GI_22095338-S PGK1 | phosphoglycerate kinase 1 |
| GI_31543396-S PGK2 | phosphoglycerate kinase 2 |
| Cell Communication - *Homo sapiens* (human) | |
| GI_27436944-A LMNA | lamin A/C |
| GI_5016088-S ACTB | actin, beta |
| GI_10938011-S ACTC | actin, alpha, cardiac muscle |
| GI_11038618-S ACTG1 | actin, gamma 1 |
| GI_14719826-S COL1A1 | collagen, type I, alpha 1 |
| GI_21536289-S COL1A2 | collagen, type I, alpha 2 |
| GI_15149480-S COL3A1 | collagen, type III, alpha 1 (Ehlers-Danlos syndrome type IV, autosomal dominant) |
| GI_45580690-S COL4A1 | collagen, type IV, alpha 1 |
| GI_17986276-S COL4A2 | collagen, type IV, alpha 2 |
| GI_16554578-S COL5A1 | collagen, type V, alpha 1 |
| GI_16554580-S COL5A2 | collagen, type V, alpha 2 |
| GI_15011912-S COL6A1 | collagen, type VI, alpha 1 |
| GI_17402876-A COL6A2 | collagen, type VI, alpha 2 |
| GI_17149810-A COL6A3 | collagen, type VI, alpha 3 |
| GI_18375521-A COL11A1 | collagen, type XI, alpha 1 |
| GI_16933543-A FN1 | fibronectin 1 |
| GI_9845497-S LAMC1 | laminin, gamma 1 (formerly LAMB2) |
| GI_16554581-S COL5A3 | collagen, type V, alpha 3 |
| GI_40317625-S THBS1 | thrombospondin 1 |
| Citrate cycle (TCA cycle) - *Homo sapiens* (human) | |
| GI_4504374-S CFH1/HF1 | complement factor H |
| GI_21735620-S MDH2 | malate dehydrogenase 2, NAD (mitochondrial) |
| Complement and coagulation cascades - *Homo sapiens* (human) | |
| GI_4505862-S PLAU | plasminogen activator, urokinase |
| GI_4504374-S CFH1/HF1 | complement factor H |
| GI_31542249-S C1R | complement component 1, r subcomponent |
| Cytokine-cytokine receptor interaction - *Homo sapiens* (human) | |
| GI_4506832-S CCL1 | chemokine (C-C motif) ligand 1 |
| GI_22538399-S CCL11 | chemokine (C-C motif) ligand 11 |
| GI_34335180-A CCL15 | chemokine (C-C motif) ligand 15 |
| GI_22538800-S CCL16 | chemokine (C-C motif) ligand 16 |
| GI_22538812-S CCL2 | chemokine (C-C motif) ligand 2 |
| GI_22538807-A CCL23 | chemokine (C-C motif) ligand 23 |
| GI_22165426-S CCL24 | chemokine (C-C motif) ligand 24 |
| GI_22547151-S CCL26 | chemokine (C-C motif) ligand 26 |
| GI_22538813-S CCL5 | chemokine (C-C motif) ligand 5 |
| GI_13435401-S CCL7 | chemokine (C-C motif) ligand 7 |
| GI_22538815-S CCL8 | chemokine (C-C motif) ligand 8 |
| GI_27262662-A CSF1 | colony stimulating factor 1 (macrophage) |
| GI_27437029-S CSF2 | colony stimulating factor 2 (granulocyte-macrophage) |
| GI_27437048-A CSF3 | colony stimulating factor 3 (granulocyte) |
| GI_4506856-S CX3CL1 | chemokine (C—X3—C motif) ligand 1 |
| GI_4504152-S CXCL1 | chemokine (C—X—C motif) ligand 1 (melanoma growth stimulating activity, alpha) |
| GI_14790145-S CXCL11 | chemokine (C—X—C motif) ligand 11 |
| GI_40316922-I CXCL12 | chemokine (C—X—C motif) ligand 12 (stromal cell-derived factor 1) |
| GI_5453576-S CXCL13 | chemokine (C—X—C motif) ligand 13 (B-cell chemoattractant) |
| GI_41872613-S CXCL5 | chemokine (C—X—C motif) ligand 5 |
| GI_4504098-S CXCR3 | chemokine (C—X—C motif) receptor 3 |
| GI_6031163-S EGF | epidermal growth factor (beta-urogastrone) |

| | | |
|---|---|---|
| GI_38455415-S FLT3LG | fms-related tyrosine kinase 3 ligand | |
| GI_33859834-S HGF | hepatocyte growth factor (hepapoietin A; scatter factor) | |
| GI_10835170-S IFNG | interferon, gamma | |
| GI_24430216-S IL10 | interleukin 10 | |
| GI_24497437-S IL12B | interleukin 12B (natural killer cell stimulatory factor 2, cytotoxic lymphocyte maturation factor 2, p40) | |
| GI_26787977-S IL13 | interleukin 13 | |
| GI_27894329-S IL1A | interleukin 1, alpha | |
| GI_27894305-S IL1B | interleukin 1, beta | |
| GI_28178860-S IL2 | interleukin 2 | |
| GI_28416914-S IL3 | interleukin 3 (colony-stimulating factor, multiple) | |
| GI_10834983-S IL6 | interleukin 6 (interferon, beta 2) | |
| GI_28610152-S IL7 | interleukin 7 | |
| GI_28610153-S IL8 | interleukin 8 | |
| GI_11321596-S KDR | kinase insert domain receptor (a type III receptor tyrosine kinase) | |
| GI_4580419-A KITLG | KIT ligand | |
| GI_4557714-S LEP | leptin (obesity homolog, mouse) | |
| GI_6006018-S LIF | leukemia inhibitory factor (cholinergic differentiation factor) | |
| GI_15451785-A PDGFB | platelet-derived growth factor beta polypeptide (simian sarcoma viral (v-sis) oncogene homolog) | |
| GI_15451788-S PDGFRB | platelet-derived growth factor receptor, beta polypeptide | |
| GI_10863872-S TGFB1 | transforming growth factor, beta 1 (Camurati-Engelmann disease) | |
| GI_4507462-S TGFB2 | transforming growth factor, beta 2 | |
| GI_40805871-S THPO | thrombopoietin (myeloproliferative leukemia virus oncogene ligand, megakaryocyte growth and development factor) | |
| GI_4507508-S TIMP1 | TIMP metallopeptidase inhibitor 1 | |
| GI_25952110-S TNF | tumor necrosis factor (TNF superfamily, member 2) | |
| GI_22547122-S TNFRSF11B | tumor necrosis factor receptor superfamily, member 11b (osteoprotegerin) | |
| GI_30172563-S VEGF | vascular endothelial growth factor | |
| GI_4506852-S XCL1 | chemokine (C motif) ligand 1 | |
| ECM-receptor interaction - *Homo sapiens* (human) | | |
| GI_9845497-S LAMC1 | laminin, gamma 1 (formerly LAMB2) | |
| GI_14719826-S COL1A1 | collagen, type I, alpha 1 | |
| GI_21536289-S COL1A2 | collagen, type I, alpha 2 | |
| GI_15149480-S COL3A1 | collagen, type III, alpha 1 (Ehlers-Danlos syndrome type IV, autosomal dominant) | |
| GI_45580690-S COL4A1 | collagen, type IV, alpha 1 | |
| GI_17986276-S COL4A2 | collagen, type IV, alpha 2 | |
| GI_16554578-S COL5A1 | collagen, type V, alpha 1 | |
| GI_16554580-S COL5A2 | collagen, type V, alpha 2 | |
| GI_15011912-S COL6A1 | collagen, type VI, alpha 1 | |
| GI_17402876-A COL6A2 | collagen, type VI, alpha 2 | |
| GI_17149810-A COL6A3 | collagen, type VI, alpha 3 | |
| GI_18375521-A COL11A1 | collagen, type XI, alpha 1 | |
| GI_16554581-S COL5A3 | collagen, type V, alpha 3 | |
| GI_16933543-A FN1 | fibronectin 1 | |
| GI_40317625-S THBS1 | thrombospondin 1 | |
| GI_7427516-S HSPG2 | heparan sulfate proteoglycan 2 (perlecan) | |
| GI_21361192-S CD44 | CD44 antigen (homing function and Indian blood group system) | |
| Epithelial cell signaling in *Helicobacter pylori* infection - *Homo sapiens* (human) | | |
| GI_22538813-S CCL5 | chemokine (C-C motif) ligand 5 | |
| GI_4504152-S CXCL1 | chemokine (C—X—C motif) ligand 1 (melanoma growth stimulating activity, alpha) | |
| GI_28610153-S IL8 | interleukin 8 | |
| Fc epsilon RI signaling pathway - *Homo sapiens* (human) | | |
| GI_25952110-S TNF | tumor necrosis factor (TNF superfamily, member 2) | |
| GI_26787977-S IL13 | interleukin 13 | |
| GI_27437029-S CSF2 | colony stimulating factor 2 (granulocyte-macrophage) | |
| GI_41281560-S CLSTN1 | calsyntenin 1 | |
| GI_28416914-S IL3 | interleukin 3 (colony-stimulating factor, multiple) | |
| Focal adhesion - *Homo sapiens* (human) | | |
| GI_5016088-S ACTB | actin, beta | |
| GI_100938011-S ACTC | actin, alpha, cardiac muscle | |
| GI_11038618-S ACTG1 | actin, gamma 1 | |
| GI_41281560-S CLSTN1 | calsyntenin 1 | |
| GI_18375521-A COL11A1 | collagen, type XI, alpha 1 | |
| GI_14719826-S COL1A1 | collagen, type I, alpha 1 | |
| GI_21536289-S COL1A2 | collagen, type I, alpha 2 | |
| GI_15149480-S COL3A1 | collagen, type III, alpha 1 (Ehlers-Danlos syndrome type IV, autosomal dominant) | |
| GI_45580690-S COL4A1 | collagen, type IV, alpha 1 | |
| GI_17986276-S COL4A2 | collagen, type IV, alpha 2 | |
| GI_16554578-S COL5A1 | collagen, type V, alpha 1 | |
| GI_16554580-S COL5A2 | collagen, type V, alpha 2 | |

| | |
|---|---|
| GI_16554581-S COL5A3 | collagen, type V, alpha 3 |
| GI_15011912-S COL6A1 | collagen, type VI, alpha 1 |
| GI_17402876-A COL6A2 | collagen, type VI, alpha 2 |
| GI_17149810-A COL6A3 | collagen, type VI, alpha 3 |
| GI_6031163-S EGF | epidermal growth factor (beta-urogastrone) |
| GI_4503744-S FLNA | filamin A, alpha (actin binding protein 280) |
| GI_16933543-A FN1 | fibronectin 1 |
| GI_33859834-S HGF | hepatocyte growth factor (hepapoietin A; scatter factor) |
| GI_19923111-S IGF1 | insulin-like growth factor 1 (somatomedin C) |
| GI_10834983-S IL6 | interleukin 6 (interferon, beta 2) |
| GI_11321596-S KDR | kinase insert domain receptor (a type III receptor tyrosine kinase) |
| GI_9845497-S LAMC1 | laminin, gamma 1 (formerly LAMB2) |
| GI_15451785-A PDGFB | platelet-derived growth factor beta polypeptide (simian sarcoma viral (v-sis) oncogene homolog) |
| GI_15451788-S PDGFRB | platelet-derived growth factor receptor, beta polypeptide |
| GI_40317625-S THBS1 | thrombospondin 1 |
| GI_30172563-S VEGF | vascular endothelial growth factor |

Gap junction - *Homo sapiens* (human)

| | |
|---|---|
| GI_5174476-S K-ALPHA-1 | tubulin, alpha, ubiquitous |
| GI_17986282-S TUBA3 | tubulin, alpha 3 |
| GI_31880337-S TUBA6 | tubulin, alpha 6 |
| GI_15451788-S PDGFRB | platelet-derived growth factor receptor, beta polypeptide |
| GI_6031163-S EGF | epidermal growth factor (beta-urogastrone) |
| GI_15451785-A PDGFB | platelet-derived growth factor beta polypeptide (simian sarcoma viral (v-sis) oncogene homolog) |

Glycolysis or Gluconeogenesis - *Homo sapiens* (human)

| | |
|---|---|
| GI_16507965-S ENO1 | enolase 1, (alpha) |
| GI_16507966-S ENO2 | enolase 2 (gamma, neuronal) |
| GI_26024330-S TPI1 | triosephosphate isomerase 1 |
| GI_22095338-S PGK1 | phosphoglycerate kinase 1 |
| GI_31543396-S PGK2 | phosphoglycerate kinase 2 |

Hematopoietic cell lineage - *Homo sapiens* (human)

| | |
|---|---|
| GI_21361192-S CD44 | CD44 antigen (homing function and Indian blood group system) |
| GI_4503744-S FLNA | filamin A, alpha (actin binding protein 280) |
| GI_40805871-S THPO | thrombopoietin (myeloproliferative leukemia virus oncogene ligand, megakaryocyte growth and development factor) |
| GI_4507508-S TIMP1 | TIMP metallopeptidase inhibitor 1 |
| GI_25952110-S TNF | tumor necrosis factor (TNF superfamily, member 2) |
| GI_27262662-A CSF1 | colony stimulating factor 1 (macrophage) |
| GI_27437048-A CSF3 | colony stimulating factor 3 (granulocyte) |
| GI_38455415-S FLT3LG | fms-related tyrosine kinase 3 ligand |
| GI_10834983-S IL6 | interleukin 6 (interferon, beta 2) |
| GI_27437029-S CSF2 | colony stimulating factor 2 (granulocyte-macrophage) |
| GI_27894329-S IL1A | interleukin 1, alpha |
| GI_27894305-S IL1B | interleukin 1, beta |
| GI_28416914-S IL3 | interleukin 3 (colony-stimulating factor, multiple) |
| GI_28610152-S IL7 | interleukin 7 |
| GI_4580419-A KITLG | KIT ligand |

Inositol metabolism - *Homo sapiens* (human)

| | |
|---|---|
| GI_26024330-S TPI1 | triosephosphate isomerase 1 |
| Insulin signaling pathway - *Homo sapiens* (human) | |

| | |
|---|---|
| GI_31377794-S CALM1 | calmodulin 1 (phosphorylase kinase, delta) |
| GI_41281560-S CLSTN1 | calsyntenin 1 |

Jak-STAT signaling pathway - *Homo sapiens* (human)

| | |
|---|---|
| GI_41281560-S CLSTN1 | calsyntenin 1 |
| GI_27437029-S CSF2 | colony stimulating factor 2 (granulocyte-macrophage) |
| GI_27437048-A CSF3 | colony stimulating factor 3 (granulocyte) |
| GI_10835170-S IFNG | interferon, gamma |
| GI_24430216-S IL10 | interleukin 10 |
| GI_24497437-S IL12B | interleukin 12B (natural killer cell stimulatory factor 2, cytotoxic lymphocyte maturation factor 2, p40) |
| GI_26787977-S IL13 | interleukin 13 |
| GI_28178860-S IL2 | interleukin 2 |
| GI_28416914-S IL3 | interleukin 3 (colony-stimulating factor, multiple) |
| GI_10834983-S IL6 | interleukin 6 (interferon, beta 2) |
| GI_28610152-S IL7 | interleukin 7 |
| GI_4557714-S LEP | leptin (obesity homolog, mouse) |
| GI_6006018-S LIF | leukemia inhibitory factor (cholinergic differentiation factor) |
| GI_40805871-S THPO | thrombopoietin (myeloproliferative leukemia virus oncogene ligand, megakaryocyte growth and development factor) |
| GI_4507508-S TIMP1 | TIMP metallopeptidase inhibitor 1 |

| Leukocyte transendothelial migration - *Homo sapiens* (human) | |
| --- | --- |
| GI_4826835-S MMP9 | matrix metallopeptidase 9 (gelatinase B, 92 kDa gelatinase, 92 kDa type IV collagenase) |
| GI_5453576-S CXCL13 | chemokine (C—X—C motif) ligand 13 (B-cell chemoattractant) |
| GI_28610153-S IL8 | interleukin 8 |
| GI_40316922-I CXCL12 | chemokine (C—X—C motif) ligand 12 (stromal cell-derived factor 1) |
| GI_41281560-S CLSTN1 | calsyntenin 1 |
| GI_5016088-S ACTB | actin, beta |
| GI_10938011-S ACTC | actin, alpha, cardiac muscle |
| GI_11038618-S ACTG1 | actin, gamma 1 |
| MAPK signaling pathway - *Homo sapiens* (human) | |
| GI_34106709-A BDNF | brain-derived neurotrophic factor |
| GI_6031163-S EGF | epidermal growth factor (beta-urogastrone) |
| GI_4503692-S FGF17 | fibroblast growth factor 17 |
| GI_4503700-S FGF4 | fibroblast growth factor 4 (heparin secretory transforming protein 1, Kaposi sarcoma oncogene) |
| GI_10337586-S FGF6 | fibroblast growth factor 6 |
| GI_15147344-S FGF7 | fibroblast growth factor 7 (keratinocyte growth factor) |
| GI_4503706-S FGF9 | fibroblast growth factor 9 (glia-activating factor) |
| GI_13186266-A FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| GI_4503744-S FLNA | filamin A, alpha (actin binding protein 280) |
| GI_40549401-A GDNF | glial cell derived neurotrophic factor |
| GI_24234685-A HSPA8 | heat shock 70 kDa protein 8 |
| GI_27894329-S IL1A | interleukin 1, alpha |
| GI_27894305-S IL1B | interleukin 1, beta |
| GI_15451785-A PDGFB | platelet-derived growth factor beta polypeptide (simian sarcoma viral (v-sis) oncogene homolog) |
| GI_15451788-S PDGFRB | platelet-derived growth factor receptor, beta polypeptide |
| GI_10863872-S TGFB1 | transforming growth factor, beta 1 (Camurati-Engelmann disease) |
| GI_4507462-S TGFB2 | transforming growth factor, beta 2 |
| GI_25952110-S TNF | tumor necrosis factor (TNF superfamily, member 2) |
| Methane metabolism - *Homo sapiens* (human) | |
| GI_40805871-S THPO | thrombopoietin (myeloproliferative leukemia virus oncogene ligand, megakaryocyte growth and development factor) |
| GI_32455261-A PRDX5 | peroxiredoxin 5 |
| mTOR signaling pathway - *Homo sapiens* (human) | |
| GI_30172563-S VEGF | vascular endothelial growth factor |
| GI_41281560-S CLSTN1 | calsyntenin 1 |
| GI_19923111-S IGF1 | insulin-like growth factor 1 (somatomedin C) |
| Phenylalanine, tyrosine and tryptophan biosynthesis - *Homo sapiens* (human) | |
| GI_16507965-S ENO1 | enolase 1, (alpha) |
| GI_16507966-S ENO2 | enolase 2 (gamma, neuronal) |
| Phenylalanine metabolism - *Homo sapiens* (human) | |
| GI_4505184-S MIF | macrophage migration inhibitory factor (glycosylation-inhibiting factor) |
| GI_40805871-S THPO | thrombopoietin (myeloproliferative leukemia virus oncogene ligand, megakaryocyte growth and development factor) |
| GI_32455261-A PRDX5 | peroxiredoxin 5 |
| Regulation of actin cytoskeleton - *Homo sapiens* (human) | |
| GI_5016088-S ACTB | actin, beta |
| GI_10938011-S ACTC | actin, alpha, cardiac muscle |
| GI_11038618-S ACTG1 | actin, gamma 1 |
| GI_5031634-S CFL1 | cofilin 1 (non-muscle) |
| GI_41281560-S CLSTN1 | calsyntenin 1 |
| GI_6031163-S EGF | epidermal growth factor (beta-urogastrone) |
| GI_4503692-S FGF17 | fibroblast growth factor 17 |
| GI_4503700-S FGF4 | fibroblast growth factor 4 (heparin secretory transforming protein 1, Kaposi sarcoma oncogene) |
| GI_10337586-S FGF6 | fibroblast growth factor 6 |
| GI_15147344-S FGF7 | fibroblast growth factor 7 (keratinocyte growth factor) |
| GI_4503706-S FGF9 | fibroblast growth factor 9 (glia-activating factor) |
| GI_13186266-A FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| GI_16933543-A FN1 | fibronectin 1 |
| GI_38044287-A GSN | gelsolin (amyloidosis, Finnish type) |
| GI_22507396-S MYH9 | myosin, heavy polypeptide 9, non-muscle |
| GI_15451785-A PDGFB | platelet-derived growth factor beta polypeptide (simian sarcoma viral (v-sis) oncogene homolog) |
| GI_15451788-S PDGFRB | platelet-derived growth factor receptor, beta polypeptide |
| GI_16753213-S PFN1 | profilin 1 |

| | |
|---|---|
| GI_34328943-S TMSB4X | thymosin, beta 4, X-linked |
| GI_34013529-S TMSL3 | thymosin-like 3 |

Stilbene, coumarine and lignin biosynthesis - *Homo sapiens* (human)

| | |
|---|---|
| GI_40805871-S THPO | thrombopoietin (myeloproliferative leukemia virus oncogene ligand, megakaryocyte growth and development factor) |
| GI_32455261-A PRDX5 | peroxiredoxin 5 |

T cell receptor signaling pathway - *Homo sapiens* (human)

| | |
|---|---|
| GI_25952110-S TNF | tumor necrosis factor (TNF superfamily, member 2) |
| GI_27437029-S CSF2 | colony stimulating factor 2 (granulocyte-macrophage) |
| GI_10835170-S IFNG | interferon, gamma |
| GI_24430216-S IL10 | interleukin 10 |
| GI_28178860-S IL2 | interleukin 2 |
| GI_41281560-S CLSTN1 | calsyntenin 1 |

TGF-beta signaling pathway - *Homo sapiens* (human)

| | |
|---|---|
| GI_4557730-S LTBP1 | latent transforming growth factor beta binding protein 1 |
| GI_40317625-S THBS1 | thrombospondin 1 |
| GI_10863872-S TGFB1 | transforming growth factor, beta 1 (Camurati-Engelmann disease) |
| GI_4507462-S TGFB2 | transforming growth factor, beta 2 |
| GI_25952110-S TNF | tumor necrosis factor (TNF superfamily, member 2) |
| GI_10835170-S IFNG | interferon, gamma |

Tight junction - *Homo sapiens* (human)

| | |
|---|---|
| GI_5016088-S ACTB | actin, beta |
| GI_10938011-S ACTC | actin, alpha, cardiac muscle |
| GI_11038618-S ACTG1 | actin, gamma 1 |
| GI_22507396-S MYH9 | myosin, heavy polypeptide 9, non-muscle |

Toll-like receptor signaling pathway - *Homo sapiens* (human)

| | |
|---|---|
| GI_14790145-S CXCL11 | chemokine (C—X—C motif) ligand 11 |
| GI_28610153-S IL8 | interleukin 8 |
| GI_24497437-S IL12B | interleukin 12B (natural killer cell stimulatory factor 2, cytotoxic lymphocyte maturation factor 2, p40) |
| GI_27894305-S IL1B | interleukin 1, beta |
| GI_41281560-S CLSTN1 | calsyntenin 1 |
| GI_10834983-S IL6 | interleukin 6 (interferon, beta 2) |
| GI_22538813-S CCL5 | chemokine (C-C motif) ligand 5 |
| GI_25952110-S TNF | tumor necrosis factor (TNF superfamily, member 2) |

Type I diabetes mellitus - *Homo sapiens* (human)

| | |
|---|---|
| GI_24497437-S IL12B | interleukin 12B (natural killer cell stimulatory factor 2, cytotoxic lymphocyte maturation factor 2, p40) |
| GI_28178860-S IL2 | interleukin 2 |
| GI_10835170-S IFNG | interferon, gamma |
| GI_27894329-S IL1A | interleukin 1, alpha |
| GI_27894305-S IL1B | interleukin 1, beta |
| GI_25952110-S TNF | tumor necrosis factor (TNF superfamily, member 2) |

Example 15

References for Examples 7 to 14

1. Le Blanc, K., and Pittenger, M. (2005) Cytotherapy 7, 36-45
2. Reiser, J., Zhang, X. Y., Hemenway, C. S., Mondal, D., Pradhan, L., and La Russa, V. F. (2005) Expert Opin Biol Ther 5, 1571-1584
3. Hui, J. H., Ouyang, H. W., Hutmacher, D. W., Goh, J. C., and Lee, E. H. (2005) Ann Acad Med Singapore 34, 206-212
4. Caplan, A. I. (2005) Tissue Eng 11, 1198-1211
5. Menasche, P. (2005) Curr Opin Mol Ther 7, 293-299
6. Laflamme, M. A., and Murry, C. E. (2005) Nat Biotechnol 23, 845-856
7. Kilinaird, T., Stabile, E., Burnett, M. S., Shou, M., Lee, C. W., Barr, S., Fuchs, S., and Epstein, S. E. (2004) Circulation 109, 1543-1549
8. Caplan, A. I., and Dennis, J. E. (2006) J Cell Biochem
9. Leedham, S. J., Brittan, M., McDonald, S. A., and Wright, N. A. (2005) J Cell Mol Med 9, 11-24
10. Togel, F., Hu, Z., Weiss, K., Isaac, J., Lange, C., and Westenfelder, C. (2005) Am J Physiol Renal Physiol 289, F31-42
11. Patschan, D., Plotkin, M., and Goligorsky, M. S. (2006) Curr Opin Pharmacol 6, 176-183
12. Miyahara, Y., Nagaya, N., Kataoka, M., Yanagawa, B., Tanaka, K., Hao, H., Ishino, K., Ishida, H., Shimizu, T., Kangawa, K., Sano, S., Okano, T., Kitamura, S., and Mori, H. (2006) Nat Med 12, 459-465
13. Gnecchi, M., He, H., Noiseux, N., Liang, O. D., Zhang, L., Morello, F., Mu, H., Melo, L. G., Pratt, R. E., Ingwall, J. S., and Dzau, V. J. (2006) Faseb J 20, 661-669
14. Gnecchi, M., He, H., Liang, O. D., Melo, L. G., Morello, F., Mu, H., Noiseux, N., Zhang, L., Pratt, R. E., Ingwall, J. S., and Dzau, V. J. (2005) Nat Med 11, 367-368
15. Mayer, H., Bertran, H., Lindennaier, W., Korff, T., Weber, H., and Weich, H. (2005) J Cell Biochemn 95, 827-839
16. Nakagami, H., Maeda, K., Morishita, R., Iguchi, S., Nishikawa, T., Takami, Y., Kikuchi, Y., Saito, Y., Tamai, K., Ogihara, T., and Kaneda, Y. (2005) Arterioscler Thromb Vasc Biol 25, 2542-2547
17. Van Overstraeten-Schlogel, N., Beguin, Y., and Gothot, A. (2006) Eur J Haematol 76, 488-493

18. Cheng, L., Qasba, P., Vanguri, P., and Thiede, M. A. (2000) J Cell Physiol 184, 58-69
19. Liu, C. H., and Hwang, S. M. (2005) Cytokine 32, 270-279
20. Haynesworth, S. E., Baber, M. A., and Caplan, A. I. (1996) J Cell Physiol 166, 585-592
21. Kinnaird, T., Stabile, E., Burnett, M. S., and Epstein, S. E. (2004) Circ Res 95, 354-363
22. Barreau, C., Paillard, L., and Osborne, H. B. (2005) Nucleic Acids Res 33, 7138-7150
23. Espel, E. (2005) Semin Cell Dev Biol 16, 59-67
24. Bhatia, R., and Hare, J. M. (2005) Congest Heart Fail 11, 87-91; quiz 92-83
25. Mauney, J. R., Volloch, V., and Kaplan, D. L. (2005) Tissue Eng 11, 787-802
26. Zimnet, J. M., and Hare, J. M. (2005) Basic Res Cardiol 100, 471-481
27. Lin, Z., Willers, C., Xu, J., and Zheng, M. H. (2006) Tissue Eng
28. Negoro, S., Kunisada, K., Tone, E., Funamoto, M., Oh, H., Kishimoto, T., and Yamaucihi-Takihara, K. (2000) Cardiovasc Res 47, 797-805
29. Ward, A. C., Touw, I., and Yoshimura, A. (2000) Blood 95, 19-29
30. Ungureaniu, D., and Silveimoinen, O. (2005) Sci STIKE 2005, pe49
31. Blair, H. C., Robinson, L. J., and Zaidi, M. (2005) Biochem Biophys Res Commun 328, 728-738
32. Malemnud, C. J. (2004) Clin Orthop Relat Res, S145-151
33. Nigro, J., Osman, N., Dart, A. M., and Little, P. J. (2006) Endocr Rev 27, 242-259
34. Pandya, N., Santani, D., and Jain, S. (2005) Cardiovasc Drug Rev 23, 247-254
35. Berenbawn, F. (2004) Curr Opin Rheumatol 16, 616-622
36. Platanias, L. C. (2003) Blood 101, 4667-4679
37. de Kleijn, D., and Pasterlkamp, G. (2003) Cardiovasc Res 60, 58-67
38. Ozato, K., Tsujirnura, H., and Tamura, T. (2002) Biotechniques Suppl, 66-68, 70, 72 passim
39. Euler-Taimor, G., and Heger, J. (2006) Cardiovascular Research 69, 15-25
40. Bertolino, P., Deckers, M., Lebrin, F., and ten Dijke, P. (2005) Chest 128, 585S-590S
41. Bobik, A. (2006) Arterioscler Thromb Vasc Biol
42. Ruscetti, F. W., Akel, S., and Bartelrnez, S. H. (2005) Oncogene 24, 5751-5763
43. Janssens, K., ten Dijke, P., Janssens, S., and Van Hul, W. (2005) Endocr Rev 26, 743-774
44. Faler, B. J., Macsata, R. A., Plummer, D., Mishra, L., and Sidawy, A. N. (2006) Perspect Vasc Surg Endovasc Ther 18, 55-62
45. Wullschleger, S., Loewith, R., and Hall, M. N. (2006) Cell 124, 471-484
46. Proud, C. G. (2004) Cardiovasc Res 63, 403-413
47. Tee, A. R., and Blenis, J. (2005) Semin Cell Dev Biol 16, 29-37

GENERAL REFERENCES

1. Le Blanc, K. & Pittenger, M. Mesenchymal stem cells: progress toward promise. Cytotherapy 7, 36-45 (2005).
2. Xu, C. et al. Immortalized fibroblast-like cells derived from human embryonic stem cells support undifferentiated cell growth. Stem Cells 22, 972-80 (2004).
3. Barberi, T., Willis, L. M., Socci, N. D. & Studer, L. Derivation of multipotent mesenchymal precursors from human embryonic stem cells. PLoS Med 2, e161 (2005).
4. van den Bos, C. et al. Human mesenchymal stem cells respond to fibroblast growth factors. Hum Cell 10, 45-50 (1997).
5. Kilian, O. et al. Effects of platelet growth factors on human mesenchymal stem cells and human endothelial cells in vitro. Eur J Med Res 9, 337-44 (2004).
6. Cowan, C. A. et al. Derivation of embryonic stem-cell lines from human blastocysts. N Engl J Med 350, 1353-6 (2004).
7. Thomson, J. A. et al. Embryonic Stem Cell Lines Derived from Human Blastocysts. Science 282, 1145-1147 (1998).
8. Que, J. et al. Generation of hybrid cell lines with endothelial potential from spontaneous fusion of adult bone marrow cells with embryonic fibroblast feeder. In Vitro Cell Dev Biol Anim 40, 143-9 (2004).
9. Javazon, E. H., Beggs, K. J. & Flake, A. W. Mesenchymal stem cells: paradoxes of passaging. Exp Hematol 32, 414-25 (2004).
10. Barry, F. P. & Murphy, J. M. Mesenchymal stem cells: clinical applications and biological characterization. Int J Biochem Cell Biol 36, 568-84 (2004).
11. Majumdar, M. K. et al. Characterization and functionality of cell surface molecules on human mesenchymal stem cells. J Biomed Sci 10, 228-41 (2003).
12. Rosen, E. D. The transcriptional basis of adipocyte development. Prostaglandins Leukot Essent Fatty Acids 73, 31-4 (2005).
13. Okazaki, K. & Sandell, L. J. Extracellular matrix gene regulation. Clin Orthop RelatRes, S123-8 (2004).
14. Barreau, C., Paillard, L. & Osborne, H. B. AU-rich elements and associated factors: are there unifying principles? Nucleic Acids Res 33, 7138-50 (2005).
15. Espel, E. The role of the AU-rich elements of mRNAs in controlling translation. Semin Cell Dev Biol 16, 59-67 (2005). 21
16. Gerstenfeld, L. C. & Shapiro, F. D. Expression of bone-specific genes by hypertrophic chondrocytes: implication of the complex functions of the hypertrophic chondrocyte during endochondral bone development. J Cell Biochem 62, 1-9 (1996).
17. Knott, L. & Bailey, A. J. Collagen cross-linlks in mineralizing tissues: a review of their chemistry, function, and clinical relevance. Bone 22, 181-7 (1998).
18. Su, B. & Karin, M. Mitogen-activated protein kinase cascades and regulation of gene expression. Curr Opin Immunol 8, 402-11 (1996).
19. Torres, M. & Forman, H. J. Redox signaling and the MAP kinase pathways. Biofactors 17, 287-96 (2003).
20. Matsukawa, J., Matsuzawa, A., Takeda, K. & Ichijo, H. The ASK1-MAP kinase cascades in mammalian stress response. J Biochem (Tokyo) 136, 261-5 (2004).
21. Sekine, Y., Talceda, K. & Ichijo, H. The ASK1-MAP Kinase Signaling in ER Stress and Neurodege-nerative Diseases. Curr Mol Med 6, 87-97 (2006).
22. Cai, J. et al. Assessing self-renewal and differentiation in hESC lines. Stem Cells (2005).
23. Reubinoff, B. E., Pera, M. F., Fong, C. Y., Trounson, A. & Bongso, A. Embryonic stem cell lines from human blastocysts: somatic differentiation in vitro. Nat Biotechnol 18, 399-404 (2000).
24. Lim, S. C. & Oh, S. H. The role of CD24 in various human epithelial neoplasias. Pathol Res Pract 201, 479-86 (2005).
25. Bhatia, R. & Hare, J. M. Meselnchymal stem cells: future source for reparative medicine. Congest Heart Fail 11, 87-91; quiz 92-3 (2005).
26. Pittenger, M. F. et al. Multilineage potential of adult human mesenchymal stem cells. Science 284, 143-147 (1999).

27. Damjanov, I., Damjanov, A. & Solter, D. Production of teratocarcinomas from embryos transplanted to extra-uterine sites. in Teratocarcinomas and embryonic stem cells: a practical approach. (ed. Robertson, E. J.) 1-17 (IRL Press Limited, Oxford, 1987).

28. Yin, Y. et al. AFP(+), ESC-Derived Cells Engraft and Differentiate into Hepatocytes in Vivo. Stem Cells 20, 338-346 (2002).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

What is claimed is:

1. A method of establishing, from an embryonic stem (ES) cell, a mesenchymal progenitor cell line comprising mesenchymal stem cells (MSCs), the method comprising:
    (a) propagating an ES cell in the absence of co-culture with a feeder cell layer, in a serum free medium comprising FGF2,
    (b) selecting mesenchymal stem cells from the propagated cells based on expression of one or more cell surface markers, and
    (c) growing the mesenchymal stem cells selected in step (b) in medium comprising serum;
    thereby establishing a mesenchymal progenitor cell line comprising MSCs, wherein the mesenchymal progenitor cell line maintains self-renewal without transformation, and wherein the mesenchymal progenitor cell line is lineage restricted compared to the ES cell.

2. A method according to claim 1, in which the embryonic stem cell is a human embryonic stem cell.

3. A method according to claim 1, in which the embryonic stem cell is obtained by dispersing an ES cell colony with trypsin.

4. A method according to claim 1, in which the ES cell is obtained by splitting a ES cell culture.

5. A method according to claim 1, in which the ES cell is propagated on a culture substrate.

6. A method according to claim 5, in which the culture substrate comprises a gelatinized plate.

7. A method according to claim 1, in which the serum free medium comprises FGF2 at a concentration of about 5 ng/ml.

8. A method according to claim 7, in which the serum free medium further comprises PDGF AB at a concentration of about 5 ng/ml.

9. A method according to claim 1, in which the serum free medium is supplemented with serum replacement media.

10. A method according to claim 1, in which the propagated cells are split 1:4 when confluent by trypsinising.

11. A method according to claim 1, in which the mesenchymal stem cell is obtained by selecting a cell with an elevated expression of one or more surface markers selected from the group consisting of: ANPEP (CD13;LAP1;PEPN; gp150: NM_001150.1); ENG (END;ORW;HHT1;ORW1; CD105: NM_000118.1); SCN9A (PN1;NE-NA: NM_002977.1); TRPV2 (VRL;VRL1;VRL-1;MGC12549: NM_016113.3); RAMP1 (:NM_005855.1); F2RL2 (PAR3: NM_004101.2); NTSR1 (NTR: NM_002531.1); GABRA2 (:NM_000807.1); SLC16A4 (MCT4: NM_004696.1); ITGA4 (CD49D: NM_000885.2); NCAM2 (NCAM21; MGC51008: NM_004540.2); IL1R1 (P80;IL1R;IL1RA; CD121A;D2S1473;IL-1R-alpha: NM_000877.2); PDGFRA (CD140A;PDGFR2: NM_006206.2); VCAM1 (INCAM-100: NM_080682.1); SSFA2 (CS1;CS-1;KRAP; SPAG13;KIAA1927: NM_006751.3); TRHDE (PAP-II: NM_013381.1); EDG2 (LPA1;edg-2;vzg-1;Gper26; Mrec1.3;rec.1.3: NM_001401.3); NTSE (eN;NT5;NTE; eNT;CD73;E5NT: NM_002526.1); FLRT2 (KIAA0405: NM_013231.2); and FAP (FAPA;DPPIV;SEPRASE: NM_004460.2).

12. A method according to claim 1, in which the surface marker comprises CD105 (Accession Number NM_000118.1).

13. A method according to claim 1, in which the surface marker comprises CD73 (Accession Number NM_002526.1).

14. A method according to claim 1, in which the mesenchymal stem cell is obtained by selecting a cell with a reduced expression of one or more surface markers selected from the group consisting of: ITGB1BP3 (MIBP: NM_014446.1); PTPRZ1 (PTPZ;HPTPZ;PTP18;PTPRZ;RPTPB: NM_002851.1); CNTN1 (F3;GP135: NM_175038.1); PCDH1 (PC42;PCDH42;MGC45991: NM_002587.3); PODXL (PCLP;Gp200: NM_005397.2); GPR64 (HE6; TM7LN2: NM_005756.1); PROM1 (AC133;CD133; PROML1: NM_006017.1); GPRC5C (RAIG3;RAIG-3: NM_022036.2); CD24 (CD24A: NM_013230.1); CLDN3 (RVP1;HRVP1;CPE-R2;CPETR2: NM_001306.2); TACSTD1 (EGP;KSA;M4S1;MK-1;EGP40;MIC18;TROP1;EpCAM;hEGP-2;CO17-1A;GA733-2: NM_002354.1); HTR3A (HTR3: NM_000869.1); FGFR4 (TIU;JTK2: NM_022963.1); ADCY1 (:NM_021116.1); FGFR3 (ACH; CEK2;JTK4;HSFGFR3EX: NM_022965.1); IL17RB (CRL4;EV127;IL17BR;IL17RH1;MGC5245: NM_018725.2); SORL1 (LR11;LRP9;SORLA;gp250; SorLA-1: NM_003105.3); GPM6B (M6B: NM_005278.2); KCNS3 KV9.3;MGC9481: NM_002252.3); and FZD3 (Fz-3;hFz3: NM_017412.2).

15. A method according to claim 1, in which the surface marker comprises CD24 (Accession Number NM_013230.1).

16. A method according to claim 1, in which the mesenchymal stem cell is obtained by selecting for cells which are CD105+ CD24−.

17. A method according to claim 1, in which the mesenchymal stem cell is selected by labelling the cell with an antibody against the surface antigen.

18. A method according to claim 1, in which the mesenchymal stem cell is selected by fluorescence activated cell sorting (FACS).

19. A method according to claim 1, in which the cell is passaged for fewer than 35 generations.

20. A method according to claim 1, in which the cell is propagated for about 7 to about 14 days.

21. A method according to claim 1, in which the ES cell is from a huES9 colony.

22. A method according to claim 1, in which the ES cell is from a H1 ESC colony.

23. A method according to claim 1, in which the MSCs display a surface antigen profile which is at least one of CD29+, CD44+, CD49a and e+, CD105+, CD166+ and CD34−, CD45−.

24. A method according to claim 1, in which the MSCs display reduced expression of at least one of HESX1, POUFL5, SOX-2, UTF-1 and ZFP42.

25. A method according to claim 1, in which the MSCs display reduced expression of at least one of OCT4, NANOG and SOX2.

26. A method according to claim 1, in which the MSCs display no detectable alkaline phosphatase activity.

27. A method according to claim 1, in which the MSCs are not teratogenic when implanted in SCID mice.

28. A method according to claim 1, in which the MSCs are negative for mouse-specific c-mos repeat sequences and positive for human specific alu repeat sequences.

29. A method according to claim 1, in which the MSCs are capable of undergoing osteogenesis, adipogenesis or chondrogenesis.

30. A method according to claim 2, in which the mesenchymal progenitor cell line comprises huES9.E1, huES9.E3 or H1.E2.

31. A method according to claim 1, in which at least two mesenchymal stem cells selected by the method exhibit substantially identical gene expression profiles.

32. A method according to claim 1, in which a gene expression correlation coefficient between any two or more isolates of mesenchymal stem cells obtained by the method is greater than 0.9.

33. A method according to claim 1, in which at least two isolates of mesenchymal stem cells obtained by the method are substantially similar with each other.

34. A method according to claim 1, in which a gene expression correlation coefficient between a mesenchymal stem cell obtained by the method and cells of a parental culture is greater than 0.8.

35. A method according to claim 1, further comprising deriving a cell line from the cell selected therefrom.

36. A method according to claim 1, further comprising differentiating the mesenchymal stem cell.

37. A method according to claim 36, in which the differentiated mesenchymal cell is an osteocyte, an adipocyte or a chondrocyte.

38. A method of deriving a cell culture from an embryonic stem cell, the method comprising:
(a) providing an embryonic stem cell (ESC) colony;
(b) dispersing the ESC colony with trypsin;
(c) propagating the dispersed cells: (i) in the absence of a feeder layer, (ii) in serum free media in the presence of FGF2, and (iii) in the absence of transformation; and
(d) selecting cells from the propagated cells based on expression of one or more cell surface markers, and
(e) growing the cells selected in step (d) in medium comprising serum;
thereby deriving a cell culture therefrom an embryonic stem cell.

39. A method according to claim 29, in which the MSC is capable of differentiating into osteocytes, adipocytes or chondrocytes.

40. A method according to claim 38, further comprising differentiating the cell line.

41. A method according to claim 38, further comprising differentiating the cell culture.

42. A method according to claim 38, wherein the dispersed ESC colony of step (b) is propagated to confluence and dispersed with trypsin prior to step (c).

43. A method according to claim 38, further comprising selecting a mesenchymal stem cell from the propagated cells based on expression of a cell surface marker.

44. A method according to claim 38, wherein the ESC colony is a human ESC.

* * * * *